US006919351B2

(12) United States Patent
Anthony et al.

(10) Patent No.: US 6,919,351 B2
(45) Date of Patent: Jul. 19, 2005

(54) AZA- AND POLYAZA-NAPHTHALENYL-CARBOXAMIDES USEFUL AS HIV INTEGRASE INHIBITORS

(75) Inventors: Neville J. Anthony, Chalfont, PA (US); Robert P. Gomez, Perkasie, PA (US); Steven D. Young, Lansdale, PA (US); Melissa S. Egbertson, Ambler, PA (US); John S. Wai, Harleysville, PA (US); Jennifer J. Bennett, Lansdale, PA (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 10/399,083

(22) PCT Filed: Oct. 9, 2001

(86) PCT No.: PCT/US01/31550

§ 371 (c)(1),
(2), (4) Date: Aug. 21, 2003

(87) PCT Pub. No.: WO02/30426

PCT Pub. Date: Apr. 18, 2002

(65) Prior Publication Data

US 2004/0034221 A1 Feb. 19, 2004

Related U.S. Application Data

(60) Provisional application No. 60/239,708, filed on Oct. 12, 2000.

(51) Int. Cl.$^7$ .................. A61K 31/4375; A61K 31/502; A61K 31/5415; C07D 471/04; C07D 417/12

(52) U.S. Cl. .................. 514/300; 514/225.2; 514/225.8; 514/248; 514/314; 546/123; 546/169; 544/42; 544/43; 544/46; 544/236; 544/237; 544/184; 544/279

(58) Field of Search .................. 546/123, 169; 544/42, 43, 46, 237; 514/300, 314, 225.2, 225.8, 248

(56) References Cited

U.S. PATENT DOCUMENTS

| 3,945,995 | A | | 3/1976 | Yamada et al. |
|---|---|---|---|---|
| 4,416,884 | A | | 11/1983 | Ishikawa et al. |
| 4,996,213 | A | | 2/1991 | Mendes et al. |
| 5,294,620 | A | | 3/1994 | Ratcliffe et al. |
| 5,633,262 | A | | 5/1997 | Hong et al. |
| 5,753,666 | A | | 5/1998 | Beasley et al. |
| 5,776,944 | A | | 7/1998 | Hong et al. |
| 5,945,431 | A | | 8/1999 | Jin et al. |
| 6,143,760 | A | * | 11/2000 | Albaugh et al. ............ 514/300 |
| 6,211,376 | B1 | | 4/2001 | Romines et al. |
| 6,262,055 | B1 | | 7/2001 | Young et al. |
| 6,294,547 | B1 | | 9/2001 | Oka et al. |
| 6,306,891 | B1 | | 10/2001 | Selnick et al. |
| 6,380,249 | B1 | | 4/2002 | Young et al. |
| 6,525,042 | B1 | | 2/2003 | Kobayashi et al. |

FOREIGN PATENT DOCUMENTS

| WO | WO 96/25399 A1 | 8/1996 |
|---|---|---|
| WO | WO 98/11073 A1 | 3/1998 |
| WO | WO 98/13350 A1 | 4/1998 |
| WO | WO 99/10347 A1 | 3/1999 |
| WO | WO 99/15526 A2 | 4/1999 |
| WO | WO 99/32450 A1 | 7/1999 |
| WO | WO 00/03992 A1 | 1/2000 |
| WO | WO 01/00578 A1 | 1/2001 |
| WO | WO 02/04443 A2 | 1/2002 |
| WO | WO 02/06246 A1 | 1/2002 |
| WO | WO 03/035076 A1 | 5/2003 |
| WO | WO 03/035077 A1 | 5/2003 |

OTHER PUBLICATIONS

Parrill AL. Current Medicinal Chemistry. 2003, 10(18): 1811–24.*
Zouhiri et al. J. Med. Chem. 2003, 43, 1533–1540.*
Y. Pommier et al., "Retroviral Integrase Inhibitors Year 2000: Update and Perspectives", 2000, pp. 532–565, vol. 47, Antiviral Research.
E. De Clercq et al., "New Anti–HIV Agents and Targets", 2002, pp. 531–565, vol. 22, Medicinal Research Reviews.
D. J. Hazuda et al., "Integrase Inhibitors and Cellular Immunity Suppress Retroviral Replication in Rhesus Macaques", 2004, pp. 528–532, vol. 305, Science.
D. J. Hazuda et al., "A Naphthyridine Carboxamide Provides Evidence for Discordant Resistance Between Mechanistically Indentical Inhibitors of HIV–1 Integrase", 2004, pp. 11233–11238, vol. 101, No. 31, PNAS.
S. Bonnenfant et al., "Styrylquinolines, Integrase Inhibitors Acting Prior to Integration: a New Mechanism of Action for Anti–Integrase Agents", 2004, pp. 5728–5736, vol. 78, No. 11, Journal of Virology.
A. L. Parrill et al., "HIV–1 Integrase Inhibition: Binding Sites, Structure Activity Relationships and Future Perspectives", 2003, pp. 1811–1824, vol. 10, Current Medicinal Chemistry. (Full text).
L. Ratner et al., "Complete Nucleotide Sequence of the AIDS virus, HTLV III", 1985, Nature, vol. 313, pp. 277–284.

(Continued)

Primary Examiner—Evelyn Mei Huang
(74) Attorney, Agent, or Firm—Kenneth R. Walton; Valerie J. Camara

(57) ABSTRACT

Aza- and polyaza-naphthalenyl carboxamide derivatives including certain quinoline carboxamide and naphthyridine carboxamide derivatives are described as inhibitors of HIV integrase and inhibitors of HIV replication. These compounds are useful in the prevention or treatment of infection by HIV and the treatment of AIDS, as compounds or pharmaceutically acceptable salts, or as ingredients in pharmaceutical compositions, optionally in combination with other antivirals, immunomodulators, antibiotics or vaccines. Methods of preventing, treating or delaying the onset of AIDS and methods of preventing or treating infection by HIV are also described.

10 Claims, No Drawings

OTHER PUBLICATIONS

H. Toh et al., "Close Structural Resemblance Between Putative Polymerase of a Drosophila Transposable Genetic Element 17.6 and Pol Gene Product of Moloney Murine Leukaemia Virus", 1985, The EMBO Journal, vol. 4, No. 5, pp. 1267–1272.

M.D. Power et al., "Nucleotide Sequence of SRV–1, Type D Simian Acquired Immune Deficiency Syndrome Retrovirus", 1986, Science, vol. 231, pp. 1567–1572.

L.H. Pearl et al., "A Structural Model for the Retroviral Process", 1987, Nature, vol. 329, pp. 351–354.

L. Chan et al., "Discovery of 1,6–Naphthyridines as a Novel Class of Potent and Selective Human Cytomegalovirus Inhibitors", 1999, J. Med. Chem., vol. 42, No. 16, pp. 3023–3025.

M. Ouali et al., "Modeling of the Inhibition of Retroviral Integrases by Styrylquinoline Derivatives", 2000, J. Med. Chem., vol. 43, pp. 1949–1957.

Derwent Abstract No. 97–048296/05, 1997 (Abstract of JP 08301849–A, Takeda Chem. Ind. Ltd., "New Heterocyclic Carboxamide Derivs.–Useful in Pharmaceuticals as Tachykinin Receptor Inhibitors").

Chemical Abstracts No. 33–2525, 1938 (Abstract of Otiai et al., "Synthesis of 2.5 Naphthyridine Derivatives, II", J. Pharm, Soc. Japan, vol. 58, pp. 764–770).

CAPLUS Accession No. 2001:923611, 2001, Kiyama et al., (Abstract of WO 01/95905, Assignee: Shionogi & Co., Ltd., "Dual Divalent Metal Ion Chelators as HIV Integrase Inhibitors").

Derwent Abstract No. 2002–732783,2002 (Abstract of WO 02/070491, Fuji, M., "New Nitrogenous Heteroaromatic Compounds are HIV Integrase Inhibitors for Treating HIV Infections, AIDS and AIDS Related Diseases".

IPDL Abstract of WO 02/070486, Shionogi & Co., Ltd., Fuji et al., "Nitrogen– Containing Heteroaryl Compounds Having HIV Integrase Inhibitory Activity").

J. Bedard et al., "Antiviral Properties of a Series of 1,6–Naphthyridine and 7,8–Dihyroisoquinoline Derivatives Exhibiting Potent Activity Against Human Cytomegalovirus", 2004, vol. 44, Antimicrobial Agents and Chemotherapy.

* cited by examiner

SEQUENCE LISTING

<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: synthetic DNA

<400> SEQUENCE: 1
tgaccaaggg ctaattcact          20

<210> SEQ ID NO 2
<211> LENGTH: 20
<212> TYPE: DNA
<213> ORGANISM: Artificial Sequence
<220> FEATURE:
<223> OTHER INFORMATION: synthetic DNA

<400> SEQUENCE: 2
actggttccc gattaagtga          20

AZA-AND POLYAZA-NAPHTHALENYL-CARBOXAMIDES USEFUL AS HIV INTEGRASE INHIBITORS

This application is the national phase filing under 35 U.S.C. §371 of International Application No. PCT/US 01/31550, filed Oct. 9, 2001, which claims benefit of U.S. Provisional Application No. 60/239,708, filed Oct. 12, 2000.

FIELD OF THE INVENTION

The present invention is directed to aza- and polyaza-naphthalenyl carboxamides and pharmaceutically acceptable salts thereof, their synthesis, and their use as inhibitors of the HIV integrase enzyme. The compounds of the present invention include 7-(N-substituted carboxamido)-8-hydroxy-1,6-naphthyridines and quinoxalines. The compounds and pharmaceutically acceptable salts thereof of the present invention are useful for preventing or treating infection by HIV and for treating AIDS.

References are made throughout this application to various published documents in order to more fully describe the state of the art to which this invention pertains. The disclosures of these references are hereby incorporated by reference in their entireties.

BACKGROUND OF THE INVENTION

A retrovirus designated human immunodeficiency virus (HIV) is the etiological agent of the complex disease that includes progressive destruction of the immune system (acquired immune deficiency syndrome; AIDS) and degeneration of the central and peripheral nervous system. This virus was previously known as LAV, HTLV-III, or ARV. A common feature of retrovirus replication is the insertion by virally-encoded integrase of proviral DNA into the host cell genome, a required step in HIV replication in human T-lymphoid and monocytoid cells. Integration is believed to be mediated by integrase in three steps: assembly of a stable nucleoprotein complex with viral DNA sequences; cleavage of two nucleotides from the 3' termini of the linear proviral DNA; covalent joining of the recessed 3' OH termini of the proviral DNA at a staggered cut made at the host target site. The fourth step in the process, repair synthesis of the resultant gap, may be accomplished by cellular enzymes.

Nucleotide sequencing of HIV shows the presence of a pol gene in one open reading frame [Ratner, L. et al., Nature, 313, 277(1985)]. Amino acid sequence homology provides evidence that the pol sequence encodes reverse transcriptase, integrase and an HIV protease [Toh, H. et al., EMBO J. 4, 1267 (1985); Power, M. D. et al., Science, 231, 1567 (1986); Pearl, L. H. et al., Nature, 329, 351 (1987)]. All three enzymes have been shown to be essential for the replication of HIV.

It is known that some antiviral compounds which act as inhibitors of HIV replication are effective agents in the treatment of AIDS and similar diseases, including reverse transcriptase inhibitors such as azidothymidine (AZT) and efavirenz and protease inhibitors such as indinavir and nelfinavir. The compounds of this invention are inhibitors of HIV integrase and inhibitors of HIV replication. The inhibition of integrase in vitro and HIV replication in cells is a direct result of inhibiting the strand transfer reaction catalyzed by the recombinant integrase in vitro in HIV infected cells. The particular advantage of the present invention is highly specific inhibition of HIV integrase and HIV replication.

The following references are of interest as background:

Chemical Abstracts No. 33-2525 discloses the preparation of 5-chloro-8-hydroxy-1,6-naphthyridine-7-carboxylic acid amide from the corresponding methyl ester.

Derwent Abstract No. 97-048296 is an abstract of Japanse Published Application No. 08301849. The abstract discloses certain heterocyclic carboxamide derivatives. The derivatives are said to be useful as tachykinin receptor inhibitors. N-(3,5-bis(trifluoromethyl)benzyl-1,2-dihydro-N,2-dimethyl-1-oxo-4-pyrrolidino-3-isoquinoline carboxamide is specifically disclosed.

WO 98/13350 discloses certain quinoline derivatives which inhibit vascular endothelial growth factor. The reference also discloses certain 1,8-naphthryidine derivatives; i.e., Examples 53 and 54 respectively describe preparations of 2-acetamido-5-(2-fluoro-5-hydroxy-4-methylanilino)-1,8-naphthyridine and 2-amino-5-(2-fluoro-5-hydroxy-4-methylanilino)-1,8-naphthyridine.

WO 99/32450 discloses 4-hydroxyquinoline-2-carboxamide derivatives which are proposed for use in treating herpes virus infections.

WO 98/11073 discloses 8-hydroxyquinoline-7-carboxamides which are proposed for use in treating herpes virus infections.

SUMMARY OF THE INVENTION

The present invention is directed to novel aza- and polyaza-naphthalenyl carboxamides. These compounds are useful in the inhibition of HIV integrase, the prevention of infection by HIV, the treatment of infection by HIV and in the prevention, treatment, and delay in the onset of AIDS and/or ARC, either as compounds, pharmaceutically acceptable salts or hydrates (when appropriate), pharmaceutical composition ingredients, whether or not in combination with other HIV/AIDS antivirals, anti-infectives, immunomodulators, antibiotics or vaccines. More particularly, the present invention includes a compound of Formula (I):

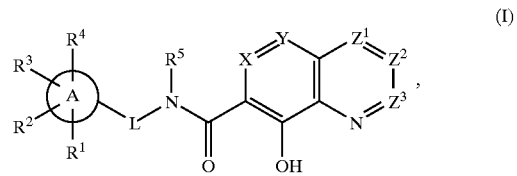

wherein A is a heterocycle;
A is substituted by $R^1$, $R^2$, $R^3$, and $R^4$;
L is a linker connecting a ring atom of A to the nitrogen of the —N($R^5$)— moiety, wherein L is
  (i) a single bond,
  (ii) —($C_{1-6}$ alkyl)-,
  (iii) —($C_{2-6}$ alkenyl)-,
  (iv) —($C_{0-6}$ alkyl)-($C_{3-6}$ cycloalkyl)-($C_{0-6}$ alkyl)-, or
  (v) —($C_{0-6}$ alkyl)-M-($C_{0-6}$ alkyl)-, wherein M is —N($R^a$)—, —OC(=O)—, or —C(=O)O—; wherein the alkenyl in (iii) and the alkyls in (ii), (iv), and (v) are independently and optionally substituted with 1, 2, or 3 substituents independently selected from the group consisting of halogen, —OH, —$C_{1-6}$ alkyl, —O—$C_{1-6}$ alkyl, —$CO_2R^a$, —$CO_2(CH_2)_{1-2}R^k$, —$C_{1-6}$ alkyl-$OR^a$, —$R^k$, —$(CH_2)_{1-2}R^k$, —CH($OR^a$)—$R^k$, and —CH(N($R^a$)$_2$)—$R^k$;
X is N or C—$Q^1$;
Y is N or C—$Q^2$, provided that X and Y are not both N;

$Z^1$ is N or C—$Q^3$;
$Z^2$ is N or C—$Q^4$;
$Z^3$ is N or CH;
each of $Q^1$, $Q^2$, $Q^3$, and $Q^4$ is independently
(1) —H.
(2) —$C_{1-6}$ alkyl,
(3) —$C_{1-6}$ haloalkyl,
(4) —O—$C_{1-6}$ alkyl,
(5) —O—$C_{1-6}$ haloalkyl,
(6) halo,
(7) —CN,
(8) —$C_{1-6}$ alkyl-$OR^a$,
(9) —$C_{0-6}$ alkyl-C(=O)$R^a$,
(10) —$C_{0-6}$ alkyl-$CO_2R^a$,
(11) —$C_{0-6}$ alkyl-$SR^a$,
(12) —$N(R^a)_2$,
(13) —$C_{1-6}$ alkyl-$N(R^a)_2$,
(14) —$C_{0-6}$ alkyl-C(=O)$N(R^a)_2$,
(15) —$C_{0-6}$ alkyl-G-$C_{1-6}$ alkyl-C(=O)$N(R^a)_2$, wherein G is O, S, $N(R^a)$, or $N(SO_2R^a)$,
(16) —$N(R^a)$—$C(R^a)$=O,
(17) —$C_{1-6}$ alkyl-$N(R^a)$—$C(R^a)$=O,
(18) —C(=O)—$N(R^a)$—$C_{1-6}$ alkyl-[C(=O)]$_{0-1}$—$N(R^a)_2$,
(19) —C(=O)—$N(R^a)$—$C_{1-6}$ alkyl substituted with 1 or 2-$OR^a$,
(20) —$C_{0-6}$ alkyl-$SO_2R^a$,
(21) —$C_{0-6}$ alkyl-$N(R^a)SO_2R^a$,
(22) —$C_{2-6}$ alkenyl,
(23) —$C_{2-6}$ alkenyl-C(=O)—$N(R^a)_2$,
(24) —$C_{2-5}$ alkynyl,
(25) —$C_{2-5}$ alkynyl-$CH_2N(R^a)_2$,
(26) —$C_{2-5}$ alkynyl-$CH_2OR^a$,
(27) —$C_{2-5}$ alkynyl-$CH_2S(O)_n$—$R^a$, or
(28)

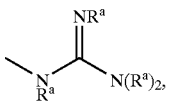

(29)

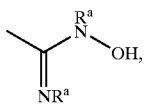

(30) —C(=$NR^a$)—$N(R^a)_2$,
(31) —$N(R^a)$—$C_{1-6}$ alkyl-$S(O)_nR^a$,
(32) —$N(R^a)$—$C_{1-6}$ alkyl-$OR^a$,
(33) —$N(R^a)$—$C_{1-6}$ alkyl-$N(R^a)_2$,
(34) —$N(R^a)$—$C_{1-6}$ alkyl-$N(R^a)$—$C(R^a)$=O,
(35) —$N(R^a)$—$C_{0-6}$ alkyl-[C(=O)]$_{1-2}N(R^a)_2$,
(36) —$N(R^a)$—$C_{1-6}$ alkyl-$CO_2R^a$,
(37) —$N(R^a)C$(=O)$N(R^a)$—$C_{1-6}$ alkyl-C(=O)$N(R^a)_2$,
(38) —$N(R^a)C$(=O)—$C_{1-6}$ alkyl-$N(R^a)_2$,
(39) —$N(R^a)$—$SO_2$-$N(R^a)_2$,
(40) —$R^k$,
(41) —$C_{1-6}$ alkyl substituted with $R^k$,
(42) —$C_{1-6}$ haloalkyl substituted with $R^k$,
(43) —$C_{2-5}$ alkenyl-$R^k$,
(44) —$C_{2-5}$ alkynyl-$R^k$,
(45) —$C_{0-6}$ alkyl-O-$R^k$,
(46) —$C_{0-6}$ alkyl-O—$C_{1-6}$ alkyl-$R^k$,
(47) —$C_{0-6}$ alkyl-$S(O)_n$—$R^k$,
(48) —$C_{0-6}$ alkyl-$S(O)_n$—$C_{1-6}$ alkyl-$R^k$,
(49) —O—$C_{1-6}$ alkyl-$OR^k$,
(50) —O—$C_{1-6}$ alkyl-O—$C_{1-6}$ alkyl-$R^k$,
(51) —O—$C_{1-6}$ alkyl-$S(O)_nR^k$,
(52) —$C_{0-6}$ alkyl-$N(R^c)$—$R^k$,
(53) —$C_{0-6}$ alkyl-$N(R^c)$—$C_{1-6}$ alkyl substituted with one or two $R^k$ groups,
(54) —$C_{0-6}$ alkyl-$N(R^c)$—$C_{1-6}$ alkyl-$OR^k$,
(55) —$C_{0-6}$ alkyl-C(=O)—$R^k$,
(56) —$C_{0-6}$ alkyl-C(=O)$N(R^a)$—$R^k$,
(57) —$C_{0-6}$ alkyl-$N(R^a)C$(=O)—$R^k$,
(58) —$C_{0-6}$ alkyl-C(=O)$N(R^a)$—$C_{1-6}$ alkyl-$R^k$, or
(59) —$C_{0-6}$ alkyl-$N(R^a)$—$C_{0-6}$ alkyl-$S(O)_nR^k$;
each of $R^1$ and $R^2$ is independently:
(1) —H,
(2) —$C_{1-6}$ alkyl,
(3) —$C_{1-6}$ haloalkyl,
(4) —O—$C_{1-6}$ alkyl,
(5) —O—$C_{1-6}$ haloalkyl,
(6) —OH
(7) halo,
(8) —$NO_2$,
(9) —CN,
(10) —$C_{1-6}$ alkyl-$OR^a$,
(11) —$C_{0-6}$ alkyl-C(=O)$R^a$,
(12) —$C_{0-6}$ alkyl-$CO_2R^a$,
(13) —$C_{0-6}$ alkyl-$SR^a$,
(14) —$N(R^a)_2$,
(15) —$C_{1-6}$ alkyl-$N(R^a)_2$,
(16) —$C_{0-6}$ alkyl-C(=O)$N(R^a)_2$,
(17) —$C_{1-6}$ alkyl-$N(R^a)$—$C(R^a)$=O,
(18) —$SO_2R^a$,
(19) —$N(R^a)SO_2R^a$,
(20) —$C_{2-5}$ alkenyl,
(21) —O—$C_{1-6}$ alkyl-$OR^a$,
(22) —O—$C_{1-6}$ alkyl-$SR^a$,
(23) —O—$C_{1-6}$ alkyl-NH—$CO_2R^a$,
(24) —O—$C_{2-6}$ alkyl-$N(R^a)_2$,
(25) —$N(R^a)$—$C_{1-6}$ alkyl-$SR^a$,
(26) —$N(R^a)$—$C_{1-6}$ alkyl-$OR^a$,
(27) —$N(R^a)$—$C_{1-6}$ alkyl-$N(R^a)_2$,
(28) —$N(R^a)$—$C_{1-6}$ alkyl-$N(R^a)$—$C(R^a)$=O,
(29) —$R^k$,
(30) —$C_{1-6}$ alkyl substituted with 1 or 2 $R^k$ groups,
(31) —$C_{1-6}$ haloalkyl substituted with 1 or 2 $R^k$ groups,
(32) —$C_{2-5}$ alkenyl-$R^k$,
(33) —$C_{2-5}$ alkynyl-$R^k$,
(34) —O-$R^k$,
(35) —O—$C_{1-6}$ alkyl-$R^k$,
(36) —$S(O)_n$—$R^k$,

(37) —S(O)$_n$—C$_{1-6}$ alkyl-R$^k$,
(38) —O—C$_{1-6}$ alkyl-OR$^k$,
(39) —O—C$_{1-6}$ alkyl-O—C$_{1-6}$ alkyl-R$^k$,
(40) —O—C$_{1-6}$ alkyl-S(O)$_n$R$^k$,
(41) —C$_{1-6}$ alkyl (OR$^b$)(R$^k$),
(42) —C$_{1-6}$ alkyl (OR$^b$)(—C$_{1-6}$ alkyl-R$^k$),
(43) —C$_{0-6}$ alkyl-N(R$^b$)(R$^k$),
(44) —C$_{0-6}$ alkyl-N(R$^b$)(—C$_{1-6}$ alkyl-R$^k$),
(45) —C$_{1-6}$ alkyl S(O)$_n$—R$^k$,
(46) —C$_{1-6}$ alkyl S(O)$_n$—C$_{1-6}$ alkyl-R$^k$,
(47) —C$_{0-6}$ alkyl C(O)—R$^k$, or
(48) —C$_{0-6}$ alkyl C(O)—C$_{1-6}$ alkyl-R$^k$,
each of R$^3$ and R$^4$ is independently
(1) —H,
(2) halo,
(3) —CN,
(4) —NO$_2$.
(5) —OH,
(6) C$_{1-6}$ alkyl,
(7) C$_{1-6}$ haloalkyl,
(8) —O—C$_{1-6}$ alkyl,
(9) —O—C$_{1-6}$ haloalkyl,
(10) —C$_{1-6}$ alkyl-OR$^a$,
(11) —C$_{0-6}$ alkyl-C(=O)R$^a$,
(12) —C$_{0-6}$ alkyl-CO$_2$R$^a$,
(13) —C$_{0-6}$ alkyl-SR$^a$,
(14) —N(R$^a$)$_2$,
(15) —C$_{1-6}$ alkyl-N(R$^a$)$_2$,
(16) —C$_{0-6}$ alkyl-C(=O)N(R$^a$)$_2$,
(17) —SO$_2$R$^a$,
(18) —N(R$^a$)SO$_2$R$^a$,
(19) —C$_{2-5}$ alkenyl,
(20) —O—C$_{1-6}$ alkyl-OR$^a$,
(21) —O—C$_{1-6}$ alkyl-SR$^a$,
(22) —O—C$_{1-6}$ alkyl-NH—CO$_2$R$^a$,
(23) —O—C$_{2-6}$ alkyl-N(R$^a$)$_2$, or
(24) oxo;
R$^5$ is
(1) —H,
(2) —C$_{1-6}$ alkyl, optionally substituted with from 1 to 5 substituents independently selected from halogen, —O—C$_{1-6}$ alkyl, —O—C$_{1-6}$ haloalkyl, —N(R$^a$)$_2$, and —CO$_2$R$^a$;
(3) aryl optionally substituted with from 1 to 5 substituents independently selected from halogen, C$_{1-6}$ alkyl, C$_{1-6}$ haloalkyl, —O—C$_{1-6}$ alkyl, —O—C$_{1-6}$ haloalkyl, —S—C$_{1-6}$ alkyl, —CN, and —OH, or
(4) —C$_{1-6}$ alkyl substituted with R$^k$;
each R$^a$ is independently —H, —C$_{1-6}$ alkyl, or —C$_{1-6}$ haloalkyl;
each R$^b$ is independently:
(1) —H,
(2) —C$_{1-4}$ alkyl,
(3) —C$_{1-4}$ haloalkyl,
(4) —R$^k$,
(5) —C$_{2-3}$ alkenyl,
(6) —C$_{1-4}$ alkyl-R$^k$,
(7) —C$_{2-3}$ alkenyl-R$^k$,
(8) —S(O)$_n$—R$^k$, or
(9) —C(O)—R$^k$;
each R$^c$ is independently
(1) —H,
(2) —C$_{1-6}$ alkyl,
(3) —C$_{1-6}$ alkyl substituted with —N(R$^a$)$_2$, or
(4) —C$_{1-4}$ alkyl-aryl, wherein aryl is optionally substituted with 1 to 5 substituents independently selected from halogen, C$_{1-6}$ alkyl, C$_{1-6}$ haloalkyl, —O—C$_{1-6}$ alkyl, —O—C$_{1-6}$ haloalkyl, —S—C$_{1-6}$ alkyl, —CN, and —OH;
each R$^k$ is independently carbocycle or heterocycle, wherein the carbocycle and heterocycle are unsubstituted or substituted with from 1 to 5 substituents each of which is independently selected from
(a) halogen,
(b) —C$_{1-6}$ alkyl,
(c) —C$_{1-6}$ haloalkyl,
(d) —O—C$_{1-6}$ alkyl,
(e) —O—C$_{1-6}$ haloalkyl,
(f) —S—C$_{1-6}$ alkyl,
(g) —CN,
(h) —OH,
(i) oxo,
(j) —C$_{0-6}$ alkyl-C(=O)N(R$^a$)$_2$,
(k) —C$_{0-6}$ alkyl-C(=O)R$^a$,
(l) —N(R$^a$)—C(=O)R$^a$,
(m) —N(R$^a$)—CO$_2$R$^a$,
(n) —C$_{1-6}$ alkyl-N(R$^a$)—C(=O)R$^a$,
(o) —N(R$^a$)$_2$,
(p) —C$_{1-6}$ alkyl-N(R$^a$)$_2$,
(q) —C$_{1-6}$ alkyl-OR$^a$,
(r) —C$_{0-6}$ alkyl-CO$_2$R$^a$,
(s) —C$_{0-6}$ alkyl-O—C$_{1-6}$ alkyl-OR$^a$,
(t) —SO$_2$R$^a$,
(u) —SO$_2$N(R$^a$)$_2$,
(v) —C$_{0-6}$ alkyl-CO$_2$—C$_{2-5}$ alkenyl,
(w) aryl,
(x) aryloxy-,
(y) —C$_{1-4}$ alkyl substituted with aryl,
(z) heteromonocycle,
(aa) —C$_{1-4}$ alkyl substituted with a heteromonocycle,
(bb) heteromonocyclylcarbonyl-C$_{0-6}$ alkyl-, and
(cc) N-heteromonocyclyl-N-C$_{1-6}$ alkyl-amino-;
wherein the aryl group in (w) aryl, (x) aryloxy, and (y) —C$_{1-4}$ alkyl substituted with aryl, is optionally substituted with from 1 to 4 substituents independently selected from halogen, C$_{1-6}$ alkyl, —O—C$_{1-6}$ alkyl, C$_{1-6}$ alkyl substituted with N(R$^a$)$_2$, C$_{1-6}$ haloalkyl, and —OH; and
wherein the heteromonocyclyl group in (z) heteromonocycle, (aa) —C$_{1-4}$ alkyl substituted with a heteromonocycle, (bb) heteromonocyclyl-carbonyl-C$_{0-6}$ alkyl-, and (cc) N-heteromonocyclyl-N—C$_{1-6}$ alkyl-amino- is optionally substituted with from 1 to 4 substituents independently selected from halogen, C$_{1-6}$ alkyl, —O—C$_{1-6}$ alkyl, C$_{1-6}$ haloalkyl, oxo, and —OH; and
each n is independently an integer equal to 0, 1 or 2;
and with the proviso that when Z$^1$ is C—Q$^3$, Z$^2$ is C—Q$^4$, Z$^3$ is CH, and X is C—Q$^1$, then Y is not C—Q$^2$;
or a pharmaceutically acceptable salt thereof.

The present invention also includes pharmaceutical compositions containing a compound of the present invention and methods of preparing such pharmaceutical compositions. The present invention further includes methods of treating AIDS, methods of delaying the onset of AIDS, methods of preventing AIDS, methods of preventing infection by HIV, and methods of treating infection by HIV.

Other embodiments, aspects and features of the present invention are either further described in or will be apparent from the ensuing description, examples and appended claims.

DETAILED DESCRIPTION OF THE INVENTION

The present invention includes the aza- and polyazanaphthalenyl carboxamides of Formula (I) above. These compounds and pharmaceutically acceptable salts thereof are HIV integrase inhibitors.

A first embodiment of the present invention is a compound of Formula I, wherein:

each of $Q^1$, $Q^2$, $Q^3$ and $Q^4$ is independently
- (1) —H,
- (2) —$C_{1-6}$ alkyl,
- (3) —$C_{1-6}$ fluoroalkyl,
- (4) —O—$C_{1-6}$ alkyl,
- (5) —O—$C_{1-6}$ fluoroalkyl,
- (6) halo,
- (7) —CN,
- (8) —$C_{1-6}$ alkyl-$OR^a$,
- (9) —$C_{0-6}$ alkyl-C(=O)$R^a$,
- (10) —$C_{0-6}$ alkyl-$CO_2R^a$,
- (11) —$C_{0-6}$ alkyl-$SR^a$,
- (12) —$N(R^a)_2$,
- (13) —$C_{1-6}$ alkyl —$N(R^a)_2$,
- (14) —$C_{0-6}$ alkyl-C(=O)$N(R^a)_2$,
- (15) —$C_{1-6}$ alkyl-$N(R^a)$—C($R^a$)=O,
- (16) —$SO_2R^a$,
- (17) —$N(R^a)SO_2R^a$,
- (18) —$C_{2-5}$ alkynyl, (19) —$C_{2-5}$ alkynyl-$CH_2N(R^a)_2$,
- (20) —$C_{2-5}$ alkynyl-$CH_2OR^a$,
- (21)

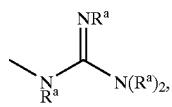

- (22) —N($R^a$)—$C_{1-6}$ alkyl-$SR^a$,
- (23) —N($R^a$)—$C_{1-6}$ alkyl-$OR^a$,
- (24) —N($R^a$)—$C_{1-6}$ alkyl-$N(R^a)_2$,
- (25) —N($R^a$)—$C_{1-6}$ alkyl-$N(R^a)$—C($R^a$)=O,
- (26) —$R^k$,
- (27) —$C_{1-6}$ alkyl substituted with $R^k$,
- (28) —$C_{1-6}$ fluoroalkyl substituted with $R^k$,
- (29) —$C_{2-5}$ alkenyl-$R^k$,
- (30) —$C_{2-5}$ alkynyl-$R^k$,
- (31) —O-$R^k$,
- (32) —O—$C_{1-14}$ alkyl-$R^k$,
- (33) —S(O)$_n$—$R^k$,
- (34) —S(O)$_n$—$C_{1-4}$ alkyl-$R^k$,
- (35) —O—$C_{1-6}$ alkyl-$OR^k$,
- (36) —O—$C_{1-6}$ alkyl-O—$C_{1-4}$ alkyl-$R^k$,
- (37) —O—$C_{1-6}$ alkyl-$SR^k$,
- (38) —N($R^c$)—$R^k$,
- (39) —N($R^c$)—$C_{1-6}$ alkyl substituted with one or two $R^k$ groups,
- (40) —N($R^c$)—$C_{1-6}$ alkyl-$OR^k$,
- (41) —C(=O)N—$C_{1-6}$ alkyl-$R^k$,
- (42) —$C_{2-5}$ alkynyl-$CH_2S(O)_n$—$R^a$, or
- (43) —C(=$NR^a$)—$N(R^a)_2$;

each of $R^1$ and $R^2$ is independently:
- (1) —H,
- (2) —$C_{1-6}$ alkyl,
- (3) —$C_{1-6}$ fluoroalkyl,
- (4) —O—$C_{1-6}$ alkyl,
- (5) —O—$C_{1-6}$ fluoroalkyl,
- (6) —OH
- (7) halo,
- (8) —$NO_2$,
- (9) —CN,
- (10) —$C_{1-6}$ alkyl-$OR^a$,
- (11) —$C_{0-6}$ alkyl-C(=O)$R^a$,
- (12) —$C_{0-6}$ alkyl$CO_2R^a$,
- (13) —$C_{0-6}$ alkyl-$SR^a$,
- (14) —$N(R^a)_2$,
- (15) —$C_{1-6}$ alkyl $N(R^a)_2$,
- (16) —$C_{0-6}$ alkyl-C(=O)$N(R^a)_2$,
- (17) —$C_{1-6}$ alkyl-$N(R^a)$—C($R^a$)=O,
- (18) —$SO_2R^a$,
- (19) —$N(R^a)SO_2R^a$,
- (20) —$C_{2-5}$ alkenyl,
- (21) —O—$C_{1-6}$ alkyl-$OR^a$,
- (22) —O—$C_{1-6}$ alkyl-$SR^a$,
- (23) —O—$C_{1-6}$ alkyl-NH—$CO_2R^a$,
- (24) —O—$C_{2-6}$ alkyl-$N(R^a)_2$,
- (25) —N($R^a$)—$C_{1-6}$ alkyl-$SR^a$,
- (26) —N($R^a$)—$C_{1-6}$ alkyl-$OR^a$,
- (27) —N($R^a$)—$C_{1-6}$ alkyl-$N(R^a)_2$,
- (28) —N($R^a$)—$C_{1-6}$ alkyl-$N(R^a)$—C($R^a$)=O,
- (29) —$R^k$,
- (30) —$C_{1-6}$ alkyl substituted with 1 or 2 $R^k$ groups,
- (31) —$C_{1-6}$ fluoroalkyl substituted with 1 or 2 $R^k$ groups,
- (32) —$C_{2-5}$ alkenyl-$R^k$,
- (33) —$C_{2-5}$ alkynyl-$R^k$,
- (34) —$OR^k$,
- (35) —O—$C_{1-4}$ alkyl-$R^k$,
- (36) —S(O)$_n$—$R^k$,
- (37) —S(O)$_n$—$C_{1-4}$ alkyl-$R^k$,
- (38) —O—$C_{1-6}$ alkyl-$OR^k$,
- (39) —O—$C_{1-6}$ alkyl-O—$C_{1-4}$ alkyl-$R^k$,
- (40) —O—$C_{1-6}$ alkyl-$SR^k$,
- (41) —$C_{1-6}$ alkyl ($OR^b$)($R^k$),
- (42) —$C_{1-6}$ alkyl ($OR^b$)(—$C_{1-4}$ alkyl-$R^k$),
- (43) —$C_{0-6}$ alkyl-$N(R^b)(R^k)$,

(44) —C$_{0-6}$ alkyl-N(R$^b$)(—C$_{1-4}$ alkyl-R$^k$),
(45) —C$_{1-6}$ alkyl S(O)$_n$—R$^k$,
(46) —C$_{1-6}$ alkyl S(O)$_n$—C$_{1-4}$ alkyl-R$^k$,
(47) —C$_{0-6}$ alkyl C(O)—R$^k$, or
(48) —C$_{0-6}$ alkyl C(O)—C$_{1-4}$ alkyl-R$^k$,
each of R$^3$ and R$^4$ is independently
 (1) —H,
 (2) halo,
 (3) —CN,
 (4) —NO$_2$,
 (5) —OH,
 (6) C$_{1-6}$ alkyl,
 (7) C$_{1-6}$ fluoroalkyl,
 (8) —O—C$_{1-6}$ alkyl,
 (9) —O—C$_{1-6}$ fluoroalkyl,
 (10) —C$_{1-6}$ alkyl-OR$^a$,
 (11) —C$_{0-6}$ alkyl-C(=O)R$^a$,
 (12) —C$_{0-6}$ alkyl-CO$_2$R$^a$,
 (13) —C$_{0-6}$ alkyl-SR$^a$,
 (14) —N(R$^a$)$_2$,
 (15) —C$_{1-6}$ alkyl N(R$^a$)$_2$,
 (16) —C$_{0-6}$ alkyl-C(=O)N(R$^a$)$_2$,
 (17) —SO$_2$R$^a$,
 (18) —N(R$^a$)SO$_2$R$^a$,
 (19) —C$_{2-5}$ alkenyl,
 (20) —O—C$_{1-6}$ alkyl-OR$^a$,
 (21) —O—C$_{1-6}$ alkyl-SR$^a$,
 (22) —O—C$_{1-6}$ alkyl-NH—CO$_2$R$^a$,
 (23) —O—C$_{2-6}$ alkyl-N(R$^a$)$_2$, or
 (24) oxo;
R$^5$ is
 (1) —H,
 (2) —C$_{1-6}$ alkyl, optionally substituted with from 1 to 3 substituents independently selected from halogen, —O—C$_{1-6}$ alkyl, —O—C$_{1-6}$ fluoroalkyl, —N(R$^a$)$_2$, and —CO$_2$R$^a$;
 (3) aryl optionally substituted with from 1 to 5 substituents independently selected from halogen, C$_{1-6}$ alkyl, C$_{1-6}$ fluoroalkyl, —O—C$_{1-6}$ alkyl, —O—C$_{1-6}$ fluoroalkyl, —S—C$_{1-6}$ alkyl, —CN, and —OH, or
 (4) —C$_{1-6}$ alkyl substituted with R$^k$;
each R$^a$ is independently —H, —C$_{1-6}$ alkyl, or —C$_{1-6}$ fluoroalkyl;
each R$^b$ is independently:
 (1) —H,
 (2) —C$_{1-4}$ alkyl,
 (3) —C$_{1-4}$ fluoroalkyl,
 (4) —R$^k$,
 (5) —C$_{2-3}$ alkenyl,
 (6) —C$_{1-4}$ alkyl-R$^k$,
 (7) —C$_{2-3}$ alkenyl-R$^k$,
 (8) —S(O)$_n$—R$^k$, or
 (9) —C(O)—R$^k$;
each R$^c$ is independently
 (1) —H,
 (2) —C$_{1-6}$ alkyl,
 (3) —C$_{1-6}$ alkyl substituted with —N(R$^a$)$_2$, or
 (4) —C$_{1-4}$ alkyl-aryl, wherein aryl is optionally substituted with 1 to 5 substituents independently selected from halogen, C$_{1-6}$ alkyl, C$_{1-6}$ fluoroalkyl, —O—C$_{1-6}$ alkyl, —O—C$_{1-6}$ fluoroalkyl, —S—C$_{1-6}$ alkyl, —CN, and —OH;
each R$^k$ is independently carbocycle or heterocycle, wherein the carbocycle and heterocycle are unsubstituted or substituted with from 1 to 5 substituents each of which is independently selected from
 (a) halogen,
 (b) C$_{1-6}$ alkyl,
 (c) C$_{1-6}$ fluoroalkyl,
 (d) —O—C$_{1-6}$ alkyl,
 (e) —O—C$_{1-6}$ fluoroalkyl,
 (f) —S—C$_{1-6}$ alkyl,
 (g) —CN,
 (h) —OH,
 (i) oxo,
 (j) —(CH$_2$)$_{0-3}$C(=O)N(R$^a$)$_2$,
 (k) —(CH$_2$)$_{0-3}$C(=O)R$^a$,
 (l) —N(R$^a$)—C(=O)R$^a$,
 (m) —N(R$^a$)—C(=O)OR$^a$,
 (n) —(CH$_2$)$_{1-3}$N(R$^a$)—C(=O)R$^a$,
 (o) —N(R$^a$)$_2$,
 (p) —C$_{1-6}$ alkyl-N(R$^a$)$_2$,
 (q) aryl,
 (r) aryloxy-,
 (s) —C$_{1-4}$ alkyl substituted with aryl,
 (t) heteromonocycle,
 (u) —C$_{1-4}$ alkyl substituted with a heteromonocycle,
 (v) heteromonocyclylcarbonyl-C$_{0-6}$ alkyl-, and
 (w) N-heteromonocyclyl-N—C$_{1-6}$ alkyl-amino-;
  wherein the aryl group in (q) aryl, (r) aryloxy, and (s) —C$_{1-4}$ alkyl substituted with aryl, is optionally substituted with from 1 to 3 substituents independently selected from halogen, C$_{1-6}$ alkyl, —O—C$_{1-6}$ alkyl, C$_{1-6}$ alkyl substituted with N(R$^a$)$_2$, C$_{1-6}$ fluoroalkyl, and —OH; and
  wherein the heteromonocyclyl group in (t) heteromonocycle,
 (u) —C$_{1-4}$ alkyl substituted with a heteromonocycle,
 (v) heteromonocyclyl-carbonyl-C$_{0-6}$ alkyl-, and (x) N-heteromonocyclyl-N—C$_{1-6}$ alkyl-amino- is optionally substituted with from 1 to 3 substituents independently selected from halogen, C$_{1-6}$ alkyl, —O—C$_{1-6}$ alkyl, C$_{1-6}$ fluoroalkyl, oxo, and —OH; and
and all other variables are as originally defined above;
and with the proviso that when Z$^1$ is C—Q$^3$, Z$^2$ is C—Q$^4$, Z$^3$ is CH, and X is C—Q$^1$, then Y is not C—Q$^2$;
or a pharmaceutically acceptable salt thereof.

A second embodiment of the present invention is a compound of Formula (I), wherein A is
 (i) a 4- to 7-membered saturated or unsaturated monocylic heterocycle which contains from 1 to 4 nitrogen atoms, from zero to 2 heteroatoms selected from oxygen and sulfur, and a balance of carbon atoms, with at least one of the ring atoms being carbon;
 (ii) a 7- to 11-membered fused bicyclic heterocycle either ring of which is saturated or unsaturated, wherein the fused bicyclic heterocycle contains from 1 to 6 heteroatoms selected from nitrogen, oxygen and sulfur, and a balance of carbon atoms with at least two of the ring atoms being carbon; or (iii) a 11- to 15-membered fused tricyclic heterocycle any ring of which is saturated or unsaturated, wherein the fused tricyclic heterocycle contains from 1 to 6 nitrogen atoms, from zero to 3 heteroatoms selected from oxygen and sulfur, and a balance of carbon atoms with at least three of the ring atoms being carbon;

L is (i) a single bond;

(ii) —$(CH_2)_{1-5}$—, which is optionally substituted with 1 or 2 substituents independently selected from the group consisting of halogen, —OH, —$C_{1-6}$ alkyl, —O—$C_{1-6}$ alkyl, —$CO_2R^a$, —$CO_2(CH_2)_{1-2}R^k$, —$C_{1-6}$ alkyl-$OR^a$, —$R^k$, —$(CH_2)_{1-2}R^k$, —$CH(OR^a)$—$R^k$, and —$CH(N(R^a)_2)$—$R^k$;

(iii) —$(CH_2)_{0-2}$—CH=CH—$(CH_2)_{1-2}$—, which is optionally substituted with 1 or 2 substituents independently selected from the group consisting of halogen, —OH, —$C_{1-6}$ alkyl, and —O—$C_{1-6}$ alkyl; or (iv)

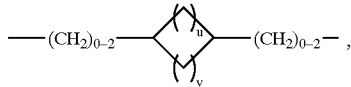

wherein u and v are each integers having a value of from 0 to 4, provided that the sum of u+v is 1, 2, 3 or 4;

$R^5$ is (1) —H, (2) —$C_{1-4}$ alkyl, optionally substituted with from 1 to 3 substituents independently selected from halogen, —O—$C_{1-6}$ alkyl, —O—$C_{1-6}$ fluoroalkyl, —$N(R^a)_2$, and —$CO_2R^a$;

(3) phenyl optionally substituted with from 1 to 5 substituents independently selected from halogen, $C_{1-6}$ alkyl, $C_{1-6}$ fluoroalkyl, —O—$C_{1-6}$ alkyl, —O—$C_{1-6}$ fluoroalkyl, —S—$C_{1-6}$ alkyl, —CN, and —OH, or (4) —$C_{1-4}$ alkyl substituted with $R^k$;

each $R^a$ is independently —H or —$C_{1-6}$ alkyl;

each $R^c$ is independently (1) —H, (2) —$C_{1-4}$ alkyl, (3) —$C_{1-4}$ alkyl substituted with —$N(R^a)_2$, or (4) —$C_{1-4}$ alkyl-phenyl, wherein the phenyl is optionally substituted with 1 to 5 substituents independently selected from halogen, $C_{1-6}$ alkyl, $C_{1-6}$ fluoroalkyl, —O—$C_{1-6}$ alkyl, —O—$C_{1-6}$ fluoroalkyl, —S—$C_{1-6}$ alkyl, —CN, and —OH;

each $R^k$ is independently:

(1) aryl selected from phenyl and naphthyl, wherein aryl is unsubstituted or substituted with from 1 to 5 substituents independently selected:
  (a) halogen,
  (b) $C_{1-6}$ alkyl,
  (c) $C_{1-6}$ fluoroalkyl,
  (d) —O—$C_{1-6}$ alkyl,
  (e) —O—$C_{1-6}$ fluoroalkyl,
  (f) phenyl,
  (g) —S—$C_{1-6}$ alkyl,
  (h) —CN,
  (i) —OH,
  (j) phenyloxy, unsubstituted or substituted with from 1 to 3 substituents independently selected from:
    (i) halogen,
    (ii) $C_{1-6}$ alkyl,
    (iii) $C_{1-6}$ fluoroalkyl, and
    (iv) —OH,
  (k) —$N(R^a)_2$,
  (l) —$C_{1-6}$ alkyl-$N(R^a)_2$,
  (m) —$R^t$,
  (p) —$(CH_2)_{0-3}C(=O)N(R^a)_2$, and
  (q) —$(CH_2)_{0-3}C(=O)R^a$;

(2) —$C_{3-7}$ cycloalkyl, unsubstituted or substituted with from 1 to 3 substituents independently selected from:
  (a) halogen,
  (b) $C_{1-6}$ alkyl,
  (c) —O—$C_{1-6}$ alkyl,
  (d) $C_{1-6}$ fluoroalkyl,
  (e) —O—$C_{1-6}$ fluoroalkyl,
  (f) —CN,
  (h) phenyl, and
  (j) —OH;

(3) —$C_{3-7}$ cycloalkyl fused with a phenyl ring, unsubstituted or substituted with from 1 to 5 substituents independently selected from:
  (a) halogen,
  (b) $C_{1-6}$ alkyl,
  (c) —O—$C_{1-6}$ alkyl,
  (d) $C_{1-6}$ fluoroalkyl,
  (e) —O—$C_{1-6}$ fluoroalkyl,
  (f) —CN, and
  (g) —OH;

(4) a 5- or 6-membered heteroaromatic ring containing from 1 to 4 heteroatoms independently selected from oxygen, nitrogen and sulfur, wherein the heteroaromatic ring is unsubstituted or substituted on nitrogen or carbon with from 1 to 5 substituents independently selected from:
  (a) halogen,
  (b) $C_{1-6}$ alkyl,
  (c) $C_{1-6}$ fluoroalkyl,
  (d) —O—$C_{1-6}$ alkyl,
  (e) —O—$C_{1-6}$ fluoroalkyl,
  (f) phenyl,
  (g) —S—$C_{1-6}$ alkyl,
  (h) —CN,
  (i) —OH,
  (j) phenyloxy, unsubstituted or substituted with from 1 to 3 substituents independently selected from:
    (i) halogen,
    (ii) $C_{1-6}$ alkyl,
    (iii) $C_{1-6}$ fluoroalkyl, and
    (iv) —OH,
  (k) —$N(R^a)_2$,
  (l) —$C_{1-6}$ alkyl-$N(R^a)_2$,
  (m) —$R^t$,
  (n) oxo,
  (o) —$(CH_2)_{0-3}C(=O)N(R^a)_2$, and
  (p) —$(CH_2)_{0-3}C(=O)R^a$;

(5) a 5- or 6-membered saturated heterocyclic ring containing 1 or 2 heteroatoms independently selected from oxygen, nitrogen and sulfur, wherein the heterocyclic ring is unsubstituted or substituted with from 1 to 4 substituents independently selected from:
  (a) halogen,
  (b) $C_{1-6}$ alkyl,
  (c) —O—$C_{1-6}$ alkyl,
  (d) $C_{1-6}$ fluoroalkyl, (e) —O—C$_{1-6}$ fluoroalkyl,
(f) —CN,
(g) oxo,
(h) phenyl
(i) benzyl,
(j) phenylethyl,
(k) —OH,
(l) —(CH$_2$)$_{0-3}$C(=O)N(R$^a$)$_2$,
(m) —(CH$_2$)$_{0-3}$C(=O)R$^a$,
(n) —N(R$^a$)—C(=O)R$^a$,
(o) —N(R$^a$)—C(=O)OR$^a$,
(p) —(CH$_2$)$_{1-3}$N(R$^a$)—C(=O)R$^a$,
(q) —N(R$^a$)$_2$,
(r) —(CH$_2$)$_{1-3}$N(R$^a$)$_2$,
(s) —(CH$_2$)$_{0-3}$C(=O)R$^t$,
(t) —R$^t$,
(u) —N(R$^a$)R$^t$, and
(v) —(CH$_2$)$_{1-3}$R$^t$; or
(6) an 8- to 10-membered heterobicyclic ring containing from 1 to 4 heteroatoms independently selected from oxygen, nitrogen and sulfur, wherein the heterobicyclic ring is saturated or unsaturated, and is unsubstituted or substituted with from 1 to 5 substituents independently selected from:
(a) halogen,
(b) C$_{1-6}$ alkyl,
(c) —O—C$_{1-6}$ alkyl,
(d) C$_{1-6}$ fluoroalkyl,
(e) —O—C$_{1-6}$ fluoroalkyl,
(f) —CN,
(g) =O, and
(h) —OH; and R$^t$ is naphthyl or a 5- or 6-membered heteromonocylic ring containing from 1 to 4 nitrogen atoms, wherein the heteromonocyclic ring is saturated or unsaturated, and wherein the naphthyl or the heteromonocyclic ring is unsubstituted or substituted with 1 or 2 substituents independently selected from halogen, oxo, C$_{1-4}$ alkyl, and —O—C$_{1-4}$ alkyl;
and all other variables are as defined in the first embodiment;
and with the proviso that when Z$^1$ is C—Q$^3$, Z$^2$ is C—Q$^4$, Z$^3$ is CH, and X is C—Q$^1$, then Y is not C—Q$^2$;
or a pharmaceutically acceptable salt thereof.

A third embodiment of the present invention is a compound of Formula I, wherein each R$^k$ is independently:
(1) aryl selected from phenyl and naphthyl, wherein aryl is unsubstituted or substituted with from 1 to 4 substituents independently selected from:
(a) halogen,
(b) C$_{1-6}$ alkyl,
(c) C$_{1-6}$ fluoroalkyl,
(d) —O—C$_{1-6}$ alkyl,
(e) —O—C$_{1-6}$ fluoroalkyl,
(f) phenyl,
(g) —S—C$_{1-6}$ alkyl,
(h) —CN,
(i) —OH,
(j) phenyloxy, unsubstituted or substituted with from 1 to 3 substituents independently selected from:
(i) halogen,
(ii) C$_{1-6}$ alkyl,
(iii) C$_{1-6}$ fluoroalkyl, and
(iv) —OH,
(k) —N(R$^a$)$_2$,
(l) —C$_{1-6}$ alkyl-N(R$^a$)$_2$,
(m) —R$^t$,
(p) —(CH$_2$)$_{0-3}$C(=O)N(R$^a$)$_2$, and
(q) —(CH$_2$)$_{0-3}$C(=O)R$^a$;
(2) —C$_{3-6}$ cycloalkyl, unsubstituted or substituted with from 1 to 3 substituents independently selected from:
(a) halogen,
(b) C$_{1-6}$ alkyl,
(c) —O—C$_{1-6}$ alkyl,
(d) C$_{1-6}$ fluoroalkyl,
(e) —O—C$_{1-6}$ fluoroalkyl,
(f) —CN,
(h) phenyl, and
(j) —OH;
(3) —C$_{3-6}$ cycloalkyl fused with a phenyl ring, unsubstituted or substituted with from 1 to 4 substituents independently selected from:
(a) halogen,
(b) C$_{1-6}$ alkyl,
(c) —O—C$_{1-6}$ alkyl,
(d) C$_{1-6}$ fluoroalkyl,
(e) —O—C$_{1-6}$ fluoroalkyl,
(f) —CN, and
(g) —OH;
(4) a 5- or 6-membered heteroaromatic ring selected from thienyl, pyridyl, imidazolyl, pyrrolyl, pyrazolyl, thiazolyl, isothiazolyl, oxazolyl, isooxazolyl, pyrazinyl, pyrimidinyl, triazolyl, tetrazolyl, furanyl, and pyridazinyl, wherein the heteroaromatic ring is unsubstituted or substituted on nitrogen or carbon with from 1 to 4 substituents independently selected from:
(a) halogen,
(b) C$_{1-6}$ alkyl,
(c) C$_{1-6}$ fluoroalkyl,
(d) —O—C$_{1-6}$ alkyl,
(e) —O—C$_{1-6}$ fluoroalkyl,
(f) phenyl,
(g) —S—C$_{1-6}$ alkyl,
(h) —CN,
(i) —OH,
(j) phenyloxy, unsubstituted or substituted with from 1 to 3 substituents independently selected from:
(i) halogen,
(ii) C$_{1-6}$ alkyl,
(iii) C$_{1-6}$ fluoroalkyl, and
(iv) —OH,
(k) —N(R$^a$)$_2$,
(l) —C$_{1-6}$ alkyl-N(R$^a$)$_2$,
(m) —R$^t$,
(n) oxo,
(o) —(CH$_2$)$_{0-3}$C(=O)N(R$^a$)$_2$, and
(p) —(CH$_2$)$_{0-3}$C(=O)R$^a$;
(5) a 5- or 6-membered saturated heterocyclic ring selected from piperidinyl, morpholinyl, thiomorpholinyl, thiazolidinyl, oxazolidinyl, isooxazolidinyl, isothiazolidinyl, pyrrolidinyl, imidazolidinyl, piperazinyl, tetrahydrofuranyl, and pyrazolidinyl, wherein the heterocyclic ring is unsubstituted or substituted with from 1 to 3 substituents independently selected from:
(a) halogen,
(b) C$_{1-6}$ alkyl,
(c) —O—C$_{1-6}$ alkyl,
(d) C$_{1-6}$ fluoroalkyl,
(e) —O—C$_{1-6}$ fluoroalkyl,
(f) —CN,
(g) =O,
(h) phenyl
(i) benzyl, (j) phenylethyl,
(k) —OH,
(l) —(CH$_2$)$_{0-3}$C(=O)N(R$^a$)$_2$,
(m) —(CH$_2$)$_{0-3}$C(=O)R$^a$,
(n) N(R$^a$)—C(=O)R$^a$,
(o) N(R$^a$)—C(=O)OR$^a$,
(p) (CH$_2$)$_{1-3}$N(R$^a$)—C(=O)R$^a$,
(q) N(R$^a$)$_2$,
(r) (CH$_2$)$_{1-3}$N(R$^a$)$_2$,
(s) —(CH$_2$)$_{0-3}$C(=O)R$^t$,
(t) —R$^t$,
(u) —N(R$^a$)R$^t$, and
(v) —(CH$_2$)$_{1-3}$R$^t$; or (6) an 8- to 10-membered heterobicyclic ring selected from indolyl, benzotriazolyl, benzoimidazolyl, imidazo[4,5-b]pyridinyl, dihydroimidazo[4,5-b]pyridinyl, pyrazolo[4,3-c]pyridinyl, dihydropyrazolo[4,3c]pyridinyl, tetrahydropyrazolo[4,3-c]pyridinyl, pyrrolo[1,2-a]pyrazinyl, dihydropyrrolo[1,2-a]pyrazinyl, tetrahydropyrrolo[1,2-a]pyrazinyl, octahydropyrrolo[1,2-a]pyrazinyl, isoindolyl, indazolyl, indolinyl, isoindolinyl, quinolinyl, isoquinolinyl, quinoxalinyl, quinazolinyl, cinnolinyl, chromanyl, and isochromanyl, wherein the bicyclic ring is unsubstituted or substituted with 1 or 2 substituents independently selected from:
(a) halogen,
(b) C$_{1-6}$ alkyl,
(c) —O—C$_{1-6}$ alkyl,
(d) C$_{1-6}$ fluoroalkyl,
(e) —O—C$_{1-6}$ fluoroalkyl,
(f) —CN,
(g) =O, and
(h) —OH; and R$^t$ is naphthyl or a 5- or 6-membered heteromonocylic ring selected from pyrrolidinyl, pyrazolidinyl, imidazolinyl, piperidinyl, piperazinyl, pyrrolyl, pyridyl, imidazolyl, pyrazolyl, triazolyl, tetrazolyl, pyrazinyl, pyrimidinyl, and pyradizinyl; and wherein the naphthyl or the heteromonocyclic ring is unsubstituted or substituted with 1 or 2 substituents independently selected from halogen, oxo, C$_{1-4}$ alkyl, and —O—C$_{1-4}$ alkyl;

and all other variables are as defined in the second embodiment and with the proviso that when Z$^1$ is C—Q$^3$, Z$^2$ is C—Q$^4$, Z$^3$ is CH, and X is C—Q$^1$, then Y is not C—Q$^2$;
or a pharmaceutically acceptable salt thereof.

A fourth embodiment of the present invention is a compound of Formula I, wherein:

A is
(i) a 5- or 6-membered saturated or unsaturated monocylic heterocycle which contains from 1 to 4 nitrogen atoms, from zero to 2 heteroatoms selected from oxygen and sulfur, and a balance of carbon atoms, with at least one of the ring atoms being carbon;
(ii) a 8- to 11-membered fused bicyclic heterocycle either ring of which is saturated or unsaturated, wherein the fused bicyclic heterocycle contains from 1 to 5 nitrogen atoms, from zero to 3 heteroatoms selected from oxygen and sulfur, and a balance of carbon atoms with at least two of the ring atoms being carbon; or
(iii) a 12- to 14-membered fused tricyclic heterocycle any ring of which is saturated or unsaturated, wherein the fused tricyclic heterocycle contains from 1 to 6 nitrogen atoms, from zero to 3 heteroatoms selected from oxygen and sulfur, and a balance of carbon atoms with at least three of the ring atoms being carbon;

and all other variables are as defined in the second embodiment;
and with the proviso that when Z$^1$ is C—Q$^3$, Z$^2$ is C—Q$^4$, Z$^3$ is CH, and X is C—Q$^1$, then Y is not C—Q$^2$;
or a pharmaceutically acceptable salt thereof.

A fifth embodiment of the present invention is a compound of Formula I, wherein:

A is
(i) a monocyclic heterocycle selected from the group consisting of pyrrolyl, pyrazolyl, imidazolyl, triazolyl, tetrazolyl, pyridyl, pyrazinyl, pyrimidinyl, pyrazidinyl, oxazolyl, isooxazolyl, thiazolyl, isothiazolyl, pyrrolidinyl, pyrazolidinyl, imidazolinyl, piperidinyl, piperazinyl, thiazolidinyl, isothiazolidinyl, and morphonlinyl;
(ii) a fused bicyclic heterocycle selected from the group consisting of indolyl, isoindolyl, phthalazinyl, purinyl, quinoxalinyl, quinazolinyl, cinnolinyl, 1,6-naphthyridinyl, 1,8-napthyridinyl, benzimidazolyl, quinolinyl, isoquinolinyl, indazolyl, dihydroindolyl, dihydroisoindolyl, tetrahydroquinolyl, tetrahydroisoquinolyl, imidazo[1,2-a]pyrimidinyl, 2,3-dihydroimidazo[2, 1b][1,3]thiazolyl, benzazepinyl, dihydrobenazepinyl, benzodiazepinyl, dihydrobenzodiazepinyl, tetrahydrobenzodiazepinyl, and benzothiazolyl; or
(iii) a fused tricyclic heterocycle selected from the group consisting of phenothiazinyl, carbazolyl, beta-carbolinyl, tetrahydro-beta-carbolinyl, acridinyl, phenazinyl, and phenoxazinyl;

and all other variables are as defined in the second embodiment;
and with the proviso that when Z$^1$ is C—Q$^3$, Z$^2$ is C—Q$^4$, Z$^3$ is CH, and X is C—Q$^1$, then Y is not C—Q$^2$;
or a pharmaceutically acceptable salt thereof.

A sixth embodiment of the present invention is a compound of Formula I, wherein:

X is N;
Y is C—Q$^2$;
Z$^1$ is C—Q$^3$;
Z$^2$ is C—Q$^4$;
Z$^3$ is CH;
Q$^2$ is
(1) —H,
(2) —C$_{1-6}$ alkyl,
(3) —C$_{1-6}$ fluoroalkyl,
(4) —O—C$_{1-6}$ alkyl,
(5) —O—C$_{1-6}$ fluoroalkyl,
(6) halo,
(7) —CN,
(8) —C$_{1-6}$ alkyl-OR$^a$,
(9) —C$_{0-6}$ alkyl-C(=O)R$^a$,
(10) —C$_{0-6}$ alkyl-CO$_2$R$^a$,
(11) —C$_{0-6}$ alkyl-SR$^a$,
(12) —N(R$^a$)$_2$,
(13) —C$_{1-6}$ alkyl —N(R$^a$)$_2$,
(14) —C$_{0-6}$ alkyl-C(=O)N(R$^a$)$_2$,
(15) —C$_{1-6}$ alkyl-N(R$^a$)—C(R$^a$)=O,
(16) —SO$_2$R$^a$,
(17) —N(R$^a$)SO$_2$R$^a$,

(18) —$C_{2-5}$ alkynyl,
(19) —$C_{2-5}$ alkynyl-$CH_2N(R^a)_2$,
(20) —$C_{2-5}$ alkynyl-$CH_2OR^a$,
(21)

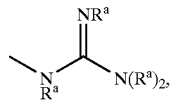

(22) —$N(R^a)$—$C_{1-6}$ alkyl-$SR^a$,
(23) —$N(R^a)$—$C_{1-6}$ alkyl-$OR^a$,
(24) —$N(R^a)$—$C_{1-6}$ alkyl-$N(R^a)_2$,
(25) —$N(R^a)$—$C_{1-6}$ alkyl-$N(R^a)$—$C(R^a)$=O,
(26) —$R^k$,
(27) —$C_{1-6}$ alkyl substituted with $R^k$,
(28) —$C_{1-6}$ fluoroalkyl substituted with $R^k$,
(29) —$C_{2-5}$ alkenyl-$R^k$,
(30) —$C_{2-5}$ alkynyl-$R^k$,
(31) —O-$R^k$,
(32) —O—$C_{1-4}$ alkyl-$R^k$,
(33) —$S(O)_n$—$R^k$,
(34) —$S(O)_n$—$C_{1-4}$ alkyl-$R^k$,
(35) —O—$C_{1-6}$ alkyl-$OR^k$,
(36) —O—$C_{1-6}$ alkyl-O—$C_{1-4}$ alkyl-$R^k$,
(37) —O—$C_{1-6}$ alkyl-$SR^k$,
(39) —$N(R^c)$—$C_{1-6}$ alkyl substituted with one or two $R^k$ groups,
(40) —$N(R^c)$—$C_{1-6}$ alkyl-$OR^k$,
(41) —C(=O)N—$C_{1-6}$ alkyl-$R^k$,
(42) —$C_{2-5}$ alkynyl-$CH_2S(O)_n$—$R^a$, or
(43) —C(=$NR^a$)—$N(R^a)_2$;
each of $Q^3$ and $Q^4$ is independently:
(1) —H,
(2) —$C_{1-6}$ alkyl,
(3) —$C_{1-6}$ fluoroalkyl,
(4) —O—$C_{1-6}$ alkyl,
(5) —O—$C_{1-6}$ fluoroalkyl,
(6) halo,
(7) —CN,
(8) —$C_{1-6}$ alkyl-$OR^a$,
(9) —$C_{0-6}$ alkyl-C(=O)$R^a$,
(10) —$C_{0-6}$ alkyl-$CO_2R^a$,
(11) —$SR^a$,
(12) —$N(R^a)_2$,
(13) —$C_{1-6}$ alkyl —$N(R^a)_2$,
(14) —$C_{0-6}$ alkyl-C(=O)$N(R^a)_2$,
(15) —$SO_2R^a$,
(16) —$N(R^a)SO_2R^a$;
(17) —$R^k$, or
(18) —$C_{1-6}$ alkyl substituted with $R^k$;
and all other variables are as originally defined;
or a pharmaceutically acceptable salt thereof.

A seventh embodiment is identical to the sixth embodiment, except that all other variables are as defined in the first embodiment, instead of being as originally defined.

An eighth embodiment of the present invention is a compound of Formula I, wherein:

$Q^3$ is:
(1) —H,
(2) —$C_{1-6}$ alkyl,
(3) —$C_{1-6}$ fluoroalkyl,
(4) —O—$C_{1-6}$ alkyl,
(5) —O—$C_{1-6}$ fluoroalkyl,
(6) halo,
(7) —CN,
(8) —$C_{1-6}$ alkyl-$OR^a$,
(9) —$C_{0-6}$ alkyl-C(=O)$R^a$,
(10) —$C_{0-6}$ alkyl-$CO_2R^a$,
(11) —$SR^a$,
(12) —$N(R^a)_2$,
(13) —$C_{1-6}$ alkyl —$N(R^a)_2$,
(14) —$C_{0-6}$ alkyl-C(=O)$N(R^a)_2$,
(15) —$SO_2R^a$,
(16) —$N(R^a)SO_2R^a$;
(17) —$R^k$, or
(18) —$C_{1-6}$ alkyl substituted with $R^k$;
$Q^4$ is:
(1) —H,
(2) —$C_{1-6}$ alkyl,
(3) —$C_{1-6}$ fluoroalkyl,
(4) —O—$C_{1-6}$ alkyl,
(5) —O—$C_{1-6}$ fluoroalkyl,
(6) halo,
(7) —CN,
(8) —$C_{1-6}$ alkyl-$OR^a$,
(9) —$C_{0-6}$ alkyl-C(=O)$R^a$,
(10) —$C_{0-6}$ alkyl-$CO_2R^a$,
(11) —$SR^a$,
(12) —$N(R^a)_2$,
(13) —$C_{1-6}$ alkyl-$N(R^a)_2$,
(14) —$C_{0-6}$ alkyl-C(=O)$N(R^a)_2$,
(15) —$SO_2R^a$, or
(16) —$N(R^a)SO_2R^a$;
and all other variables are as defined in the seventh embodiment;
or a pharmaceutically acceptable salt thereof.

In an aspect of each of the sixth, seventh and eighth embodiments, $Q^3$ and $Q^4$ are both —H.

A ninth embodiment of the present invention is a compound of Formula (II):

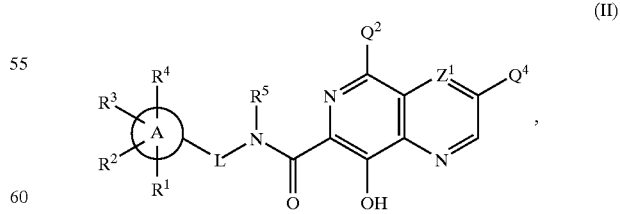

(II)

wherein

A is (i) a 4- to 7-membered saturated or unsaturated monocylic heterocycle which contains from 1 to 4 nitrogen atoms, from zero to 2 heteroatoms selected from oxygen and sulfur, and a balance of carbon atoms, with at least one of the ring atoms being carbon;

(ii) a 7- to 11-membered fused bicyclic heterocycle either ring of which is saturated or unsaturated, wherein the fused bicyclic heterocycle contains from 1 to 6 heteroatoms selected from nitrogen, oxygen and sulfur, and a balance of carbon atoms with at least two of the ring atoms being carbon; or (iii) a 11- to 15-membered fused tricyclic heterocycle any ring of which is saturated or unsaturated, wherein the fused tricyclic heterocycle contains from 1 to 6 nitrogen atoms, from zero to 3 heteroatoms selected from oxygen and sulfur, and a balance of carbon atoms with at least three of the ring atoms being carbon;

L is
(i) a single bond;
(ii) —$(CH_2)_{1-3}$—, which is optionally substituted with 1 or 2 substituents independently selected from the group consisting of —OH, —$C_{1-4}$ alkyl, —O—$C_{1-4}$ alkyl, —$CO_2CH_3$, —$CO_2CH_2$-phenyl, phenyl, benzyl, —$(CH_2)_{1-2}OH$, —CH(OH)-phenyl, and —$CH(NH_2)$-phenyl;
(iii) —$(CH_2)_{0-1}$—CH=CH—$(CH_2)$—, which is optionally substituted with 1 or 2 substituents independently selected from the group consisting of halogen, —OH, —$C_{1-4}$ alkyl, and —O—$C_{1-4}$ alkyl; or
(iv)

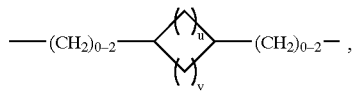

wherein u and v are each integers having a value of from 0 to 4, provided that the sum of u+v is 1, 2, 3 or 4;

$Z^1$ is N or C—$Q^3$;

$Q^2$ is
(1) —H,
(2) —$C_{1-4}$ alkyl,
(3) —$C_{1-4}$ fluoroalkyl,
(4) —O—$C_{1-4}$ alkyl,
(5) —O—$C_{1-4}$ fluoroalkyl,
(6) halo,
(7) —CN,
(8) —$C_{1-4}$ alkyl-$OR^a$,
(9) —$(CH_2)_{0-2}C(=O)R^a$,
(10) —$(CH_2)_{0-2}CO_2R^a$,
(11) —$(CH_2)_{0-2}SR^a$,
(12) —$N(R^a)_2$,
(13) —$C_{1-4}$ alkyl —$N(R^a)_2$,
(14) —$(CH_2)_{0-2}C(=O)N(R^a)_2$,
(15) —$SO_2R^a$,
(16) —$N(R^a)SO_2R^a$,
(17) —$C_{2-3}$ alkynyl,
(18) —C≡C—$CH_2N(R^a)_2$
(19) —C≡C—$CH_2OR^a$
(20) —$N(R^a)$—$C_{1-4}$alkyl-$SR^a$,
(21) —$N(R^a)$—$C_{1-4}$ alkyl-$OR^a$,
(22) —$N(R^a)$—$C_{1-4}$ alkyl-$N(R^a)_2$,
(23) —$N(R^a)$—$C_{1-4}$ alkyl-$N(R^a)$—$C(R^a)$=O,
(24) —$R^k$,
(25) —$C_{1-4}$ alkyl substituted with $R^k$,
(26) —$C_{1-4}$ fluoroalkyl substituted with $R^k$,
(27) —$C_{2-5}$ alkenyl-$R^k$,
(28) —$C_{2-5}$ alkynyl-$R^k$,
(29) —O-$R^k$,
(30) —O—$C_{1-4}$ alkyl-$R^k$,
(31) —$S(O)_n$—$R^k$,
(32) —$N(R^c)$—$R^k$,
(33) —$N(R^c)$—$C_{1-4}$ alkyl substituted with one or two $R^k$ groups,
(34) —$N(R^c)$—$C_{1-4}$ alkyl-$OR^k$,
(35) —C(=O)N—$C_{1-4}$ alkyl-$R^k$,
(36) —C≡C—$CH_2SR^a$, or
(37) C—C—$CH_2SO_2R^a$;

$Q^3$ is
(1) —H,
(2) —$C_{1-4}$ alkyl,
(3) —$C_{1-4}$ fluoroalkyl,
(4) —O—$C_{1-14}$ alkyl,
(5) —O—$C_{1-4}$ fluoroalkyl,
(6) halo selected from —F, —Cl, and —Br,
(7) —CN,
(8) —$C_{1-4}$ alkyl-$OR^a$, or
(9) —$C_{1-4}$ alkyl substituted with $R^k$;

$Q^4$ is:
(1) —H,
(2) —$C_{1-4}$ alkyl,
(3) —$C_{1-4}$ fluoroalkyl,
(4) —O—$C_{1-4}$ alkyl,
(5) —O—$C_{1-4}$ fluoroalkyl,
(6) halo selected from —F, —Cl, and —Br,
(7) —CN,
(8) —$C_{1-6}$ alkyl-$OR^a$,
(9) —$N(R^a)_2$, or
(10) —$C_{1-6}$ alkyl —$N(R^a)_2$;

each of $R^1$ and $R^2$ is independently:
(1) —H,
(2) —$C_{1-4}$ alkyl,
(3) —$C_{1-4}$ fluoroalkyl,
(4) —O—$C_{1-4}$ alkyl,
(5) —O—$C_{1-4}$ fluoroalkyl,
(6) —OH,
(7) halo,
(8) —CN,
(9) —$C_{1-4}$ alkyl-$OR^a$,
(10) —$(CH_2)_{0-2}C(=O)R^a$,
(11) —$(CH_2)_{0-2}CO_2R^a$,
(12) —$(CH_2)_{0-2}SR^a$,
(13) —$N(R^a)_2$,
(14) —$C_{1-4}$ alkyl $N(R^a)_2$,
(15) —$(CH_2)_{0-2}C(=O)N(R^a)_2$,
(16) —$C_{1-4}$ alkyl-$N(R^a)$—$C(R^a)$=O,
(17) —$SO_2R^a$,
(18) —$N(R^a)SO_2R^a$,
(19) —O—$C_{1-4}$ alkyl-$OR^a$,
(20) —O—$C_{1-4}$ alkyl-$SR^a$,

(21) —O-C$_{1-4}$ alkyl-NH—CO$_2$R$^a$,
(22) —O—C$_{2-4}$ alkyl-N(R$^a$)$_2$,
(23) —N(R$^a$)—C$_{1-4}$ alkyl-SR$^a$,
(24) —N(R$^a$)—C$_{1-4}$ alkyl-OR$^a$,
(25) —N(R$^a$)—C$_{1-4}$ alkyl-N(R$^a$)$_2$,
(26) —N(R$^a$)—C$_{1-4}$ alkyl-N(R$^a$)—C(R$^a$)=O,
(27) —R$^k$,
(28) —C$_{1-4}$ alkyl substituted with 1 or 2 R$^k$ groups,
(29) —C$_{1-4}$ fluoroalkyl substituted with 1 or 2 R$^k$ groups,
(30) —O—R$^k$,
(31) —O—C$_{1-4}$ alkyl-R$^k$,
(32) —S(O)$_n$—R$^k$,
(33) —S(O)$_n$-C$_{1-4}$ alkyl-R$^k$,
(34) —O—C$_{1-4}$ alkyl-OR$^k$,
(35) —O—C$_{1-4}$ alkyl-O—C$_{1-4}$ alkyl-R$^k$,
(36) —O—C$_{1-4}$ alkyl-SR$^k$, or
(37) —C$_{0-4}$ alkyl-N(R$^b$)(R$^k$);

each of R$^3$ and R$^4$ is independently
(1) —H,
(2) halo,
(3) —CN,
(4) —OH,
(5) C$_{1-4}$ alkyl,
(6) C$_{1-4}$ fluoroalkyl,
(7) —O—C$_{1-4}$ alkyl,
(8) —O—C$_{1-4}$ fluoroalkyl,
(9) —C$_{1-4}$ alkyl-OR$^a$,
(10) —O—C$_{1-4}$ alkyl-OR$^a$,
(11) —O—C$_{1-4}$ alkyl-SR$^a$,
(12) —O—C$_{1-4}$ alkyl-NH—CO$_2$R$^a$, or
(13) —O—C$_{2-4}$ alkyl-N(R$^a$)$_2$;

R$^5$ is
(1) —H,
(2) —C$_{1-4}$ alkyl, optionally substituted with 1 or 2 substituents independently selected from halogen, —O—C$_{1-4}$ alkyl, —O—C$_{1-4}$ fluoroalkyl, —N(R$^a$)$_2$, and —C$_{0-2}$R$^a$;
(3) phenyl optionally substituted with from 1 to 3 substituents independently selected from halogen, C$_{1-4}$ alkyl, C$_{1-4}$ fluoroalkyl, —O—C$_{1-4}$ alkyl, —O—C$_{1-4}$ fluoroalkyl, —S—C$_{1-4}$ alkyl, —CN, and —OH, or
(4) —C$_{1-4}$ alkyl substituted with phenyl;

each R$^a$ is independently —H or —C$_{1-4}$ alkyl;

each R$^b$ is independently:
(1) —H,
(2) —C$_{1-4}$ alkyl,
(3) —C$_{1-4}$ fluoroalkyl,
(4) —R$^k$,
(5) —C$_{1-4}$ alkyl-R$^k$,
(6) —S(O)$_n$—R$^k$, or
(7) —C(=O)-R$^k$;

each R$^c$ is independently
(1) —H,
(2) —C$_{1-4}$ alkyl,
(3) —C$_{1-4}$ alkyl substituted with —N(R$^a$)$_2$, or
(4) —C$_{1-4}$ alkyl-phenyl, wherein the phenyl is optionally substituted with 1 to 3 substituents independently selected from halogen, C$_{1-4}$ alkyl, C$_{1-4}$ fluoroalkyl, —O—C$_{1-4}$ alkyl, —O—C$_{1-4}$ fluoroalkyl, —S—C$_{1-4}$ alkyl, —CN, and —OH;

each R$^k$ is independently:
(1) aryl selected from phenyl and naphthyl, wherein aryl is unsubstituted or substituted with from 1 to 5 substituents independently selected from:
(a) halogen,
(b) C$_{1-6}$ alkyl,
(c) C$_{1-6}$ fluoroalkyl,
(d) —O—C$_{1-6}$ alkyl,
(e) —O—C$_{1-6}$ fluoroalkyl,
(f) phenyl,
(g) —S—C$_{1-6}$ alkyl,
(h) —CN,
(i) —OH,
(j) phenyloxy, unsubstituted or substituted with from 1 to 3 substituents independently selected from:
(i) halogen,
(ii) C$_{1-6}$ alkyl,
(iii) C$_{1-6}$ fluoroalkyl, and
(iv) —OH,
(k) —N(R$^a$)$_2$,
(l) —C$_{1-6}$ alkyl-N(R$^a$)$_2$,
(m) —R$^t$,
(p) —(CH$_2$)$_{0-3}$C(=O)N(R$^a$)$_2$, and
(q) —(CH$_2$)$_{0-3}$C(=O)R$^a$;
(2) —C$_{3-7}$ cycloalkyl, unsubstituted or substituted with from 1 to 3 substituents independently selected from:
(a) halogen,
(b) C$_{1-6}$ alkyl,
(c) —O—C$_{1-6}$ alkyl,
(d) C$_{1-6}$ fluoroalkyl,
(e) —O—C$_{1-6}$ fluoroalkyl,
(f) —CN,
(h) phenyl, and
(j) —OH;
(3) —C$_{3-7}$ cycloalkyl fused with a phenyl ring, unsubstituted or substituted with from 1 to 5 substituents independently selected from:
(a) halogen,
(b) C$_{1-6}$ alkyl,
(c) —O—C$_{1-6}$ alkyl,
(d) C$_{1-6}$ fluoroalkyl,
(e) —O—C$_{1-6}$ fluoroalkyl,
(f) —CN, and
(g) —OH;
(4) a 5- or 6-membered heteroaromatic ring containing from 1 to 4 heteroatoms independently selected from oxygen, nitrogen and sulfur, wherein the heteroaromatic ring is unsubstituted or substituted on nitrogen or carbon with from 1 to 5 substituents independently selected from:
(a) halogen,
(b) C$_{1-6}$ alkyl,
(c) C$_{1-6}$ fluoroalkyl,
(d) —O—C$_{1-6}$ alkyl,
(e) —O—C$_{1-6}$ fluoroalkyl,
(f) phenyl,
(g) —S—C$_{1-6}$ alkyl,
(h) —CN,
(i) —OH,
(j) phenyloxy, unsubstituted or substituted with from 1 to 3 substituents independently selected from:
(i) halogen,
(ii) C$_{1-6}$ alkyl,
(iii) C$_{1-6}$ fluoroalkyl, and
(iv) —OH,
(k) —N(R$^a$)$_2$,
(l) —C$_{1-6}$ alkyl-N(R$^a$)$_2$, (m) —$R^t$,
(n) oxo,
(o) —$(CH_2)_{0-3}C(=O)N(R^a)_2$, and
(p) —$(CH_2)_{0-3}C(=O)R^a$;
(5) a 5- or 6-membered saturated heterocyclic ring containing 1 or 2 heteroatoms independently selected from oxygen, nitrogen and sulfur, wherein the heterocyclic ring is unsubstituted or substituted with from 1 to 4 substituents independently selected from:
(a) halogen,
(b) $C_{1-6}$ alkyl,
(c) —O—$C_{1-6}$ alkyl,
(d) $C_{1-6}$ fluoroalkyl,
(e) —O—$C_{1-6}$ fluoroalkyl,
(f) —CN,
(g) oxo,
(h) phenyl,
(i) benzyl,
(j) phenylethyl,
(k) —OH,
(l) —$(CH_2)_{0-3}C(=O)N(R^a)_2$,
(m) —$(CH_2)_{0-3}C(=O)R^a$,
(n) —$N(R^a)$—$C(=O)R^a$,
(o) —$N(R^a)$—$C(=O)OR^a$,
(p) —$(CH_2)_{1-3}N(R^a)$—$C(=O)R^a$,
(q) —$N(R^a)_2$,
(r) —$(CH_2)_{1-3}N(R^a)_2$,
(s) —$(CH_2)_{0-3}C(=O)R^t$,
(t) —$R^t$,
(u) —$N(R^a)R^t$, and
(v) —$(CH_2)_{1-3}R^t$; or
(6) an 8- to 10-membered heterobicyclic ring containing from 1 to 4 heteroatoms independently selected from oxygen, nitrogen and sulfur, wherein the heterobicyclic ring is saturated or unsaturated, and is unsubstituted or substituted with from 1 to 5 substituents independently selected from:
(a) halogen,
(b) $C_{1-6}$ alkyl,
(c) —O—$C_{1-6}$ alkyl,
(d) $C_{1-6}$ fluoroalkyl,
(e) —O—$C_{1-6}$ fluoroalkyl,
(f) —CN,
(g) =O, and
(h) —OH;
$R^t$ is naphthyl or a 5- or 6-membered heteromonocylic ring containing from 1 to 4 nitrogen atoms, wherein the heteromonocyclic ring is saturated or unsaturated, and wherein the naphthyl or the heteromonocyclic ring is unsubstituted or substituted with 1 or 2 substituents independently selected from halogen, oxo, $C_{1-4}$ alkyl, and —O—$C_{1-4}$ alkyl; and
n is an integer equal to 0, 1 or 2;
or a pharmaceutically acceptable salt thereof.

A tenth embodiment of the present invention is a compound of Formula II, wherein $Z^1$ is CH;
$Q^2$ is
(1) —H,
(2) —$C_{1-4}$ alkyl,
(3) —$(CH_2)_{0-2}CF_3$,
(4) —O—$C_{1-4}$ alkyl,
(5) —O—$(CH_2)_{0-2}CF_3$,
(6) halo selected from —F, —Cl and —Br,
(7) —CN,
(8) —$(CH_2)_{1-3}OR^a$,
(9) —$(CH_2)_{0-2}C(=O)R^a$,
(10) —$(CH_2)_{0-2}CO_2R^a$,
(11) —$(CH_2)_{0-2}SR^a$,
(12) —$N(R^a)_2$,
(13) —$(CH_2)_{1-3}N(R^a)_2$,
(14) —$(CH_2)_{0-2}C(=O)N(R^a)_2$,
(15) —$SO_2R^a$,
(16) —$N(R^a)SO_2R^a$,
(17) —C≡C—$CH_2OR^a$
(18) —$N(R^a)$—$(CH_2)_{1-4}SR^a$,
(19) —$N(R^a)$—$(CH_2)_{1-4}OR^a$,
(20) —$N(R^a)$—$(CH_2)_{1-4}$—$N(R^a)_2$,
(21) —$N(R^a)$—$(CH_2)_{1-4}N(R^a)$—$C(R^a)=O$,
(22) —$R^k$,
(23) —$(CH_2)_1R^k$,
(24) —C≡C—$CH_2R^k$,
(25) —O—$R^k$,
(26) —$S(O)_n$—$R^k$,
(27) —$N(R^c)$—$R^k$,
(28) —$N(R^c)$—$(CH_2)_{1-4}H$ substituted with one or two $R^k$ groups,
(29) —$N(R^c)$—$(CH_2)_{1-4}OR^k$,
(30) —$C(=O)N$—$(CH_2)_{1-4}R^k$,
(31) —C≡C—$CH_2SR^a$, or
(32) —C≡C—$CH_2SO_2R^a$;
$Q^4$ is —H;
each of $R^1$ and $R^2$ is independently:
(1) —H,
(2) —$C_{1-4}$ alkyl,
(3) —$(CH_2)_{0-2}CF_3$,
(4) —O—$C_{1-4}$ alkyl,
(5) —O—$(CH_2)_{0-2}CF_3$,
(6) —OH,
(7) halo selected from —F, —Cl and —Br,
(8) —CN,
(9) —$(CH_2)_{1-3}OR^a$,
(10) —$(CH_2)_{0-2}C(=O)R^a$,
(11) —$(CH_2)_{0-2}CO_2R^a$,
(12) —$(CH_2)_{0-2}SR^a$,
(13) —$N(R^a)_2$,
(14) —$(CH_2)_{1-3}N(R^a)_2$,
(15) —$(CH_2)_{0-2}C(=O)N(R^a)_2$,
(16) —$C_{1-4}$ alkyl-$N(R^a)$—$C(R^a)=O$,
(17) —$SO_2R^a$,
(18) —$N(R^a)SO_2R^a$,
(19) —O—$(CH_2)_{1-4}OR^a$,
(20) —O—$(CH_2)_{1-4}SR^a$,
(21) —O—$(CH_2)_{1-4}NH$—$CO_2R^a$,
(22) —O—$(CH_2)_{2-4}N(R^a)_2$,
(23) —$N(R^a)$—$(CH_2)_{1-4}SR^a$,
(24) —$N(R^a)$—$(CH_2)_{1-4}OR^a$,
(25) —$N(R^a)$—$(CH_2)_{1-4}N(R^a)_2$,
(26) —$N(R^a)$—$(CH_2)_{1-4}N(R^a)$—$C(R^a)=O$,
(27) —$R^k$,
(28) —$(CH_2)_{1-4}H$ substituted with 1 or 2 $R^k$ groups,

(29) —O—$R^k$,
(30) —O—$(CH_2)_{1-4}R^k$,
(31) —S(O)$_n$—$R^k$,
(32) —S(O)$_n$—$(CH_2)_{1-4}R^k$,
(33) —O—$(CH_2)_{1-4}OR^k$,
(34) —O—$(CH_2)_{1-4}$—O—$(CH_2)_{1-4}R^k$,
(35) —O—$(CH_2)_{1-4}SR^k$, or
(36) —$(CH_2)_{0-4}N(R^b)(R^k)$;

each of $R^3$ and $R^4$ is independently
(1) —H,
(2) halo selected from —F, —Cl and —Br,
(3) —CN,
(4) —OH,
(5) $C_{1-4}$ alkyl,
(6) —$(CH_2)_{0-2}CF_3$,
(7) —O—$C_{1-4}$ alkyl, or
(8) —$O(CH_2)_{0-2}CF_3$, $R^5$ is
(1) —H.
(2) —$C_{1-4}$ alkyl,
(3) —$(CH_2)_{1-4}N(R^a)_2$,
(4) —$(CH_2)_{1-4}CO_2R^a$,
(5) phenyl optionally substituted with from 1 to 3 substituents independently selected from halogen, $C_{1-4}$ alkyl, —$(CH_2)_{0-2}CF_3$, —O—$C_{1-4}$ alkyl, —$O(CH_2)_{0-2}CF_3$, —S—$C_{1-4}$ alkyl, —CN, and —OH, or
(6) —$(CH_2)_{1-4}$-phenyl;

each $R^a$ is independently —H or —$C_{1-4}$ alkyl;
each $R^b$ is independently:
(1) —H,
(2) —$C_{1-4}$ alkyl,
(3) —$CF_3$,
(4) —$R^k$, or
(5) —$(CH_2)_{1-4}$—$R^k$;

each $R^c$ is independently
(1) —H,
(2) —$C_{1-4}$ alkyl,
(3) —$(CH_2)_{1-4}N(R^a)_2$, or
(4) —$(CH_2)_{1-4}$-phenyl, wherein the phenyl is optionally substituted with 1 to 3 substituents independently selected from halogen, $C_{1-4}$ alkyl, $C_{1-4}$ fluoroalkyl, —O—$C_{1-4}$ alkyl, —O—$C_{1-4}$ fluoroalkyl, —S—$C_{1-4}$ alkyl, —CN, and —OH; and each $R^k$ is independently:
(1) aryl selected from phenyl and naphthyl, wherein aryl is unsubstituted or substituted with from 1 to 4 substituents independently selected from:
(a) halogen,
(b) $C_{1-4}$ alkyl,
(c) $C_{1-4}$ fluoroalkyl,
(d) —O—$C_{1-4}$ alkyl,
(e) —O—$C_{1-4}$ fluoroalkyl,
(f) phenyl,
(g) —S—$C_{1-4}$ alkyl,
(h) —CN,
(i) —OH,
(j) phenyloxy, unsubstituted or substituted with from 1 to 3 substituents independently selected from:
(i) halogen,
(ii) $C_{1-4}$ alkyl,
(iii) $C_{1-4}$ fluoroalkyl, and
(iv) —OH,
(k) —$N(R^a)_2$,
(l) —$C_{1-4}$ alkyl-$N(R^a)_2$,
(m) —$R^t$,
(p) —$(CH_2)_{0-3}C(=O)N(R^a)_2$, and
(q) —$(CH_2)_{0-3}C(=O)R^a$;

(2) —$C_{3-6}$ cycloalkyl, unsubstituted or substituted with from 1 to 3 substituents independently selected from:
(a) halogen,
(b) $C_{1-4}$ alkyl,
(c) —O—$C_{1-4}$ alkyl,
(d) $C_{1-4}$ fluoroalkyl,
(e) —O—$C_{1-4}$ fluoroalkyl,
(f) —CN,
(h) phenyl, and
(j) —OH;

(3) —$C_{3-6}$ cycloalkyl fused with a phenyl ring, unsubstituted or substituted with from 1 to 4 substituents independently selected from:
(a) halogen,
(b) $C_{1-4}$ alkyl,
(c) —O—$C_{1-4}$ alkyl,
(d) $C_{1-4}$ fluoroalkyl,
(e) —O—$C_{1-4}$ fluoroalkyl,
(f) —CN, and
(g) —OH;

(4) a 5- or 6-membered heteroaromatic ring selected from thienyl, pyridyl, imidazolyl, pyrrolyl, pyrazolyl, thiazolyl, isothiazolyl, oxazolyl, isooxazolyl, pyrazinyl, pyrimidinyl, triazolyl, tetrazolyl, furanyl, and pyridazinyl, wherein the heteroaromatic ring is unsubstituted or substituted on nitrogen or carbon with from 1 to 4 substituents independently selected from:
(a) halogen,
(b) $C_{1-4}$ alkyl,
(c) $C_{1-4}$ fluoroalkyl,
(d) —O—$C_{1-4}$ alkyl,
(e) —O—$C_{1-4}$ fluoroalkyl,
(f) phenyl,
(g) —S—$C_{1-4}$ alkyl,
(h) —CN,
(i) —OH,
(j) phenyloxy, unsubstituted or substituted with from 1 to 3 substituents independently selected from:
(i) halogen,
(ii) $C_{1-4}$ alkyl,
(iii) $C_{1-4}$ fluoroalkyl, and
(iv) —OH,
(k) —$N(R^a)_2$,
(l) —$C_{1-4}$ alkyl-$N(R^a)_2$,
(m) —$R^t$,
(n) oxo,
(o) —$(CH_2)_{0-3}C(=O)N(R^a)_2$, and
(p) —$(CH_2)_{0-3}C(=O)R^a$;

(5) a 5- or 6-membered saturated heterocyclic ring selected from piperidinyl, morpholinyl, thiomorpholinyl, thiazolidinyl, isothiazolidinyl, oxazolidinyl, isooxazolidinyl, pyrrolidinyl, imidazolidinyl, piperazinyl, tetrahydrofuranyl, and pyrazolidinyl, wherein the heterocyclic ring is unsubstituted or substituted with from 1 to 3 substituents independently selected from:
(a) halogen,
(b) $C_{1-4}$ alkyl,
(c) —O—$C_{1-4}$ alkyl,
(d) $C_{1-4}$ fluoroalkyl,
(e) —O—$C_{1-4}$ fluoroalkyl, (f) —CN,
(g) =O,
(h) phenyl,
(i) benzyl,
(j) phenylethyl,
(k) —OH,
(l) —(CH$_2$)$_{0-3}$C(=O)N(R$^a$)$_2$,
(m) —(CH$_2$)$_{0-3}$C(=O)R$^a$,
(n) N(R$^a$)—C(=O)R$^a$,
(o) N(R$^a$)—C(=O)OR$^a$,
(p) (CH$_2$)$_{1-3}$N(R$^a$)—C(=O)R$^a$,
(q) N(R$^a$)$_2$,
(r) (CH$_2$))$_{1-3}$N(R$^a$)$_2$,
(s) —(CH$_2$)$_{0-3}$C(=O)R$^t$,
(t) —R$^t$,
(u) —N(R$^a$)R$^t$, and
(v) —(CH$_2$)$_{1-3}$R$^t$; or (6) an 8- to 10-membered heterobicyclic ring selected from indolyl, benzotriazolyl, benzoimidazolyl, imidazo[4,5-b]pyridinyl, dihydroimidazo[4,5-b]pyridinyl, pyrazolo[4,3-c]pyridinyl, dihydropyrazolo[4,3c]pyridinyl, tetrahydropyrazolo[4,3-c]pyridinyl, pyrrolo[1,2-a]pyrazinyl, dihydropyrrolo[1,2-a]pyrazinyl, tetrahydropyrrolo[1,2-a]pyrazinyl, octahydropyrrolo[1,2-a]pyrazinyl, isoindolyl, indazolyl, indolinyl, isoindolinyl, quinolinyl, isoquinolinyl, quinoxalinyl, quinazolinyl, cinnolinyl, chromanyl, and isochromanyl, wherein the bicyclic ring is unsubstituted or substituted with 1 or 2 substituents independently selected from:
(a) halogen,
(b) C$_{1-4}$ alkyl,
(c) —O—C$_{1-4}$ alkyl,
(d) C$_{1-4}$ fluoroalkyl,
(e) —O—C$_{1-4}$ fluoroalkyl,
(f) —CN,
(g) =O, and
(h) —OH;

R$^t$ is naphthyl or a 5- or 6-membered heteromonocylic ring selected from pyrrolidinyl, pyrazolidinyl, imidazolinyl, piperidinyl, piperazinyl, pyrrolyl, pyridyl, imidazolyl, pyrazolyl, triazolyl, tetrazolyl, pyrazinyl, pyrimidinyl, and pyradizinyl;

and wherein the naphthyl or the heteromonocyclic ring is unsubstituted or substituted with 1 or 2 substituents independently selected from halogen, oxo, C$_{1-4}$ alkyl, and —O—C$_{1-4}$ alkyl;

and all other variables are as defined in the ninth embodiment;

or a pharmaceutically acceptable salt thereof.

A first class of the present invention is compounds of Formula (III)

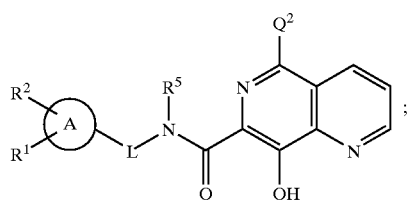

(III)

wherein

A is
(i) a 4- to 7-membered saturated or unsaturated monocylic heterocycle which contains from 1 to 4 nitrogen atoms, from zero to 2 heteroatoms selected from oxygen and sulfur, and a balance of carbon atoms, with at least one of the ring atoms being carbon;
(ii) a 7- to 11-membered fused bicyclic heterocycle either ring of which is saturated or unsaturated, wherein the fused bicyclic heterocycle contains from 1 to 6 heteroatoms selected from nitrogen, oxygen and sulfur, and a balance of carbon atoms with at least two of the ring atoms being carbon; or
(iii) a 11- to 15-membered fused tricyclic heterocycle any ring of which is saturated or unsaturated, wherein the fused tricyclic heterocycle contains from 1 to 6 nitrogen atoms, from zero to 3 heteroatoms selected from oxygen and sulfur, and a balance of carbon atoms with at least three of the ring atoms being carbon;

L is
(i) a single bond; or
(ii) —(CH$_2$)$_{1-3}$—, which is optionally substituted with 1 or 2 substituents independently selected from the group consisting of —OH, methyl, ethyl, —CO$_2$CH$_3$, —CO$_2$CH$_2$-phenyl, phenyl, benzyl, —(CH$_2$)$_{1-2}$OH, —CH(OH)-phenyl, and —CH(NH$_2$)-phenyl;

Q$^2$ is
(1) —H,
(2) methyl,
(3) ethyl,
(4) CF$_3$,
(5) methoxy,
(6) ethoxy
(7) —OCF$_3$
(8) halo selected from —F, —Cl and —Br,
(9) —CN,
(10) —CH$_2$OH,
(11) —CH$_2$OCH$_3$
(12) —(CH$_2$)$_{0-2}$CO$_2$CH$_3$,
(13) —SR$^a$,
(14) —N(R$^a$)$_2$,
(15) —SO$_2$R$^a$,
(16) —C≡C—CH$_2$OR$^a$
(17) —N(R$^a$)—(CH$_2$)$_{1-3}$SR$^a$,
(18) —N(R$^a$)—(CH$_2$)$_{1-3}$OR$^a$,
(19) —N(R$^a$)—(CH$_2$)$_{1-3}$N(R$^a$)$_2$,
(20) —N(R$^a$)—(CH$_2$)$_{1-3}$N(R$^a$)—C(R$^a$)=O,
(21) —R$^k$,
(22) —(CH$_2$)$_{1-4}$R$^k$,
(23) —C≡C—CH$_2$R$^k$,
(24) —O—R$^k$,
(25) —S—R$^k$,
(26) —SO$_2$—R$^k$,
(27) —N(R$^c$)—R$^k$,
(28) —N(R$^c$)—(CH$_2$)$_{1-4}$H substituted with one or two R$^k$ groups,
(29) —N(R$^c$)—(CH$_2$)$_{1-4}$OR$^k$,
(30) —C(=O)N—(CH$_2$)$_{1-4}$R$^k$,
(31) —C≡C—CH$_2$SR$^a$, or
(32) —C≡C—CH$_2$SO$_2$R$^a$;

each of R$^1$ and R$^2$ is independently:
(1) —H,
(2) methyl,
(3) ethyl, (4) $CF_3$,
(5) methoxy,
(6) ethoxy
(7) —$OCF_3$
(8) halo selected from —F, —Cl and —Br,
(9) —CN,
(10) —$CH_2OR^a$,
(11) —$CO_2R^a$,
(12) —$SR^a$,
(13) —$N(R^a)_2$,
(14) —$(CH_2)_{1-3}N(R^a)_2$,
(15) —$SO_2R^a$,
(16) —$(CH_2)_{1-2}N(R^a)$—$C(R^a)$=O,
(17) —$R^k$,
(18) —$(CH_2)_{1-3}H$ substituted with 1 or 2 $R^k$ groups,
(19) —O—$R^k$, or
(20) —O—$(CH_2)_{1-3}R^k$;
$R^5$ is
(1) —H,
(2) methyl,
(3) —$(CH_2)_{1-2}N(R^a)_2$,
(4) —$(CH_2)_{1-2}CO_2CH_3$, or
(5) —$(CH_2)_{1-2}CO_2CH_2CH_3$;
(6) phenyl, or
(7) benzyl;
each $R^a$ is independently —H or —$C_{1-4}$ alkyl;
each $R^c$ is independently —H, —$C_{1-4}$ alkyl, or —$(CH_2)_{1-3}N(R^a)_2$;
each $R^k$ is independently:
(1) phenyl which is unsubstituted or substituted with from 1 to 4 substituents independently selected from:
  (a) halogen selected from —F, —Cl, and —Br,
  (b) methyl,
  (c) —$CF_3$,
  (d) methoxy,
  (e) —$OCF_3$,
  (f) phenyl,
  (g) —S—$CH_3$,
  (h) —CN,
  (i) —OH,
  (j) phenyloxy, unsubstituted or substituted with from 1 to 3 substituents independently selected from:
    (i) halogen selected from —F, —Cl, and —Br,
    (ii) methyl,
    (iii) —$CF_3$, and
    (iv) —OH,
  (k) —$N(R^a)_2$,
  (l) —$(CH_2)_{1-3}N(R^a)_2$,
  (m) —$R^t$,
  (p) —$(CH_2)_{0-3}C(=O)N(R^a)_2$, and
  (q) —$(CH_2)_{0-3}C(=O)R^a$;
(2) —$C_{3-6}$ cycloalkyl, unsubstituted or substituted with from 1 to 3 substituents independently selected from:
  (a) halogen selected from —F, —Cl, and —Br,
  (b) methyl,
  (c) —$CF_3$,
  (d) methoxy,
  (e) —$OCF_3$,
  (f) —CN,
  (h) phenyl, and
  (j) —OH;
(3) a 5- or 6-membered heteroaromatic ring selected from thienyl, pyridyl, imidazolyl, pyrrolyl, pyrazolyl, thiazolyl, isothiazolyl, oxazolyl, isooxazolyl, pyrazinyl, pyrimidinyl, triazolyl, tetrazolyl, furanyl, and pyridazinyl, wherein the heteroaromatic ring is unsubstituted or substituted on nitrogen or carbon with 1 or 2 substituents independently selected from:
  (a) halogen selected from —F, —Cl, and —Br,
  (b) methyl,
  (c) —$CF_3$,
  (d) methoxy,
  (e) —$OCF_3$,
  (f) phenyl,
  (g) —S—$C_{1-6}$ alkyl,
  (h) —CN,
  (i) —OH,
  (j) phenyloxy, unsubstituted or substituted with from 1 to 3 substituents independently selected from:
    (i) halogen selected from —F, —Cl, and —Br,
    (ii) methyl,
    (iii) —$CF_3$, and
    (iv) —OH,
  (k) —$N(R^a)_2$,
  (l) —$C_{1-6}$ alkyl-$N(R^a)_2$,
  (m) —$R^t$,
  (n) oxo,
  (o) —$(CH_2)_{0-3}C(=O)N(R^a)_2$, and
  (p) —$(CH_2)_{0-3}C(=O)R^a$;
(4) a 5- or 6-membered saturated heterocyclic ring selected from piperidinyl, morpholinyl, thiomorpholinyl, thiazolidinyl, isothiazolidinyl, oxazolidinyl, isooxazolidinyl, pyrrolidinyl, imidazolidinyl, piperazinyl, tetrahydrofuranyl, and pyrazolidinyl, wherein the heterocyclic ring is unsubstituted or substituted with 1 or 2 substituents independently selected from:
  (a) halogen selected from —F, —Cl, and —Br,
  (b) methyl,
  (c) —$CF_3$,
  (d) methoxy,
  (e) —$OCF_3$,
  (f) —CN,
  (g) =O,
  (h) phenyl,
  (i) benzyl,
  (j) phenylethyl,
  (k) —OH,
  (l) —$(CH_2)_{0-3}C(=O)N(R^a)_2$,
  (m) —$(CH_2)_{0-3}C(=O)R^a$,
  (n) $N(R^a)$—$C(=O)R^a$,
  (o) $N(R^a)$—$C(=O)OR^a$,
  (p) $(CH_2)_{1-3}N(R^a)$—$C(=O)R^a$,
  (q) $N(R^a)_2$,
  (r) $(CH_2)_{1-3}N(R^a)_2$,
  (s) —$(CH_2)_{0-3}C(=O)R^t$,
  (t) —$R^t$,
  (u) —$N(R^a)R^t$, and
  (v) —$(CH_2)_{1-3}R^t$; and
(5) an 8- to 10-membered heterobicyclic ring selected from indolyl, benzotriazolyl, benzoimidazolyl, imidazo[4,5-b]pyridinyl, dihydroimidazo[4,5-b]pyridinyl, pyrazolo[4,3-c]pyridinyl, dihydropyrazolo[4,3c]pyridinyl, tetrahydropyrazolo[4,3-c]pyridinyl, pyrrolo[1,2-a]pyrazinyl, dihydropyrrolo[1,2-a]pyrazinyl, tetrahydropyrrolo[1,2-a]pyrazinyl, octahydropyrrolo[1,2-a]pyrazinyl, isoindolyl, indazolyl, indolinyl, isoindolinyl, quinolinyl, isoquinolinyl, quinoxalinyl, quinazolinyl, cinnolinyl, chromanyl, and isochromanyl, wherein the bicyclic ring is unsubstituted or substituted with 1 or 2 substituents independently selected from:
(a) halogen selected from —F, —Cl, and —Br,
(b) methyl,
(c) —CF$_3$,
(d) methoxy,
(e) —OCF$_3$,
(f) —CN,
(g) =O, and
(h) —OH;

R$^t$ is selected from pyrrolidinyl, pyrazolidinyl, imidazolinyl, piperidinyl, piperazinyl, pyrrolyl, pyridyl, imidazolyl, pyrazolyl, triazolyl, tetrazolyl, pyrazinyl, pyrimidinyl, and pyradizinyl; any one of which is unsubstituted or substituted with 1 or 2 substituents independently selected from —F, —Cl, —Br, oxo, methyl, and methoxy;
or a pharmaceutically acceptable salt thereof.

A second class of the present invention is compounds of Formula (IV):

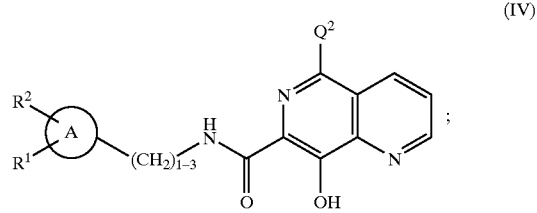

(IV)

wherein

A is
(i) a monocyclic heterocycle selected from the group consisting of pyrrolyl, pyrazolyl, imidazolyl, triazolyl, tetrazolyl, pyridyl, pyrazinyl, pyrimidinyl, pyrazidinyl, oxazolyl, isooxazolyl, thiazolyl, isothiazolyl, pyrrolidinyl, pyrazolidinyl, imidazolinyl, piperidinyl, piperazinyl, thiazolidinyl, isothiazolidinyl, and morpholinyl;
(ii) a fused bicyclic heterocycle selected from the group consisting of indolyl, isoindolyl, phthalazinyl, purinyl, quinoxalinyl, quinazolinyl, cinnolinyl, 1,6-naphthyridinyl, 1,8-napthyridinyl, benzimidazolyl, quinolinyl, isoquinolinyl, indazolyl, dihydroindolyl, dihydroisoindolyl, tetrahydroquinolyl, tetrahydroisoquinolyl, imidazo[1,2-a]pyrimidinyl, 2,3-dihydroimidazo[2,1b][1,3]thiazolyl, benzazepinyl, dihydrobenazepinyl, benzodiazepinyl, dihydrobenzodiazepinyl, tetrahydrobenzodiazepinyl, and benzothiazolyl; or
(iii) a fused tricyclic heterocycle selected from the group consisting of phenothiazinyl, carbazolyl, beta-carbolinyl, tetrahydro-beta-carbolinyl, acridinyl, phenazinyl, and phenoxazinyl;

each R$^k$ is independently:
(1) phenyl which is unsubstituted or substituted with from 1 to 2 substituents independently selected from:
(a) halogen selected from —F, —Cl, and —Br,
(b) methyl,
(c) —CF$_3$,
(d) methoxy,
(e) —OCF$_3$,
(f) phenyl,
(g) —S—CH$_3$,
(h) —CN,
(i) —OH,
(j) phenyloxy
(k) —N(R$^a$)$_2$,
(l) —(CH$_2$)$_{1-3}$N(R$^a$)$_2$,
(m) —R$^t$,
(p) —(CH$_2$)$_{0-3}$C(=O)N(R$^a$)$_2$, and
(q) —(CH$_2$)$_{0-3}$C(=O)R$^a$;
(2) —C$_{3-6}$ cycloalkyl;
(3) a 5- or 6-membered heteroaromatic ring selected from thienyl, pyridyl, imidazolyl, pyrrolyl, pyrazolyl, thiazolyl, isothiazolyl, pyrazinyl, pyirimidinyl, triazolyl, and tetrazolyl, wherein the heteroaromatic ring is unsubstituted or substituted on nitrogen or carbon with 1 or 2 substituents independently selected from:
(a) halogen selected from —F, —Cl, and —Br,
(b) methyl,
(c) —CF$_3$,
(d) methoxy,
(e) —OCF$_3$,
(f) —S—C$_{1-6}$ alkyl,
(g) —CN,
(h) —OH,
(i) —N(R$^a$)$_2$,
(j) —C$_{1-6}$ alkyl-N(R$^a$)$_2$,
(k) —R$^t$,
(l) oxo,
(m) —(CH$_2$)$_{0-3}$C(=O)N(R$^a$)$_2$, and
(n) —(CH$_2$)$_{0-3}$C(=O)R$^a$;
(4) a 5- or 6-membered saturated heterocyclic ring selected from piperidinyl, morpholinyl, thiomorpholinyl, thiazolidinyl, isothiazolidinyl, oxazolidinyl, isooxazolidinyl, pyrrolidinyl, imidazolidinyl and, piperazinyl, wherein the heterocyclic ring is unsubstituted or substituted with 1 or 2 substituents independently selected from:
(a) halogen selected from —F, —Cl, and —Br,
(b) methyl,
(c) —CF$_3$,
(d) methoxy,
(e) —OCF$_3$,
(f) —CN,
(g) =O,
(h) phenyl,
(i) benzyl,
(j) phenylethyl,
(k) —OH,
(l) —(CH$_2$)$_{0-3}$C(=O)N(R$^a$)$_2$,
(m) —(CH$_2$)$_{0-3}$C(=O)R$^a$,
(n) N(R$^a$)—C(=O)R$^a$,
(o) N(R$^a$)—C(=O)OR$^a$,
(p) (CH$_2$)$_{1-3}$N(R$^a$)—C(=O)R$^a$,
(q) N(R$^a$)$_2$,
(r) (CH$_2$)$_{1-3}$N(R$^a$)$_2$,
(s) —(CH$_2$)$_{0-3}$C(O)R$^t$,
(t) —R$^t$,
(u) —N(R$^a$)R$^t$, and
(v) —(CH$_2$)$_{1-3}$R$^t$; and
(5) an 8- to 10-membered heterobicyclic ring selected from indolyl, imidazo[4,5-b]pyridinyl, dihydroimidazo[4,5-b]pyridinyl, pyrazolo[4,3c]pyridinyl, dihydropyrazolo[4,3-c]pyridinyl, tetrahydropyrazolo[4,3-c]pyridinyl, pyrrolo[1,2-a]pyrazinyl, dihydropyrrolo[1,2-a]pyrazinyl, tetrahydropyrrolo[1,2a]pyrazinyl, octahydropyrrolo[1,2-a]pyrazinyl, isoindolyl, indazolyl, indolinyl, isoindolinyl, quinolinyl, isoquinolinyl, quinoxalinyl, and quinazolinyl, wherein the bicyclic ring is unsubstituted or substituted with 1 or 2 substituents independently selected from:
(a) halogen selected from —F, —Cl, and —Br,
(b) methyl,
(c) —CF$_3$,
(d) methoxy,
(e) —OCF$_3$,
(f) —CN,
(g) =O, and
(h) —OH; and R' is selected from pyrrolidinyl, pyrazolidinyl, imidazolinyl, piperidinyl, piperazinyl, pyrrolyl, pyridyl, imidazolyl, pyrazolyl, triazolyl, tetrazolyl, pyrazinyl, pyrimidinyl, and pyradizinyl; any one of which is unsubstituted or substituted with 1 or 2 substituents independently selected from —F, —Cl, —Br, oxo, methyl, and methoxy;
and all other variables are as defined in the first class;
or a pharmaceutically acceptable salt thereof.

A first sub-class of the present invention is compounds of Formula IV, wherein:

A is
(i) a monocyclic heterocycle selected from the group consisting of pyrrolyl, pyrazolyl, imidazolyl, triazolyl, tetrazolyl, pyridyl, oxazolyl, isooxazolyl, thiazolyl, pyrrolidinyl, piperidinyl, piperazinyl, thiazolidinyl, and morphonlinyl;
(ii) a fused bicyclic heterocycle selected from the group consisting of indolyl, isoindolyl, phthalazinyl, benzimidazolyl, quinolinyl, isoquinolinyl, dihydroindolyl, dihydroisoindolyl, tetrahydroquinolyl, tetrahydroisoquinolyl, imidazo[1,2-a]pyrimidinyl, 2,3-dihydroimidazo[2,1-b][1,3]thiazolyl, benzazepinyl, dihydrobenazepinyl, benzodiazepinyl, dihydrobenzodiazepinyl, benzothiazolyl and tetrahydrobenzodiazepinyl; or
(iii) a fused tricyclic heterocycle selected from the group consisting of phenothiazinyl, beta-carbolinyl, and tetrahydro-beta-carbolinyl;
and all other variables are as defined in the second class of the invention;
or a pharmaceutically acceptable salt thereof.

In an aspect of the first sub-class, A is selected from the group consisting of indolyl, phenothiazinyl, benzimidazolyl, phthalazinyl, and dihydroimidazothiazolyl.

In another aspect of the first sub-class, A is indolyl.

Exemplary compounds of the invention include compounds selected from the group consisting of 2-({[(8-hydroxy-1,6-naphthyridin-7-yl)carbonyl]amino}methyl)-1H-benzimidazole;
8-hydroxy-N-[2-(1H-indol-3-yl)ethyl]-1,6-naphthyridine-7-carboxamide;
N-{2-[2-(3,4-dimethoxyphenyl)-1H-indol-3-yl]ethyl}-8-hydroxy-1,6-naphthyridine-7carboxamide;
8-hydroxy-N-[(2-oxo-2,3-dihydro-1H-indol-3-yl)methyl]-1,6-naphthyridine-7carboxamide;
8-hydroxy-N-[2-(10H-phenothiazin-10-yl)ethyl]-1,6-naphthyridine-7-carboxamide;
8-hydroxy-N-[2-(2-methyl-1-phenyl-1H-indol-3-yl)ethyl]-1,6-naphthyridine-7carboxamide;
8-hydroxy-N-(1H-indol-6-ylmethyl)-1,6-naphthyridine-7-carboxamide;
8-hydroxy-N-(1H-indol-2-ylmethyl)-1,6-naphthyridine-7-carboxamide;
8-hydroxy-N-[(4-oxo-3,4-dihydrophthalazin-1-yl)methyl]-1,6-naphthyridine-7carboxamide;
tert-butyl 3-({[(8-hydroxy-1,6-naphthyridin-7-yl)carbonyl]amino}methyl)-1H-indole-1-carboxylate;
8-hydroxy-N-(1H-indol-3-ylmethyl)-1,6-naphthyridine-7-carboxamide;
6-({[(8-hydroxy-1,6-naphthyridin-7-yl)carbonyl]amino}methyl)-2,3-dihydroimidazo[2,1-b[]1,3]thiazole;
8-hydroxy-N-(4-pyridinylmethyl)[1,6]naphthyridine-7-carboxamide;
8-hydroxy-N-(2-pyridinylmethyl)[1,6]naphthyridine-7-carboxamide;
and pharmaceutically acceptable salts thereof.

Other embodiments of the invention include compounds of Formula (I), (II), (III), or (IV), wherein each variable is independently as defined in any one of the preceding embodiments, classes, sub-classes or aspects.

Other embodiments of the present invention include the following:
(a) A pharmaceutical composition comprising a compound of Formula (I) and a pharmaceutically acceptable carrier.
(b) The pharmaceutical composition of (a), further comprising at least one antiviral selected from the group consisting of HIV protease inhibitors, non-nucleoside HIV reverse transcriptase inhibitors, and nucleoside HIV reverse transcriptase inhibitors.
(c) A method of inhibiting HIV integrase in a subject in need thereof which comprises administering to the subject a therapeutically effective amount of a compound of Formula (I).
(d) A method of preventing or treating infection by HIV in a subject in need thereof which comprises administering to the subject a therapeutically effective amount of a compound of Formula (I).
(e) The method of (d), wherein the compound of Formula (I) is administered in combination with a therapeutically effective amount of at least one antiviral selected from the group consisting of HIV protease inhibitors, non-nucleoside HIV reverse transcriptase inhibitors, and nucleoside HIV reverse transcriptase inhibitors.
(f) A method of preventing, treating or delaying the onset of AIDS in a subject in need thereof which comprises administering to the subject a therapeutically effective amount of a compound of Formula (I).
(g) The method of (f), wherein the compound is administered in combination with a therapeutically effective amount of at least one antiviral selected from the group consisting of HIV protease inhibitors, non-nucleoside HIV reverse transcriptase inhibitors, and nucleoside HIV reverse transcriptase inhibitors
(h) A method of inhibiting HIV integrase in a subject in need thereof which comprises administering to the subject a therapeutically effective amount of the composition of (a) or (b).
(i) A method of preventing or treating infection by HIV in a subject in need thereof which comprises administering to the subject a therapeutically effective amount of the composition of (a) or (b).
(j) A method of preventing, treating or delaying the onset of AIDS in a subject in need thereof which comprises administering to the subject a therapeutically effective amount of the composition of (a) or (b).

Still other embodiments of the present invention include the following:
(k) A pharmaceutical composition which comprises the product prepared by combining (e.g., mixing) an effective amount of a compound of Formula (I) and a pharmaceutically acceptable carrier.

(l) A combination useful for inhibiting HIV integrase, for treating or preventing infection by HIV, or for preventing, treating or delaying the onset of AIDS, which is a therapeutically effective amount of a compound of Formula (I) and a therapeutically effective amount of an HIV infection/AIDS treatment agent selected from the group consisting of HIV/AIDS antiviral agents, immunomodulators, and anti-infective agents.

(m) The combination of (l), wherein the HIV infection/AIDS treatment agent is an antiviral selected from the group consisting of HIV protease inhibitors, non-nucleoside HIV reverse transcriptase inhibitors and nucleoside HIV reverse transcriptase inhibitors.

Additional embodiments of the invention include the pharmaceutical compositions and methods set forth in (a)–(j) above and the compositions and combinations set forth in (k)–(m), wherein the compound employed therein is a compound of one of the embodiments, classes, sub-classes, or aspects of compounds described above. In all of these embodiments, the compound may optionally be used in the form of a pharmaceutically acceptable salt.

The present invention also includes use of a compound of Formula (I-A):

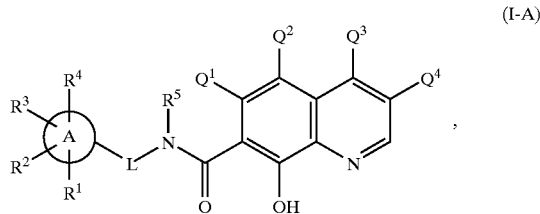

(I-A)

or a pharmaceutically acceptable salt thereof, for inhibiting HIV integrase, for preventing or treating infection by HIV or for preventing, treating or delaying the onset of AIDS in a subject in need thereof; wherein A, $R^1$, $R^2$, $R^3$, $R^4$, $R^5$, L, $Q^1$, $Q^2$, $Q^3$, and $Q^4$ are each independently as originally defined above or as defined in any of the foregoing embodiments, classes, sub-classes, or aspects. In one aspect, the compound of Formula (I-A) is N-[2-(1H-Indol-3-yl)ethyl] 8-hydroxyquinoline-7-carboxamide; or a pharmaceutically acceptable salt thereof.

The present invention also include embodiments for compounds of Formula (I-A) analogous to embodiments (a)–(m) for compounds of Formula (I).

As used herein, the term "$C_{1-6}$ alkyl" (or "$C_1$–$C_6$ alkyl") means linear or branched chain alkyl groups having from 1 to 6 carbon atoms and includes all of the hexyl alkyl and pentyl alkyl isomers as well as n-, iso-, sec- and t-butyl, n- and isopropyl, ethyl and methyl. "$C_{1-4}$ alkyl" means n-, iso-, sec- and t-butyl, n- and isopropyl, ethyl and methyl.

The term "$C_0$" as employed in expressions such as "$C_{0-6}$ alkyl" means a direct covalent bond.

The term "$C_{2-5}$ alkenyl" (or "$C_2$–$C_5$ alkenyl") means linear or branched chain alkenyl groups having from 2 to 5 carbon atoms and includes all of the pentenyl isomers as well as 1-butenyl, 2-butenyl, 3-butenyl, isobutenyl, 1-propenyl, 2-propenyl, and ethenyl (or vinyl). Similar terms such as "$C_{2-3}$ alkenyl" have an analogous meaning.

The term "$C_{2-5}$ alkynyl" (or "$C_2$–$C_5$ alkynyl") means linear or branched chain alkynyl groups having from 2 to 5 carbon atoms and includes all of the pentynyl isomers as well as 1-butynyl, 2-butynyl, 3-butynyl, 1-propynyl, 2-propynyl, and ethynyl (or acetylenyl). Similar terms such as "$C_{2-3}$ alkynyl" have an analogous meaning.

The term "$C_{3-7}$ cycloalkyl" (or "$C_3$–$C_7$ cycloalkyl") means a cyclic ring of an alkane having three to seven total carbon atoms (i.e., cyclopropyl, cyclobutyl, cyclopentyl, cyclohexyl, or cycloheptyl). The term "$C_{3-6}$ cycloalkyl" refers to a cyclic ring selected from cyclopropyl, cyclobutyl, cyclopentyl, and cyclohexyl. Terms such as "$C_3$–$C_5$ cycloalkyl" have an analogous meaning.

The term "halogen" (or "halo") refers to fluorine, chlorine, bromine and iodine (alternatively, fluoro, chloro, bromo, and iodo).

The term "thio" (also referred to as "thioxo") means divalent sulfur; i.e., =S.

The term "$C_{1-6}$ haloalkyl" (which may alternatively be referred to as "$C_1$–$C_6$ haloalkyl" or "halogenated $C_1$–$C_6$ alkyl") means a $C_1$ to $C_6$ linear or branched alkyl group as defined above with one or more halogen substituents. The term "$C_{1-4}$ haloalkyl" has an analogous meaning.

The term "$C_{1-6}$ fluoroalkyl" (which may alternatively be referred to as "$C_1$–$C_6$ fluoroalkyl" or "fluorinated $C_1$–$C_6$ alkyl") means a $C_1$ to $C_6$ linear or branched alkyl group as defined above with one or more fluorine substituents. The term "$C_{1-4}$ fluoroalkyl" (or "$C_1$–$C_4$ fluoroalkyl" or "fluorinated $C_1$–$C_4$ alkyl") has an analogous meaning. Representative examples of suitable fluoroalkyls include the series $(CH_2)_{0-4}CF_3$ (i.e., trifluoromethyl, 2,2,2-trifluoroethyl, 3,3,3-trifluoro-n-propyl, etc.), 1-fluoroethyl, 2-fluoroethyl, 2,2-difluoroethyl, 3,3,3-trifluoroisopropyl, 1,1,1,3,3,3-hexafluoroisopropyl, and perfluorohexyl.

The term "carbocycle" (and variations thereof such as "carbocyclic" or "carbocyclyl") as used herein broadly refers to a $C_3$ to $C_8$ monocyclic, saturated or unsaturated ring or a $C_7$ to $C_{12}$ bicyclic ring system in which the rings are independent or fused and in which each ring is saturated or unsaturated. The carbocycle may be attached at any carbon atom which results in a stable compound. The fused bicyclic carbocycles are a subset of the carbocycles; i.e., the term "fused bicyclic carbocycle" generally refers to a $C_7$ to $C_{10}$ bicyclic ring system in which each ring is saturated or unsaturated and two adjacent carbon atoms are shared by each of the rings in the ring system. A subset of the fused bicyclic carbocycles are the fused bicyclic carbocycles in which one ring is a benzene ring and the other ring is saturated or unsaturated, with attachment via any carbon atom that results in a stable compound. Representative examples of this subset include the following:

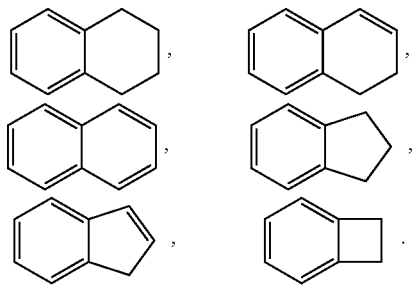

As used herein, the term "fused carbocyclic ring system" refers to a carbocycle as defined above which is fused to a phenyl ring. Representative examples include:

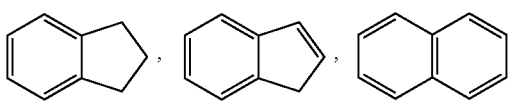

-continued

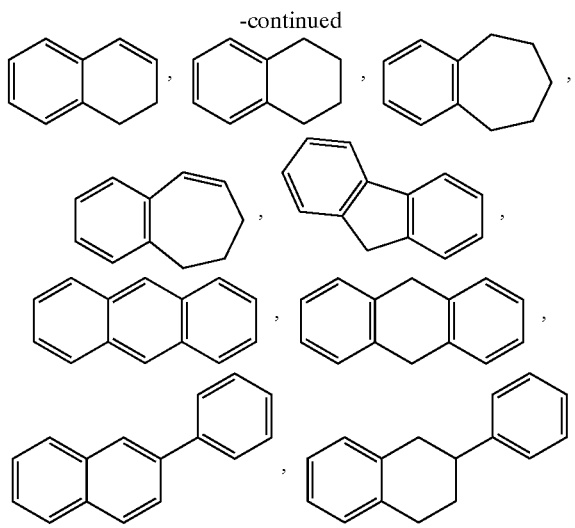

The term "aryl" refers to aromatic mono- and polycarbocyclic ring systems, wherein the individual carbocyclic rings in the polyring systems may be fused or attached to each other via a single bond. Suitable aryl groups include, but are not limited to, phenyl, naphthyl, and biphenylenyl.

The term "heterocycle" (and variations thereof such as "heterocyclic" or "heterocyclyl") broadly refers to a 4- to 8-membered monocyclic ring, 7- to 12-membered bicyclic ring system, or an 11 to 16-membered tricyclic ling system, any ring of which is saturated or unsaturated, and which consists of carbon atoms and one or more heteroatoms selected from N, O and S, and wherein the nitrogen and sulfur heteroatoms may optionally be oxidized, and the nitrogen heteroatom may optionally be quaternized. The heterocyclic ring may be attached at any heteroatom or carbon atom, provided that attachment results in the creation of a stable structure. When the heterocyclic ring has substituents, it is understood that the substituents may be attached to any atom in the ring, whether a heteroatom or a carbon atom, provided that a stable chemical structure results. Representative examples of heterocyclics include piperidinyl, piperazinyl, azepinyl, pyrrolyl, pyrrolidinyl, pyrazolyl, pyrazolidinyl, imidazolyl, imidazolidinyl, triazolyl, tetrazolyl, imidazolinyl, pyridyl (or pyridinyl), pyrazinyl, pyrimidinyl, pyridazinyl, oxazolyl, oxazolidinyl, isoxazolyl, isoxazolidinyl, morpholinyl, thiomorpholinyl, thiazolyl, thiazolidinyl, isothiazolyl, quinoxazolinyl, isothiazolidinyl, quinolinyl, isoquinolinyl, benzimidazolyl, thiadazolyl, benzopyranyl, benzothiazolyl, benzoazolyl, furyl (or furanyl), tetrahydrofuryl (or tetrahydrofuranyl), tetrahydropuranyl, thienyl (alternatively thiophenyl), benzothiophenyl, oxadiazolyl, and benzo-1,3-dioxacyclopentyl (alternatively, 1,3-benzodioxolyl). Representative examples of heterocyclics also include tetrahydrothienyl, tetrahydrodioxothienyl, thiadiazinanyl, dioxothiadiazinanyl, thiazinanyl, dioxothiazinanyl, dioxothiazolidinyl, and isodioxothiazolidinyl. Representative examples of heterocyclics also include the following bicyclics: indolyl, benzotriazolyl, imidazo[4,5-b]pyridinyl, dihydroimidazo[4,5-b]pyridinyl, pyrazolo[4,3-c]pyridinyl, dihydropyrazolo[4,3-c]pyridinyl, tetrahydropyrazolo[4,3c] pyridinyl, pyrrolo[1,2-a]pyrazinyl, dihydropyrrolo[1,2-a] pyrazinyl, tetrahydropyrrolo[1,2-a]pyrazinyl, octahydropyrrolo[1,2-a]pyrazinyl, isoindolyl, indazolyl, indolinyl, isoindolinyl, quinoxalinyl, quinazolinyl, cinnolinyl, chromanyl, and isochromanyl. Additional representative examples of bicyclics include the following: phthalazinyl, purinyl, 1,6-naphthyridinyl, 1,8-napthyridinyl, dihydroindolyl, dihydroisoindolyl, tetrahydroquinolyl, tetrahydroisoquinolyl, imidazo[1,2-a]pyrimidinyl, 2,3-dihydroimidazo[2,1-b][1,3]thiazolyl, benzazepinyl, dihydrobenazepinyl, benzodiazepinyl, dihydrobenzodiazepinyl, and tetrahydrobenzodiazepinyl. Representative examples of heterocyclics also include the following tricyclics: phenothiazinyl, carbazolyl, beta-carbolinyl, tetrahydro-beta-carbolinyl, acridinyl, phenazinyl, and phenoxazinyl.

Representative examples of heterocyclics also include the following saturated monocyclics: hexahydropyrimidinyl, thiazinanyl (e.g., 1,2-thiazinanyl, alternatively named tetrahydro-1,2-thiazinyl), thiazepanyl (e.g., 1,4-thiazepanyl, alternatively named hexahydro-1,4-thiazepinyl), azepanyl (alternatively hexahydroazepinyl), thiadiazepanyl (e.g., 1,2,5-thiadiazepanyl), dithiazepanyl (e.g., 1,5,2,-dithiazepanyl), diazepanyl (e.g., 1,4-diazepanyl), and thiadiazinanyl (e.g., 1,2,6-thiadiazinanyl).

A representative unsaturated heterocycle is

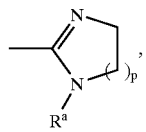

wherein p is an integer from zero to 4 and $R^a$ is as defined above, and wherein each ring carbon is optionally and independently substituted with —$C_{1-4}$ alkyl.

Representative examples of heterocyclics also include the following bicyclics: hexahydropyrazolo[4,3-c]pyridinyl (e.g., 3a,4,5,6,7,7a-hexahydro-1H-pyrazolo[4,3c]pyridinyl), hexahydropurinyl (e.g., 2,3,4,5,6,7-hexahydro-1H-purinyl), hexahydrooxazolo[3,4a]pyrazinyl, and 1,2,3,4-tetrahydro-1, 8-naphthyridinyl.

Fused ring heterocycles form a subset of the heterocycles as defined above; e.g., the term "fused bicyclic heterocycle" refers to a heteroatom-containing bicyclic ring system as defined in the preceding paragraph in which two adjacent atoms are shared by both rings. A subset of the fused bicyclic heterocycles is the fused bicyclic heterocycle containing carbon atoms and one or more heteroatoms selected from nitrogen, oxygen and sulfur, wherein one ring is a benzene ring and the other is a saturated or unsaturated heteroatom-containing ring. Representative examples of this subset include, but are not limited to, the following:

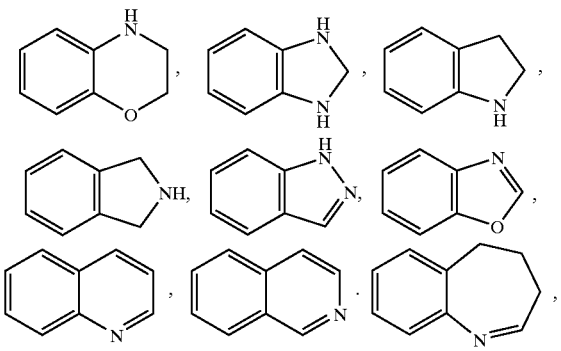

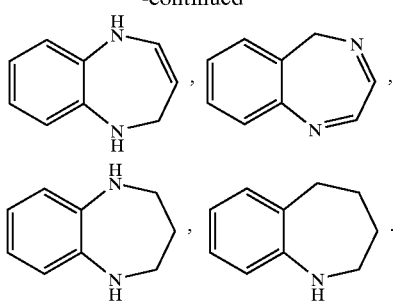

The term "heteromonocycle" (and variations thereof such as "heteromonocyclyl" or "heteromonocyclic") refers to a 4- to 8-membered monocyclic ring which is saturated or unsaturated, and which consists of carbon atoms and one or more heteroatoms selected from N, O and S, and wherein the nitrogen and sulfur heteroatoms may optionally be oxidized, and the nitrogen heteroatom may optionally be quaternized. The heterocyclic ring may be attached at any heteroatom or carbon atom, provided that attachment results in the creation of a stable structure. Representative examples of monoheterocycles are disclosed above.

Heteroaromatics form another subset of the heterocycles as defined above; i.e., the term "heteroaromatic" (alternatively, "heteroaryl") generally refers to a heterocycle as defined above in which the ring system (whether mono- or poly-cyclic) is an aromatic ring system. The term "heteroaromatic ring" refers to a monocyclic heterocycle as defined above which is an aromatic heterocycle. Representative examples of heteroaromatics include pyridyl, pyrrolyl, pyrazinyl, pyrimidinyl, pyridazinyl, thienyl (or thiophenyl), thiazolyl, furanyl, imidazolyl, pyrazolyl, triazolyl, tetrazolyl, oxazolyl, isooxazolyl, oxadiazolyl, thiazolyl, isothiazolyl, and thiadiazolyl.

Unless expressly set forth to the contrary, an "unsaturated" ring is a partially or fully unsaturated ring. For example, an "unsaturated monocyclic $C_6$ carbocycle" refers to cyclohexene, cyclohexadine, and benzene.

The present invention includes pharmaceutical compositions useful for inhibiting HIV integrase, comprising an effective amount of a compound of this invention, and a pharmaceutically acceptable carrier. Pharmaceutical compositions useful for treating infection by HIV, or for treating AIDS or ARC, are also encompassed by the present invention, as well as a method of inhibiting HIV integrase, and a method of treating infection by HIV, or of treating AIDS or ARC. Additionally, the present invention is directed to a pharmaceutical composition comprising a therapeutically effective amount of a compound of the present invention in combination with a therapeutically effective amount of an agent for treating HIV infection or AIDS selected from:

(1) an antiviral agent useful for treating or preventing HIV infection or for treating AIDS (also referred to herein as an HIV/AIDS antiviral agent), (2) an anti-infective agent, and (3) an immunomodulator.

The present invention also includes a compound of the present invention for use in (a) inhibiting HIV integrase, (b) preventing or treating infection by HIV, or (c) preventing, treating or delaying the onset of AIDS or ARC. The present invention also includes the use of a compound of the present invention as described above as a medicament for (a) inhibiting HIV integrase, (b) preventing or treating infection by HIV, or (c) preventing, treating or delaying the onset of AIDS or ARC. The present invention further includes the use of any of the HIV integrase inhibiting compounds of the present invention as described above in combination with one or more HIV/AIDS treatment agents selected from an HIV/AIDS antiviral agent, an anti-infective agent, and an immunomodulator as a medicament for (a) inhibiting HIV integrase, (b) preventing or treating infection by HIV, or (c) preventing, treating or delaying the onset of AIDS or ARC, said medicament comprising an effective amount of the HIV integrase inhibitor compound and an effective amount of the one or more treatment agents.

The present invention also includes the use of a compound of the present invention as described above in the preparation of a medicament for (a) inhibiting HIV integrase, (b) preventing or treating infection by HIV, or (c) preventing, treating or delaying the onset of AIDS or ARC.

The present invention further includes the use of any of the HIV integrase inhibiting compounds of the present invention as described above in combination with one or more HIV/AIDS treatment agents selected from an HIV/AIDS antiviral agent, an anti-infective agent, and an immunomodulator for the manufacture of a medicament for (a) inhibiting HIV integrase, (b) preventing or treating infection by HIV, or (c) preventing, treating or delaying the onset of AIDS or ARC, said medicament comprising an effective amount of the HIV integrase inhibitor compound and an effective amount of the one or more treatment agents.

The compounds of the present invention may have asymmetric centers and may occur, except when specifically noted, as mixtures of stereoisomers or as individual diastereomers, or enantiomers, with all isomeric forms being included in the present invention.

When any variable (e.g., $R^a$, $R^b$, $R^c$, $R^k$, etc.) occurs more than one time in any constituent or in Formula I or in any other formula depicting and describing compounds of the invention, its definition on each occurrence is independent of its definition at every other occurrence. Also, combinations of substituents and/or variables are permissible only if such combinations result in stable compounds.

The term "substituted" (e.g., as in "phenyl ring, unsubstituted or substituted with from 1 to 5 substituents . . . ") includes mono- and poly-substitution by a named substituent to the extent such single and multiple substitution is chemically allowed. For example, a carbocycle or heterocycle substituted with more than one substituent can have multiple substituents on the same ring atom to the extent it is chemically permitted. A ring sulfur atom in a saturated heterocycle can, for example, typically be substituted with 1 (—S(=O)—) or 2 oxo groups (—SO$_2$—).

The compounds of the present inventions are useful in the inhibition of HIV integrase, the prevention or treatment of infection by human immunodeficiency virus (HIV) and the treatment of consequent pathological conditions such as AIDS. Treating AIDS or preventing or treating infection by HIV is defined as including, but not limited to, treating a wide range of states of HIV infection: AIDS, ARC (AIDS related complex), both symptomatic and asymptomatic, and actual or potential exposure to HIV. For example, the compounds of this invention are useful in treating infection by HIV after suspected past exposure to HIV by e.g., blood transfusion, exchange of body fluids, bites, accidental needle stick, or exposure to patient blood during surgery.

The compounds of this invention are useful in the preparation and execution of screening assays for antiviral compounds. For example, the compounds of this invention are useful for isolating enzyme mutants, which are excellent screening tools for more powerful antiviral compounds.

Furthermore, the compounds of this invention are useful in establishing or determining the binding site of other antivirals to HIV integrase, e.g., by competitive inhibition. Thus the compounds of this invention are commercial products to be sold for these purposes.

The present invention also provides for the use of a compound of Formula (I) or (I-A) to make a pharmaceutical composition useful for inhibiting HIV integrase and in the treatment of AIDS or ARC.

The compounds of the present invention may be administered in the form of pharmaceutically acceptable salts. The term "pharmaceutically acceptable salt" is intended to include all acceptable salts such as acetate, lactobionate, benzenesulfonate, laurate, benzoate, malate, bicarbonate, maleate, bisulfate, mandelate, bitartrate, mesylate, borate, methylbromide, bromide, methylnitrate, calcium edetate, methylsulfate, carnsylate, mucate, carbonate, napsylate, chloride, nitrate, clavulanate, N-methylglucamine, citrate, ammonium salt, dihydrochloride, oleate, edetate, oxalate, edisylate, pamoate (embonate), estolate, palmitate, esylate, pantothenate, fumarate, phosphate/diphosphate, gluceptate, polygalacturonate, gluconate, salicylate, glutamate, stearate, glycollylarsanilate, sulfate, hexylresorcinate, subacetate, hydrabamine, succinate, hydrobromide, tannate, hydrochloride, tartrate, hydroxynaphthoate, teoclate, iodide, tosylate, isothionate, triethiodide, lactate, panoate, valerate, and the like which can be used as a dosage form for modifying the solubility or hydrolysis characteristics or can be used in sustained release or pro-drug formulations. Depending on the particular functionality of the compound of the present invention, pharmaceutically acceptable salts of the compounds of this invention include those formed from cations such as sodium, potassium, aluminum, calcium, lithium, magnesium, zinc, and from bases such as ammonia, ethylenediamine, N-methyl-glutamine, lysine, arginine, omithine, choline, N,N'-dibenzylethylene-diamine, chloroprocaine, diethanolamine, procaine, N-benzylphenethyl-amine, diethylamine, piperazine, tris (hydroxymethyl)aminomethane, and tetramethylammonium hydroxide. These salts may be prepared by standard procedures, e.g. by reacting a free acid with a suitable organic or inorganic base. Where a basic group is present, such as amino, an acidic salt, i.e. hydrochloride, hydrobromide, acetate, pamoate, and the like, can be used as the dosage form.

Also, in the case of an acid (—COOH) or alcohol group being present, pharmaceutically acceptable esters can be employed, e.g. acetate, maleate, pivaloyloxymethyl, and the like, and those esters known in the art for modifying solubility or hydrolysis characteristics for use as sustained release or prodrug formulations.

For these purposes, the compounds of the present invention may be administered orally, parenterally (including subcutaneous injections, intravenous, intramuscular, intrasternal injection or infusion techniques), by inhalation spray, or rectally, in dosage unit formulations containing conventional non-toxic pharmaceutically-acceptable carriers, adjuvants and vehicles.

The term "administration" and variants thereof (e.g., "administering" a compound) in reference to a compound of the invention each mean providing the compound or a prodrug of the compound to the individual in need of treatment. When a compound of the invention or prodrug thereof is provided in combination with one or more other active agents (e.g., antiviral agents useful for treating HIV infection or AIDS), "administration" and its variants are each understood to include concurrent and sequential provision of the compound or prodrug thereof and other agents.

Thus, in accordance with the present invention there is further provided a method of treating and a pharmaceutical composition for treating HIV infection and AIDS. The treatment involves administering to a subject in need of such treatment a pharmaceutical composition comprising a pharmaceutical carrier and a therapeutically-effective amount of a compound of the present invention.

As used herein, the term "composition" is intended to encompass a product comprising the specified ingredients in the specified amounts, as well as any product which results, directly or indirectly, from combination of the specified ingredients in the specified amounts.

By "pharmaceutically acceptable" it is meant the carrier, diluent or excipient must be compatible with the other ingredients of the formulation and not deleterious to the recipient thereof.

The term "subject," (alternatively referred to herein as "patient".) as used herein refers to an animal, preferably a mammal, most preferably a human, who has been the object of treatment, observation or experiment.

The term "therapeutically effective amount" as used herein means that amount of active compound or pharmaceutical agent that elicits the biological or medicinal response in a tissue, system, animal or human that is being sought by a researcher, veterinarian, medical doctor or other clinician, which includes alleviation of the symptoms of the disease being treated.

These pharmaceutical compositions may be in the form of orally-administrable suspensions or tablets or capsules, nasal sprays, sterile injectable preparations, for example, as sterile injectable aqueous or oleagenous suspensions or suppositories.

When administered orally as a suspension, these compositions are prepared according to techniques well-known in the art of pharmaceutical formulation and may contain microcrystalline cellulose for imparting bulk, alginic acid or sodium alginate as a suspending agent, methylcellulose as a viscosity enhancer, and sweeteners/flavoring agents known in the art. As immediate release tablets, these compositions may contain microcrystalline cellulose, dicalcium phosphate, starch, magnesium stearate and lactose and/or other excipients, binders, extenders, disintegrants, diluents and lubricants known in the art.

When administered by nasal aerosol or inhalation, these compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

The injectible solutions or suspensions may be formulated according to known art, using suitable non-toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

When rectally administered in the form of suppositories, these compositions may be prepared by mixing the drug with a suitable non-irritating excipient, such as cocoa butter, synthetic glyceride esters of polyethylene glycols, which are solid at ordinary temperatures, but liquefy and/or dissolve in the rectal cavity to release the drug.

The compounds of this invention can be administered orally to humans in a dosage range of 0.1 to 1000 mg/kg body weight in divided doses. One preferred dosage range is 0.1 to 200 mg/kg body weight orally in divided doses. Another preferred dosage range is 0.5 to 100 mg/kg body weight orally in divided doses. For oral administration, the compositions are preferably provided in the form of tablets containing 1.0 to 1000 milligrams of the active ingredient, particularly 1.0, 5.0, 10.0, 15.0. 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The present invention is also directed to combinations of the HIV integrase inhibitor compounds with one or more agents useful in the treatment of HIV infection or AIDS. For example, the compounds of this invention may be effectively administered, whether at periods of pre-exposure and/or post-exposure, in combination with effective amounts of the HIV/AIDS antivirals, immunomodulators, antiinfectives, or vaccines useful for treating HIV infection or AIDS, such as those in the following Table.

| Drug Name | Manufacturer | Indication |
| --- | --- | --- |
| ANTIVIRALS | | |
| Amprenavir 141 W94 GW 141 | Glaxo Wellcome | HIV infection, AIDS, ARC (protease inhibitor) |
| Abacavir GW 1592 1592U89 | Glaxo Welcome | HIV infection, AIDS, ARC (reverse transcriptase inhibitor) |
| Acemannan | Carrington Labs (Irving, TX) | ARC |
| Acyclovir | Burroughs Wellcome | HIV infection, AIDS, ARC, in combination with AZT |
| AD-439 | Tanox Biosystems | HIV infection, AIDS, ARC |
| AD-519 | Tanox Biosystems | HIV infection, AIDS, ARC |
| Adefovir dipivoxil | Gilead Sciences | HIV infection |
| AL-721 | Ethigen (Los Angeles, CA) | ARC, PGL, HIV positive, AIDS |
| Alpha Interferon | Glaxo Wellcome | Kaposi's sarcoma, HIV, in combination w/Retrovir |
| Ansamycin LM 427 | Adria Laboratories (Dublin, OH) Erbamont (Stamford, CT) | ARC |
| Antibody which neutralizes pH labile alpha aberrant Interferon | Advanced Biotherapy Concepts (Rockville, MD) | AIDS, ARC |
| AR177 | Aronex Pharm | HIV infection, AIDS, ARC |
| beta-fluoro-ddA | Nat'l Cancer Institute | AIDS-associated diseases |
| BMS-232623 (CGP-73547) | Bristol-Myers Squibb/ Novartis | HIV infection, AIDS, ARC (protease inhibitor) |
| BMS-234475 (CGP-61755) | Bristol-Myers Squibb/ Novartis | HIV infection, AIDS, ARC (protease inhibitor) |
| CI-1012 | Warner-Lambert | HIV-1 infection |
| Cidofovir | Gilead Science | CMV retinitis, herpes, papillomavirus |
| Curdlan sulfate | AJI Pharma U.S.A. | HIV infection |
| Cytomegalovirus immune globin | MedImmune | CMV retinitis |
| Cytovene Ganciclovir | Syntex | sight threatening CMV peripheral CMV retinitis |
| Delaviridine | Pharmacia-Upjohn | HIV infection, AIDS, ARC (protease inhibitor) |
| Dextran Sulfate | Ueno Fine Chem. Ind. Ltd. (Osaka, Japan) | AIDS, ARC, HIV positive asymptomatic |
| ddC Dideoxycytidine | Hoffman-La Roche | HIV infection, AIDS, ARC |
| ddI Dideoxyinosine | Bristol-Myers Squibb | HIV infection, AIDS, ARC; combination with AZT/d4T |
| mozenavir (DMP-450) | AVID (Camden, NJ) | HIV infection, AIDS, ARC (protease inhibitor) |

-continued

| Drug Name | Manufacturer | Indication |
|---|---|---|
| EL10 | Elan Corp, PLC (Gainesville, GA) | HIV infection |
| Efavirenz (DMP 266) (−) 6-Chloro-4(S)-cyclopropylethynyl-4(S)-trifluoro-methyl-1,4-dihydro-2H-3,1-benzoxazin-2-one, | DuPont (SUSTIVA ®), Merck (STOCRIN ®) | HIV infection, AIDS, ARC (non-nucleoside RT inhibitor) |
| Famciclovir | Smith Kline | herpes zoster, herpes simplex |
| FTC | Emory University | HIV infection, AIDS, ARC (reverse transcriptase inhibitor) |
| GS 840 | Gilead | HIV infection, AIDS, ARC (reverse transcriptase inhibitor) |
| HBY097 | Hoechst Marion Roussel | HIV infection, AIDS, ARC (non-nucleoside reverse transcriptase inhibitor) |
| Hypericin | VIMRx Pharm. | HIV infection, AIDS, ARC |
| Recombinant Human Interferon Beta | Triton Biosciences (Almeda, CA) | AIDS, Kaposi's sarcoma, ARC |
| Interferon alfa-n3 | Interferon Sciences | ARC, AIDS |
| Indinavir | Merck | HIV infection, AIDS, ARC, asymptomatic HIV positive, also in combination with AZT/ddI/ddC |
| Compound A | Merck | HIV infection, AIDS, ARC, asymptomatic HIV positive |
| ISIS 2922 | ISIS Pharmaceuticals | CMV retinitis |
| KNI-272 | Nat'l Cancer Institute | HIV-assoc. diseases |
| Lamivudine, 3TC | Glaxo Wellcome | HIV infection, AIDS, ARC (reverse transcriptase inhibitor); also with AZT |
| Lobucavir | Bristol-Myers Squibb | CMV infection |
| Nelfinavir | Agouron Pharmaceuticals | HIV infection, AIDS, ARC (protease inhibitor) |
| Nevirapine | Boeheringer Ingleheim | HIV infection, AIDS, ARC (protease inhibitor) |
| Novapren | Novaferon Labs, Inc. (Akron, OH) | HIV inhibitor |
| Peptide T Octapeptide Sequence | Peninsula Labs (Belmont, CA) | AIDS |
| Trisodium Phosphonoformate | Astra Pharm. Products, Inc | CMV retinitis, HIV infection, other CMV infections |
| PNU-140690 | Pharmacia Upjohn | HIV infection, AIDS, ARC (protease inhibitor) |
| Probucol | Vyrex | HIV infection, AIDS |
| RBC-CD4 | Sheffield Med. Tech (Houston TX) | HIV infection, AIDS, ARC |
| Ritonavir (ABT-538) | Abbott | HIV infection, AIDS, ARC (protease inhibitor) |
| Saquinavir | Hoffmann-LaRoche | HIV infection, AIDS, ARC (protease inhibitor) |
| Stavudine; d4T Didehydrodeoxy-thymidine | Bristol-Myers Squibb | HIV infection, AIDS, ARC |
| Valaciclovir | Glaxo Wellcome | genital HSV & CMV infections |
| Virazole Ribavirin | Viratek/ICN (Costa Mesa, CA) | asymptomatic HIV positive, LAS, ARC |
| VX-478 | Vertex | HIV infection, AIDS, ARC |
| Zalcitabine | Hoffmann-La Roche | HIV infection, AIDS, ARC, with AZT |
| Zidovudine; AZT | Glaxo Wellcome | HIV infection, AIDS, ARC, Kaposi's sarcoma in combination with other therapies (reverse transcriptase inhibitor) |
| ABT-378; Lopinavir | Abbott | HIV infection, AIDS, ARC (protease inhibitor) |
| ABT-378/r; contains | Abbott | HIV infection, AIDS, ARC |

-continued

| Drug Name | Manufacturer | Indication |
|---|---|---|
| lopinavir and ritonavir; Kaletra | | (protease inhibitor) |
| JE2147/AG1776 | Agouron | HIV infection, AIDS, ARC (protease inhibitor) |
| T-20 | Trimeris | HIV infection, AIDS, ARC (fusion inhibitor) |
| T-1249 | Trimeris | HIV infection, AIDS, ARC (fusion inhibitor) |
| atazanavir (BMS 232632) | Bristol-Myers-Squibb | HIV infection, AIDS, ARC (protease inhibitor) |
| PRO 542 | Progenics | HIV infection, AIDS, ARC (attachment inhibitor) |
| PRO 140 | Progenics | HIV infection, AIDS, ARC (CCR5 co-receptor inhibitor) |
| TAK-779 | Takeda | HIV infection, AIDS, ARC (injectable CCR5 receptor antagonist) |
| DPC 681 & DPC 684 | DuPont | HIV infection, AIDS, ARC (protease inhibitors) |
| DPC 961 & DPC 083 | DuPont | HIV infection AIDS, ARC (nonnucleoside reverse transcriptase inhibitors) |
| Trizivir (contains abacavir, lamivudine, and zidovudine) | GlaxoSmithKline | HIV infection, AIDS, ARC (reverse transcriptase inhibitors) |
| tipranavir (PNU-140690) | Boehringer Ingelheim (purchased from Pharmacia & Upjohn) | HIV infection, AIDS, ARC (protease inhibitor) |
| tenofovir disoproxil fumarate | Gilead | HIV infection, AIDS, ARC (reverse transcriptase inhibitor) |
| TMC-120 & TMC-125 | Tibotec | HIV infections, AIDS, ARC (non-nucleoside reverse transcriptase inhibitors) |
| TMC-126 | Tibotec | HIV infection, AIDS, ARC (protease inhibitor) |
| IMMUNO-MODULATORS | | |
| AS-101 | Wyeth-Ayerst | AIDS |
| Bropirimine | Pharmacia Upjohn | advanced AIDS |
| Acemannan | Carrington Labs, Inc. (Irving, TX) | AIDS, ARC |
| CL246,738 | American Cyanamid Lederle Labs | AIDS, Kaposi's sarcoma |
| EL10 | Elan Corp, PLC (Gainesville, GA) | HIV infection |
| FP-21399 | Fuki ImmunoPharm | blocks HIV fusion with CD4+ cells |
| Gamma Interferon | Genentech | ARC, in combination w/TNF (tumor necrosis factor) |
| Granulocyte Macrophage Colony Stimulating Factor | Genetics Institute Sandoz | AIDS |
| Granulocyte Macrophage Colony Stimulating Factor | Hoeschst-Roussel Immunex | AIDS |
| Granulocyte Macrophage Colony Stimulating Factor | Schering-Plough | AIDS, combination w/AZT |
| HIV Core Particle Immunostimulant | Rorer | seropositive HIV |
| IL-2 Interleukin-2 | Cetus | AIDS, in combination w/AZT |
| IL-2 Interleukin-2 | Hoffman-La Roche Immunex | AIDS, ARC, HIV, in combination w/AZT |
| IL-2 Interleukin-2 (aldeslukin) | Chiron | AIDS, increase in CD4 cell counts |
| Immune Globulin Intravenous (human) | Cutter Biological (Berkeley, CA) | pediatric AIDS, in combination w/AZT |
| IMREG-1 | Imreg (New Orleans, LA) | AIDS, Kaposi's sarcoma, ARC, PGL |
| IMREG-2 | Imreg (New Orleans, LA) | AIDS, Kaposi's sarcoma, ARC, PGL |

-continued

| Drug Name | Manufacturer | Indication |
|---|---|---|
| Imuthiol Diethyl Dithio Carbamate | Merieux Institute | AIDS, ARC |
| Alpha-2 Interferon | Schering Plough | Kaposi's sarcoma w/AZT, AIDS |
| Methionine-Enkephalin | TNI Pharmaceutical (Chicago, IL) | AIDS, ARC |
| MTP-PE Muramyl-Tripeptide | Ciba-Geigy Corp. | Kaposi's sarcoma |
| Granulocyte Colony Stimulating Factor | Amgen | AIDS, in combination w/AZT |
| Remune | Immune Response Corp. | immunotherapeutic |
| rCD4 Recombinant Soluble Human CD4 | Genentech | AIDS, ARC |
| rCD4-IgG hybrids | | AIDS, ARC |
| Recombinant Soluble Human CD4 | Biogen | AIDS, ARC |
| Interferon Alfa 2a | Hoffman-La Roche | Kaposi's sarcoma, AIDS, ARC, in combination w/AZT |
| SK&F106528 Soluble T4 | Smith Kline | HIV infection |
| Thymopentin | Immunobiology Research Institute | HIV infection |
| Tumor Necrosis Factor; TNF | Genentech | ARC, in combination w/gamma Interferon |
| etanercept | Immunex Corp (Enbrel ®) | rheumatoid arthritis |
| infliximab | Centocor (Remicade ®) | rheumatoid arthritis and Crohn's disease |
| ANTI-INFECTIVES | | |
| Clindamycin with Primaquine | Pharmacia Upjohn | PCP |
| Fluconazole | Pfizer | cryptococcal meningitis, candidiasis |
| Pastille Nystatin Pastille | Squibb Corp. | prevention of oral candidiasis |
| Ornidyl Eflornithine | Merrell Dow | PCP |
| Pentamidine Isethionate (IM & IV) | LyphoMed (Rosemont, IL) | PCP treatment |
| Trimethoprim | | antibacterial |
| Trimethoprim/sulfa | | antibacterial |
| Piritrexim | Burroughs Wellcome | PCP treatment |
| Pentamidine isethionate for inhalation | Fisons Corporation | PCP prophylaxis |
| Spiramycin | Rhone-Poulenc | cryptosporidia diarrhea |
| Intraconazole-R51211 | Janssen Pharm. | histoplasmosis; cryptococcal meningitis |
| Trimetrexate | Warner-Lambert | PCP |
| OTHER | | |
| Daunorubicin | NeXstar, Sequus | Karposi's sarcoma |
| Recombinant Human Erythropoietin | Ortho Pharm. Corp. | severe anemia assoc. with AZT therapy |
| Recombinant Human Growth Hormone | Serono | AIDS-related wasting, cachexia |
| Leukotriene B4 Receptor Antagonist | — | HIV infection |
| Megestrol Acetate | Bristol-Myers Squibb | treatment of anorexia assoc. w/AIDS |
| Soluble CD4 Protein and Derivatives | — | HIV infection |
| Testosterone | Alza, Smith Kline | AIDS-related wasting |
| Total Enteral Nutrition | Norwich Eaton Pharmaceuticals | diarrhea and malabsorption, related to AIDS |

It will be understood that the scope of combinations of the compounds of this invention with HIV/AIDS antivirals, immunomodulators, anti-infectives or vaccines is not limited to the list in the above Table, but includes in principle any combination with any pharmaceutical composition useful for the treatment of HIV infection or AIDS. When employed in combination with the compounds of the invention, the HIV/AIDS antivirals and other agents are typically employed in their conventional dosage ranges and regimens as reported in the art, including the dosages described in the *Physicians' Desk Reference,* 54th edition, Medical Economics Company, 2000. The dosage ranges for a compound of the invention in these combinations are the same as those set forth above just before the Table.

Preferred combinations are simultaneous or sequential treatments of a compound of the present invention and an inhibitor of HIV protease and/or a non-nucleoside inhibitor of HIV reverse transcriptase. An optional fourth component in the combination is a nucleoside inhibitor of HIV reverse transcriptase, such as AZT, 3TC, ddC or ddI. A preferred inhibitor of HIV protease is the sulfate salt of indinavir, which is N-(2(R)-hydroxy-1(S)-indanyl)-2(R)-phenylmethyl-4-(S)-hydroxy-5-(1-(4-(3-pyridyl-methyl)-2 (S)-N'-(t-butylcarboxamido)-piperazinyl))-pentaneamide ethanolate, and is synthesized according to U.S. Pat. No. 5,413,999. Indinavir is generally administered at a dosage of 800 mg three times a day. Other preferred protease inhibitors are nelfinavir and ritonavir. Another preferred inhibitor of HIV protease is saquinavir which is administered in a dosage of 600 or 1200 mg tid. Still another preferred protease inhibitor is Compound A, which is N-(2(R)-hydroxy-1(S)-indanyl)-2(R)-phenylmethyl-4(S)-hydroxy-5-(1-(4-(2-benzo[b]furanylmethyl)-2(S)-N'-(t-butylcarboxamido) piperazinyl))pentaneamide, preferably administered as the sulfate salt. Compound A can be prepared as described in U.S. Pat. No. 5,646,148. Preferred non-nucleoside inhibitors of HIV reverse transcriptase include efavirenz. The preparation of ddC, ddI and AZT are also described in EPO 0,484,071. These combinations may have unexpected effects on limiting the spread and degree of infection of HIV. Preferred combinations include a compound of the present invention with the following (1) indinavir with efavirenz, and, optionally, AZ and/or 3TC and/or ddI and/or ddC; (2) indinavir, and any of AZT and/or ddI and/or ddC and/or 3TC, in particular, indinavir and AZT and 3TC; (3) stavudine and 3TC and/or zidovudine; (4) zidovudine and lamivudine and 141W94 and 1592U89; (5) zidovudine and lamivudine.

Another preferred combination is a compound of the present invention with indinavir and Compound A and optionally with one or more of efavirenz, AZT, 3TC, ddI and ddC. In one embodiment of this combination, the weight ratio of indinavir to Compound A is from about 1:1 to about 1:2, wherein the amount of indinavir employed is in the range of from about 200 to about 1000 mg. Indinavir and Compound A can be administered concurrently or sequentially in either order from one to three times per day.

In such combinations the compound of the present invention and other active agents may be administered together or separately. In addition, the administration of one agent may be prior to, concurrent to, or subsequent to the administration of other agent(s).

Abbreviations used in the instant specification, particularly the Schemes and Examples, are as follows:

DEAD=diethylazodicarboxylate
DMF=N,N-dimethylformamide
DMPU=1,3-dimethyl-3,4,5,6-tetrahydro-2(1H)-pyrimidinone
DMSO=dimethylsulfoxide
EDC=1-ethyl-3-(3-dimethylaminopropyl) carbodiimide
ES MS=electrospray mass spectrometry
Et=ethyl
FAB HRMS=fast atom bombardment high resolution mass spectroscopy
FAB MS=fast atom bombardment mass spectroscopy
HOBt=1-hydroxy benzotriazole hydrate
HPLC=high performance liquid chromatography
i-Pr=isopropyl
Me=methyl
MsCl=methanesulfonyl chloride (or mesyl chloride)
NBS=N-bromosuccinimide
NIS=N-iodosuccinimide
NMR=nuclear magnetic resonance
Ph=phenyl
PMBCI=p-methoxybenzyl chloride
rt and RT=room temperature
TFA=trifluoroacetic acid
THF=tetrahydrofuran The compounds of the present invention can be readily prepared according to the following reaction schemes and examples, or modifications thereof, using readily available starting materials, reagents and conventional synthesis procedures. In these reactions, it is also possible to make use of variants which are themselves known to those of ordinary skill in this art, but are not mentioned in greater detail. Furthermore, other methods for preparing compounds of the invention will be readily apparent to the person of ordinary skill in the art in light of the following reaction schemes and examples. Unless otherwise indicated, all variables are as defined above.

The compounds of the present invention can be prepared by the coupling of suitable (poly)azanaphthenyl carboxylic acids (or acid derivatives such as acid halides or esters) with the appropriate amines, as represented by the following general scheme:

SCHEME 1

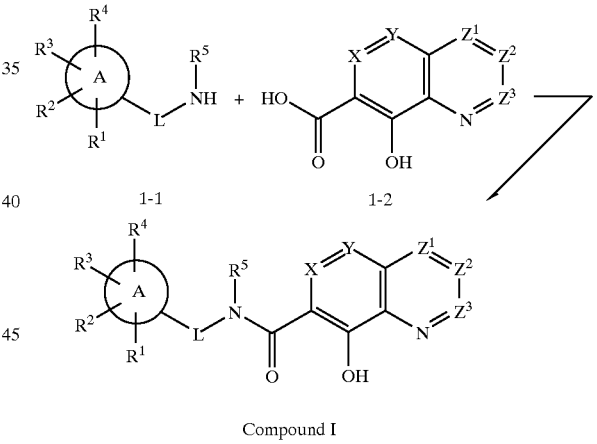

Compound I

Methods for coupling carboxylic acids with amines to form carboxamides are well known in the art. Suitable methods are described, for example, in Jerry March, *Advanced Organic Chemistry,* 3rd edition, John Wiley & Sons, 1985, pp. 370–376. Amines of formula 1-1 can be prepared using the methods described in Richard Larock, *Comprehensive Organic Transformations,* VCH Publishers Inc, 1989, pp 385–438, or routine variations thereof. Azanaphthenyl and polyazanaphthenyl carboxylic acids of formula 1-2 can be prepared using methods described in Ochiai et al., *Chem. Ber.* 1937, 70: 2018, 2023; Albert et al., *J. Chem. Soc.* 1952, 4985, 4991; and Barlin et al., *Aust. J. Chem.* 1990, 43: 1175–1181; or routine variations thereof. Schemes 2–16 below illustrate and expand upon the chemistry portrayed in Scheme 1.

In Scheme 2, following the procedure set forth in Ornstein et al., *J. Med. Chem.* 1989, 32: 827–833, a cyclic anhydride such as quinolinic anhydride (i.e., $Z^1=Z^2=Z^3=CH$ in 2-1) can be opened with isopropanol to provide mono acid 2-2, which can be converted to the corresponding acyl chloride 2-3 (e.g., by refluxing thionyl chloride). Acyl chloride 2-3 can then be reduced (e.g., with $NaBH_4$ or $LiBH_4$) to the corresponding alcohol 2-4, which can be converted to the corresponding bromide through the action of bromine in the presence of triphenylphosphine. Alkylation of the bromide with the sodium anion of phenylsulfonamide 2-5 in a polar aprotic solvent like DMF can provide sulfonamide 2-6, which can be treated with a base (e.g., alkali metal alkoxide such as sodium methoxide) to provide the bicyclic ester 2-7 via a Dieckmann cyclization.

Saponification of the ester (e.g., with aqueous NaOH at reflux) will afford the acid 2-8. The acid 2-8 can be activated with triphosgene and coupled with a variety of amines to provide the compounds of the invention 2-9.

The starting anhydrides of formula 2-1 can be prepared via methods described in Philips et al., *Justus Liebigs Ann. Chem.* 1895, 288: 2535; Bernthsen et al., *Chem. Ber.* 1887; 20: 1209; Bly et al., *J. Org. Chem.* 1964, 29: 2128–2135; and Krapcho et al., *J. Heterocycl. Chem.* 1993, 30: 1597–1606; or routine variations thereof.

SCHEME 2

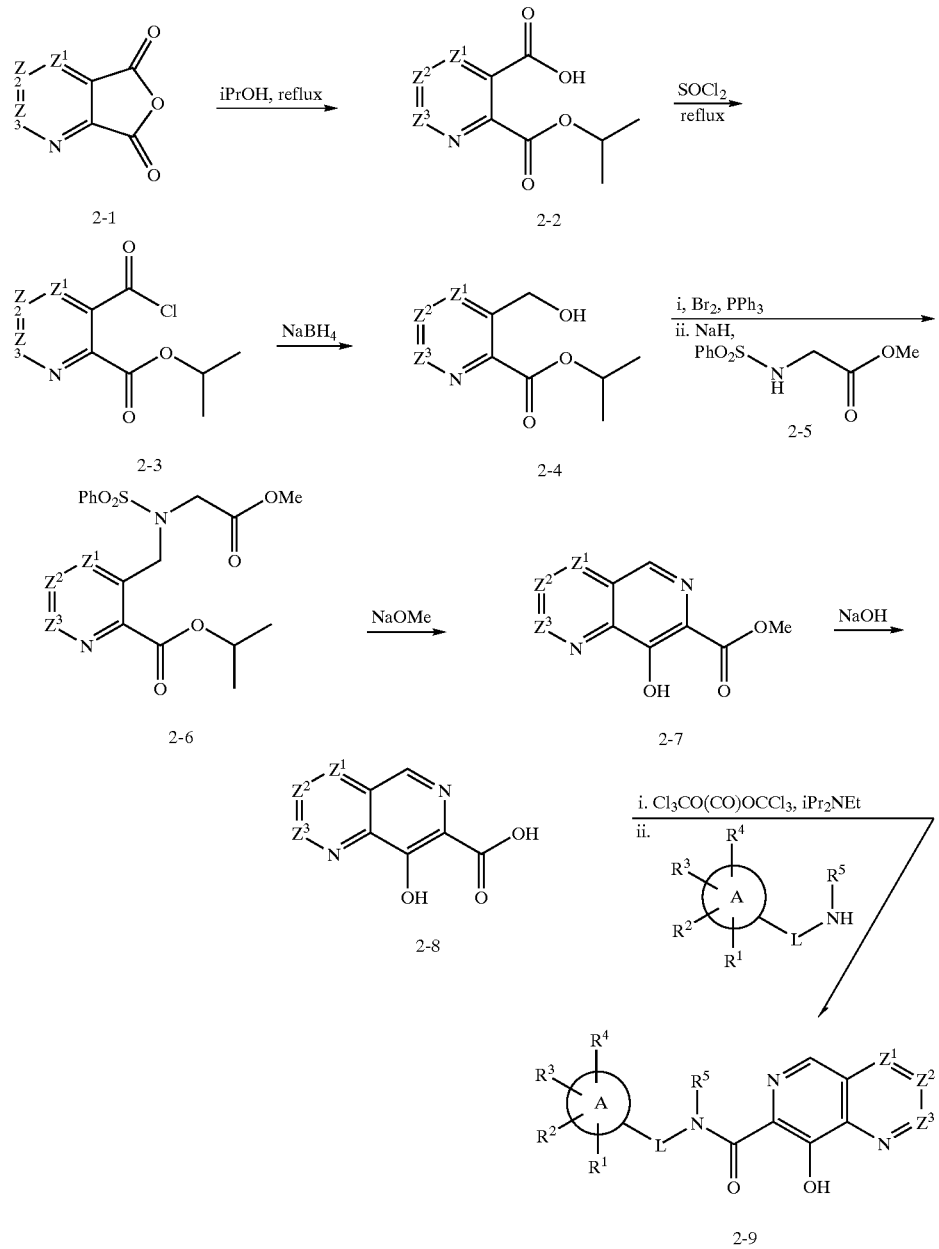

Scheme 3 depicts an alternative synthesis in which alcohol 2-4 can undergo the Mitsunobu reaction with the phenylsulfonamide of glycine methyl ester to provide 3-1. The sulfonamide 3-1 can again be elaborated to provide the acid 2-8, which can be coupled with a variety of amines using standard reagents to provide the compounds of the invention 2-9.

SCHEME 3
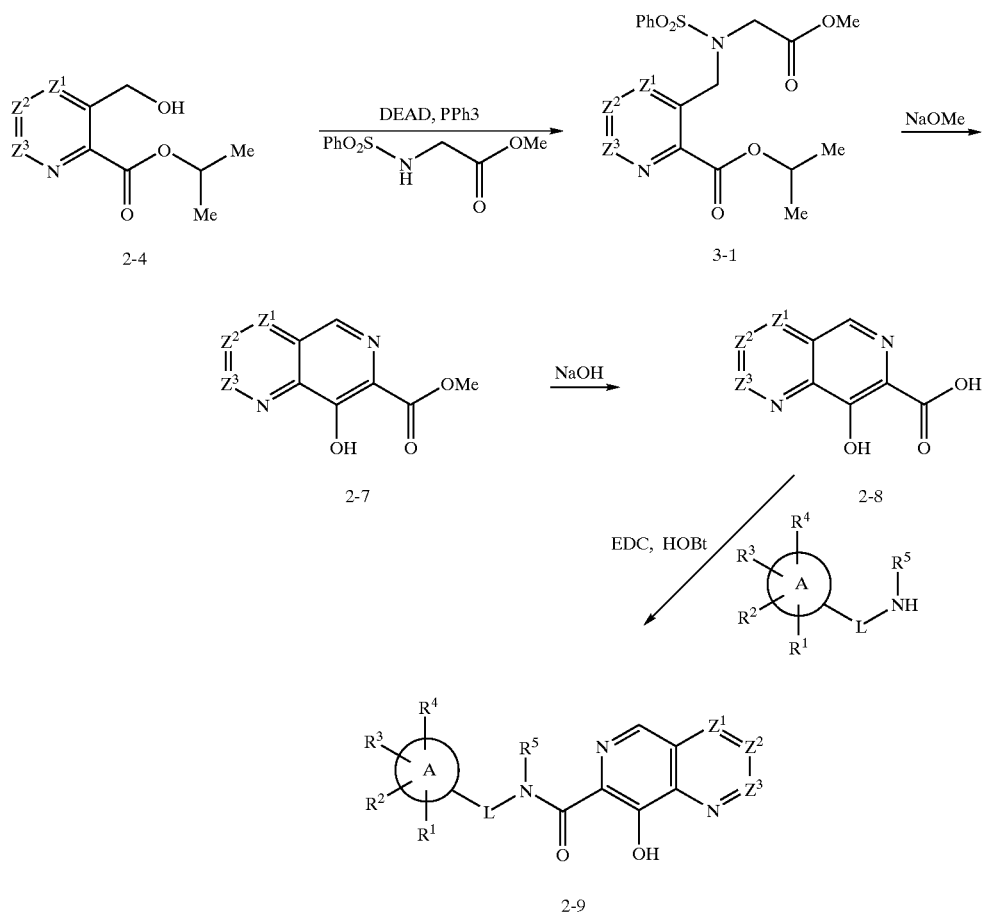
Scheme 3A depicts (for a napthyridine core) a variation of the synthesis shown in Scheme 3, wherein the acid 3A-2 is reacted with ethyl chloroformate to form the mixed anhydride 3A-3, which is reduced to alcohol 3A-4.
-continued
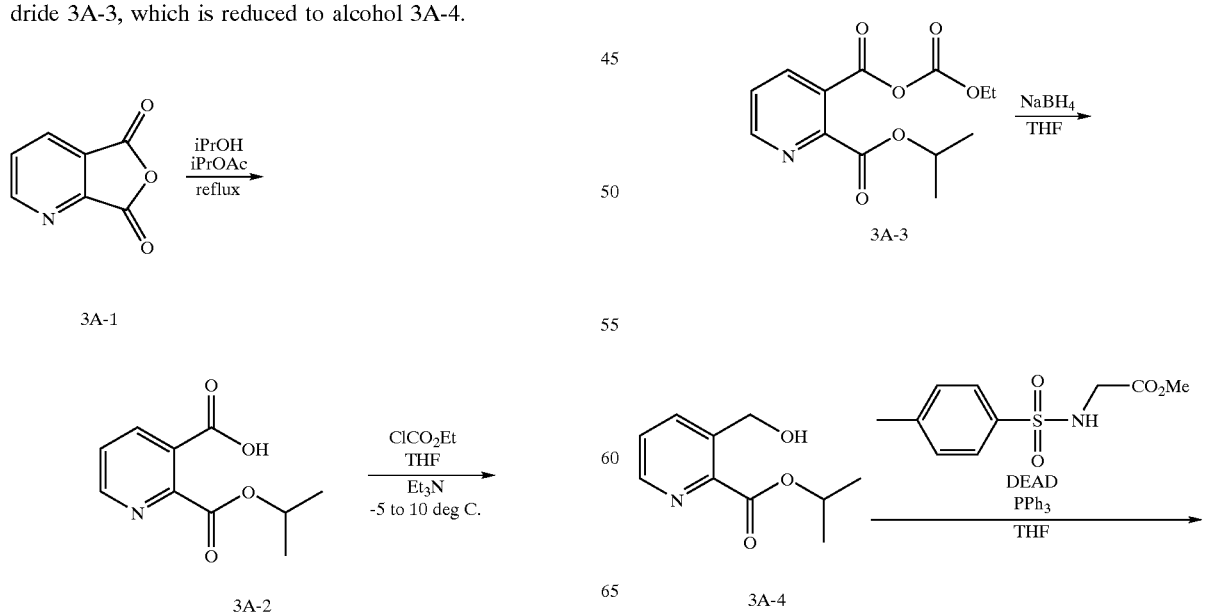

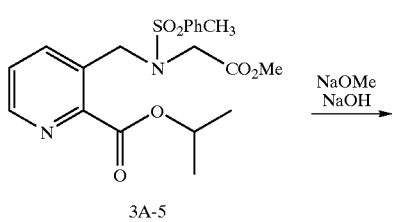

3A-5

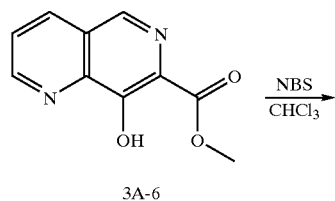

3A-6

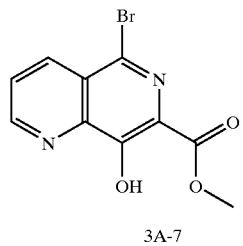

3A-7

Halogen substituted compounds of the present invention can be prepared as shown in Scheme 4. The acid chloride 2-3 can be reacted with glycine methyl ester to provide the amide 4-1. Dieckmann cyclization of the ester 4-1 with a sodium alkoxide base in an alcoholic solvent like methanol will provide phenol 4-2., which can be reacted with phosphorous oxychloride, followed by methanolysis of the intermediate phosphonate esters to provide 4-3. The ester bond of 4-3 can react selectively with suitable amines (e.g., 1-(1H-indol-2-yl)methanamine is depicted in Scheme 4) to provide the corresponding halogenated derivative 4-4.

SCHEME 4

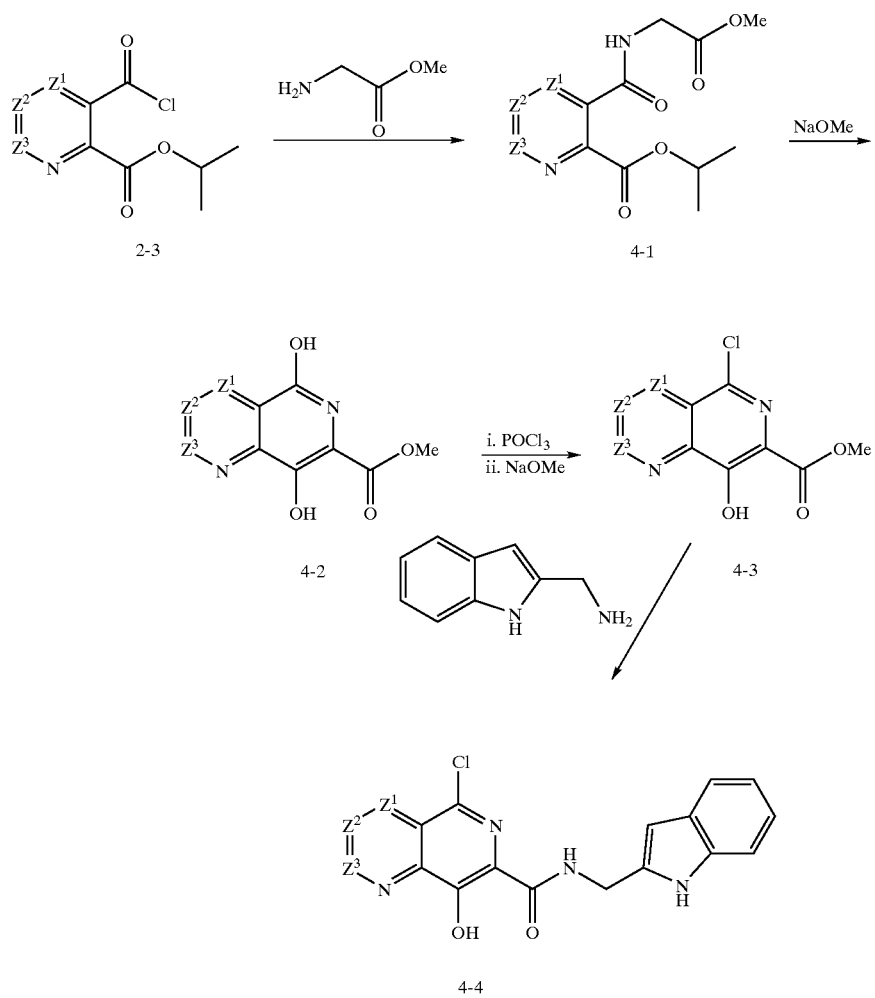

The preparation of compounds that feature additional substituents can be achieved as shown in Scheme 5. Oxidation of the alcohol 2-4 with manganese dioxide in an inert solvent such as methylene chloride will provide aldehyde 5-1. The addition of Grignard reagents (such as phenyl magnesium bromide) to aldehyde moiety 5-1 can occur regioselectively to provide the alcohol 5-2, which can then be elaborated to the compounds of the invention 5-6.

treated with bromine to undergo bromination at the 6 position to afford 6-2, which can be converted to the methoxypyridine 6-3 and then oxidized to the corresponding N-oxide 6-4. The N-oxide can be nitrated to provide 6-5. Reduction of 6-5 with iron in the presence of ammonium chloride can provide the aniline 6-6, which can be reacted with an alpha,beta-unsaturated aldehyde or ketone in the presence of an acid catalyst like sulfuric acid to provide 6-7 via an

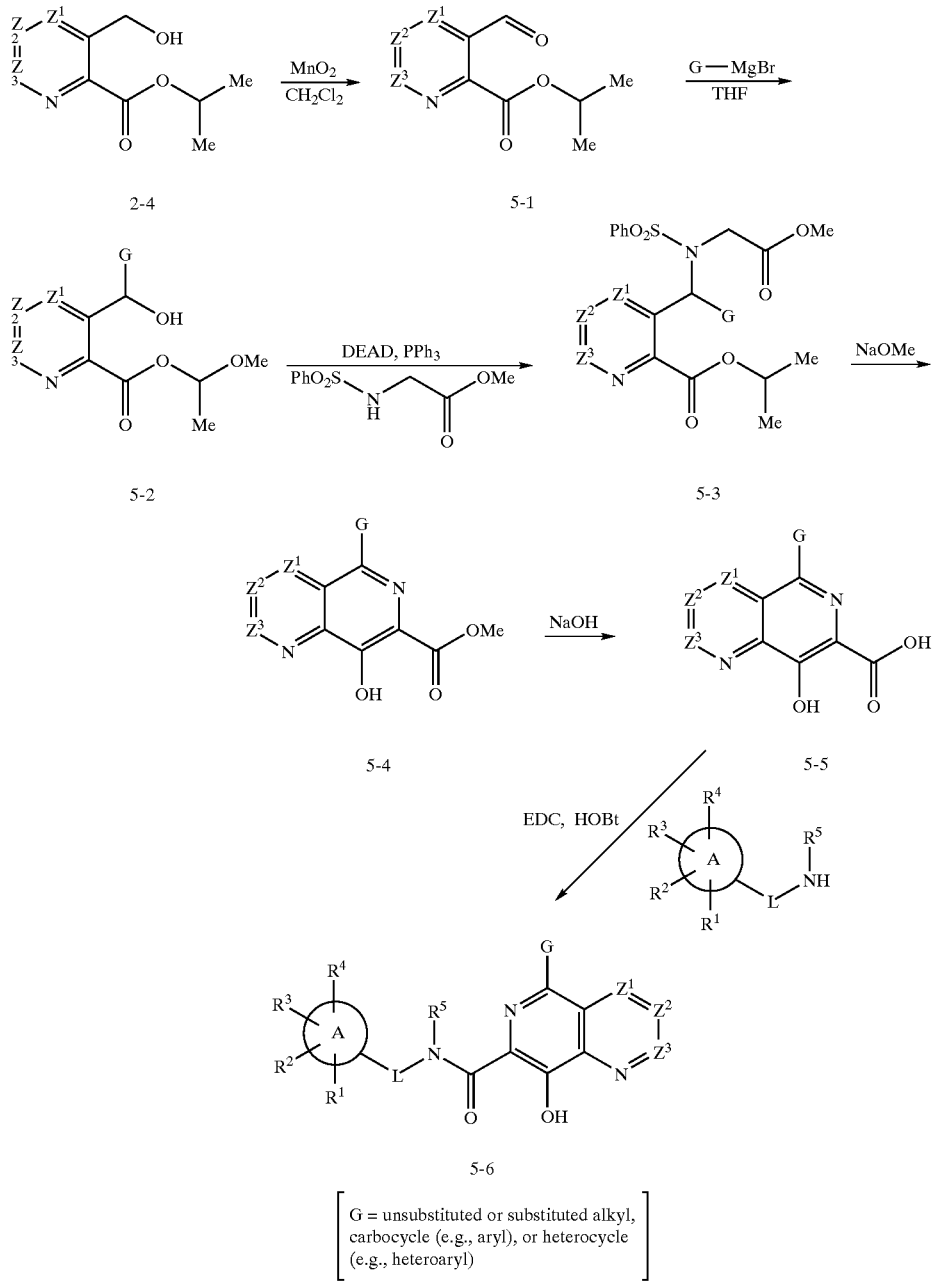

SCHEME 5

[G = unsubstituted or substituted alkyl, carbocycle (e.g., aryl), or heterocycle (e.g., heteroaryl)]

A further synthetic route to prepare compounds that are the subject of the invention is shown in Scheme 6. This methodology allows access to naphthyridine derivatives that are substituted at the 2, 3, 4 and 5 positions. Briefly, a 2-substituted 5-hydroxypyridine derivative 6-1 can be annulation. The bromide 6-7 can be elaborated to the amide 6-9 via a sequence of carbonylation and amidation reactions.

2-Substituted 5-hydroxypyridine derivatives of formula 6-1 can be prepared via methods described in Sorm et al., *Collect. Czech. Chem. Commun.* 1949, 14: 331,342; and Saksena et al., *Tetrahedron Lett.* 1993, 34: 3267–3270: or routine variations thereof.

SCHEME 6

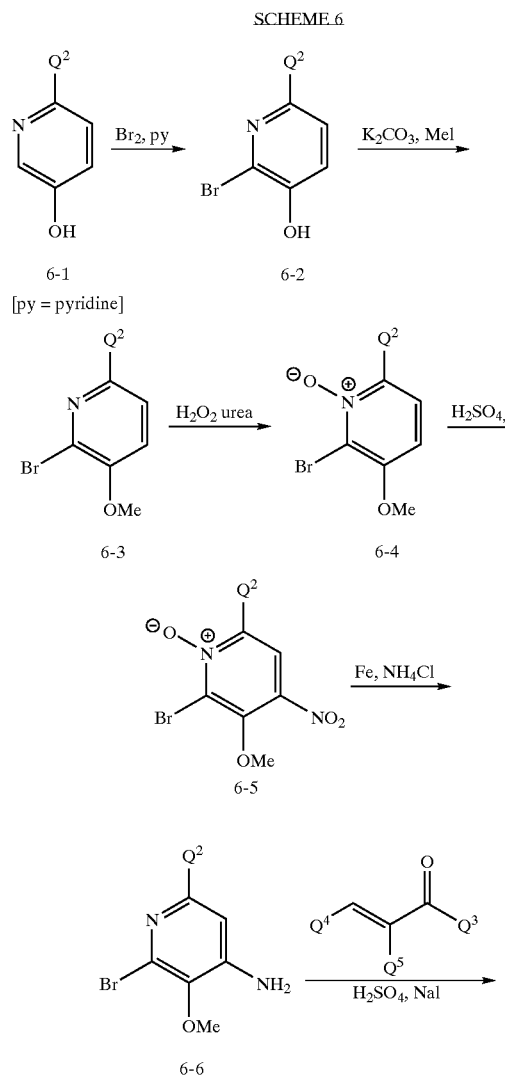

[py = pyridine]

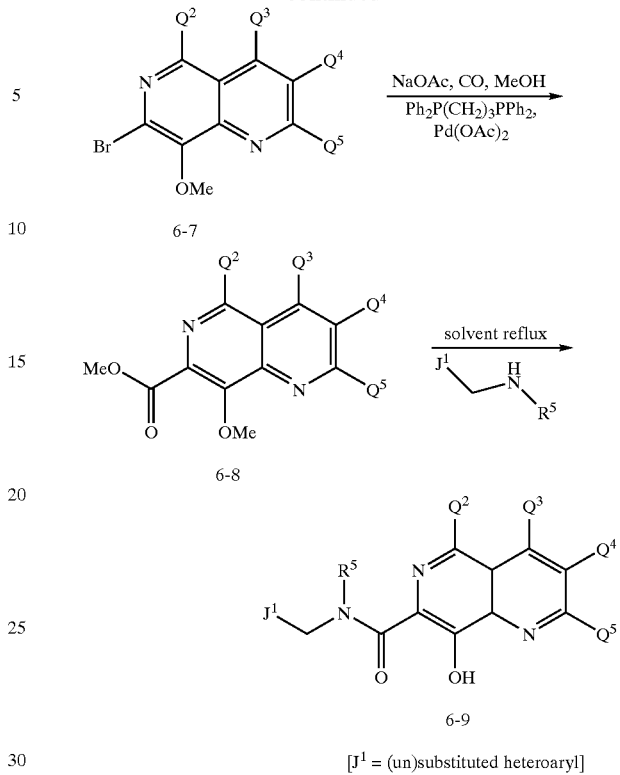

6-9

[$J^1$ = (un)substituted heteroaryl]

Compounds of the invention that comprise an amino substituent at the 5 position can be prepared in the manner set forth in Schemes 7 and 8. Bromination of the phenol 7-1 occurs regioselectively upon treatment with NBS in an inert solvent like methylene chloride to afford 7-2. Reaction of this bromide with an amine at elevated temperatures in the presence of a polar solvent such as DMPU affords compounds of the invention 7-3. Similar reaction of the bromide 7-2 (Scheme 8) with a diamine such as ethylene diamine in DMF as solvent will afford the formylated derivative 8-1 in addition to the expected diaminoethane derivative.

SCHEME 7

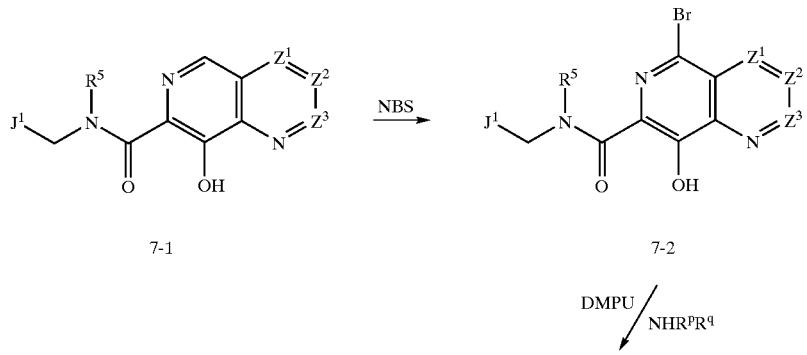

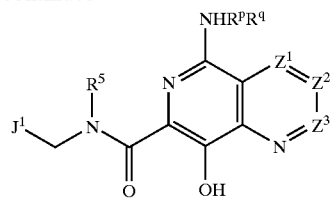

7-3

[J¹ = (un)substituted heteroaryl
Rᵖ, Rᵍ = H; alkyl; alkyl substituted with, e.g., OH, alkoxy, carbocycle, or heterocycle; (un)substituted carbocycle, or (un)substituted heterocycle]

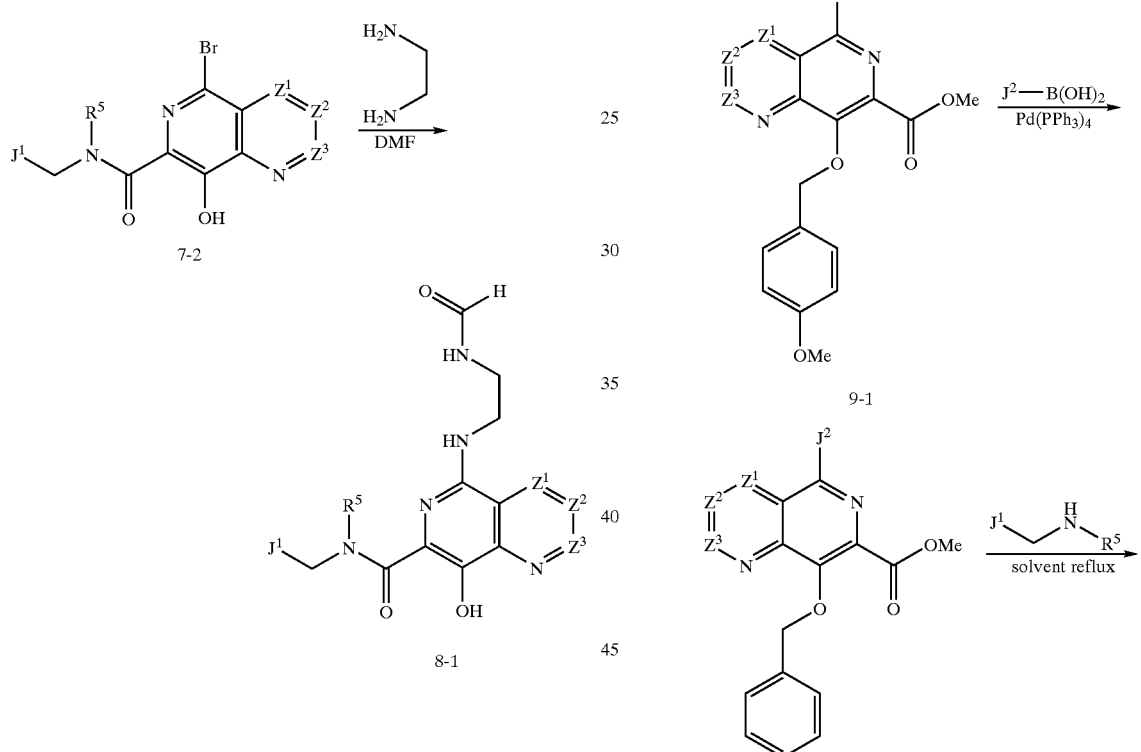

Preparation of aryl and heteroaryl derivatives via palladium cross coupling of the chloride 9-1 and the requisite boronic acids are depicted in Scheme 9.

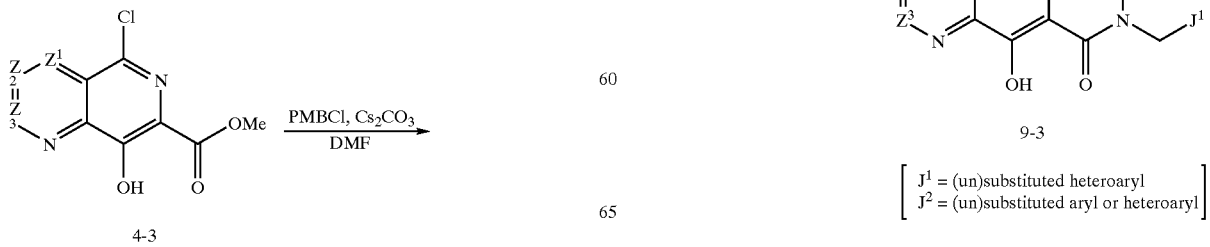

[J¹ = (un)substituted heteroaryl
J² = (un)substituted aryl or heteroaryl]

(Hetero)aryloxy, (hetero)arylamino, and (heteroaryl)thioxy derivatives 10-2, 11-2, and 12-2 respectively can be prepared as shown in Schemes 10 to 12, which exemplify the procedure for the naphthyridine core. The corresponding sulfone derivatives 12-2 can be obtained by oxidation of the sulfides 12-1 with either ozone or 3-chloroperbenzoic acid as shown in Scheme 12.

SCHEME 10

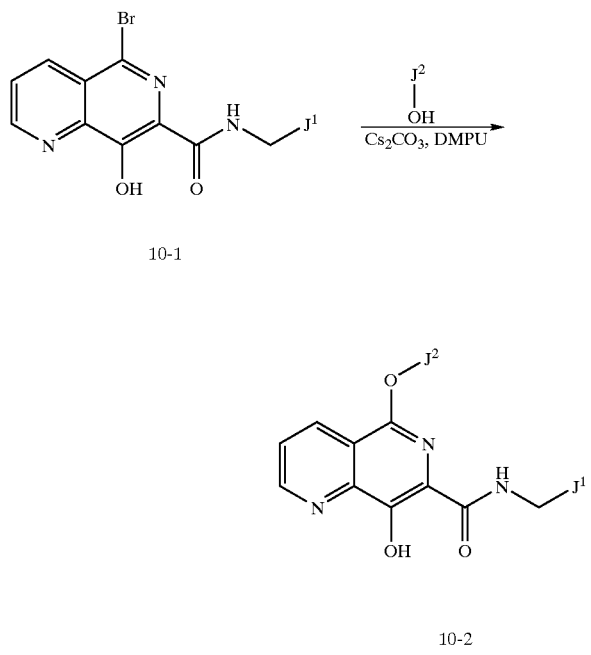

SCHEME 11

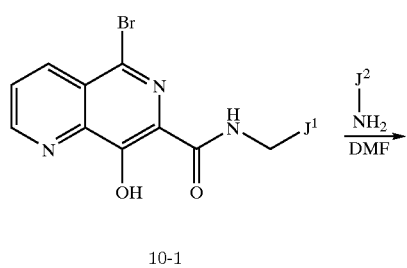

SCHEME 12

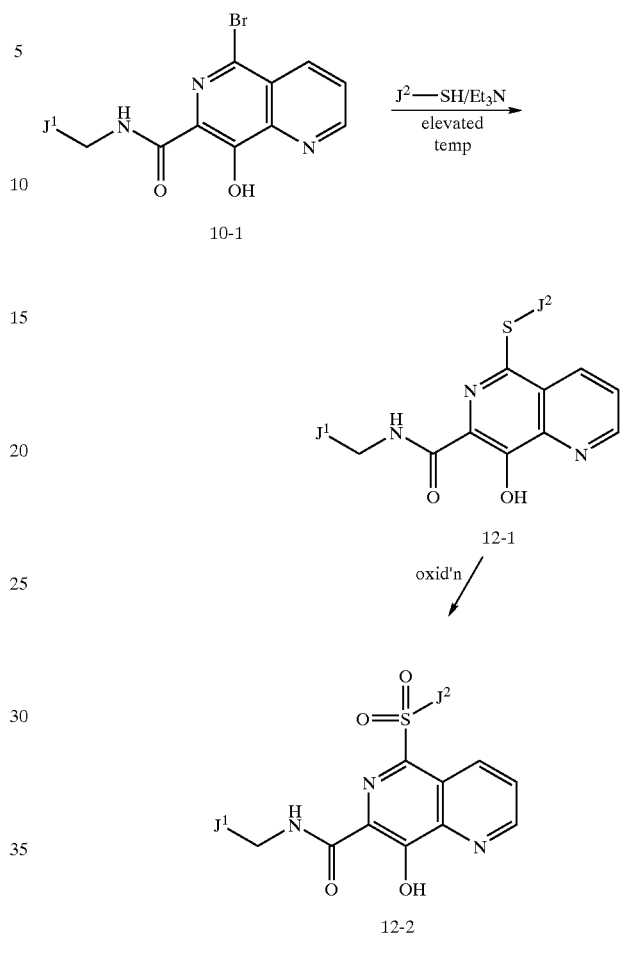

Preparation of compounds of the invention substituted with an acetylene can be prepared according to Scheme 13, which exemplifies the procedure for the naphthyridine core. Following protection of the iodide 13-2 as its benzoate 13-3, the acetylenic group (for example propynol) can be appended by employing a suitable palladium catalyst in the presence of copper iodide. Aminolysis of the ester 13-4 will afford the amide 13-5 with concomitant deprotection of the benzoate ester. Alternately the ester 13-4 can be converted to the corresponding amine and sulfone derivatives as shown in Schemes 14 and 15. Scheme 16 shows that the preparation of the nitrile derivative 16-2 can be achieved via a palladium catalyzed cyanation of the iodide 13-4.

SCHEME 13

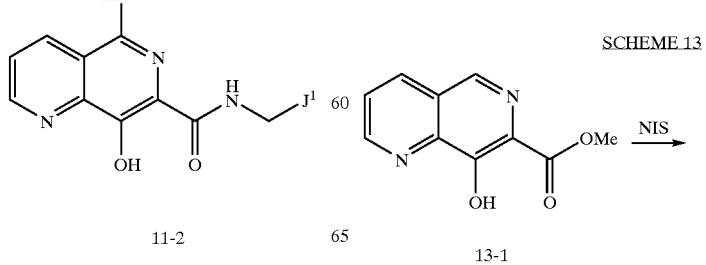

-continued
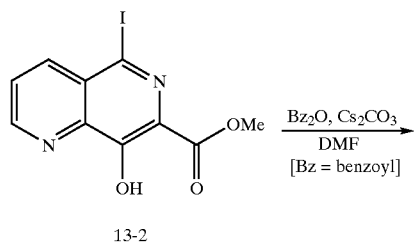
13-2
Bz₂O, Cs₂CO₃
DMF
[Bz = benzoyl]
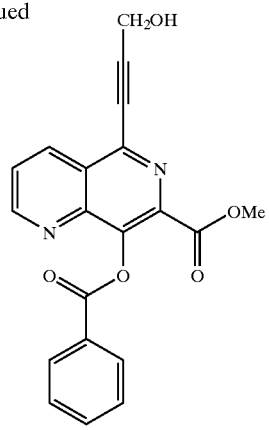
13-4
i. NaOH
ii. Triphosgene, NiPr₂Et
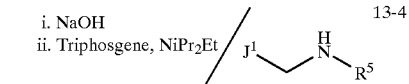
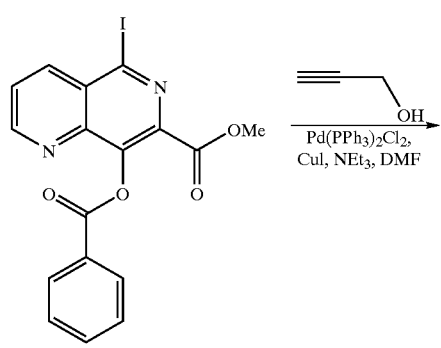
13-3
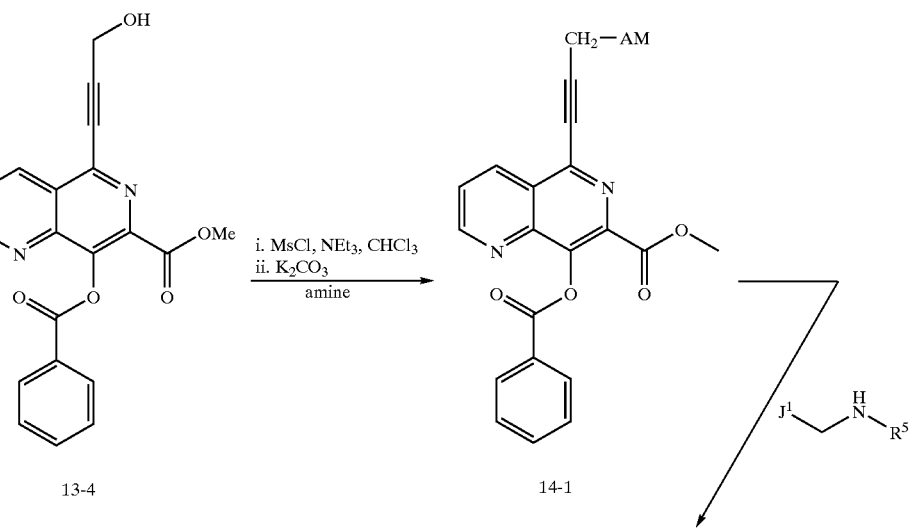
SCHEME 14
13-4 → i. MsCl, NEt₃, CHCl₃; ii. K₂CO₃, amine → 14-1

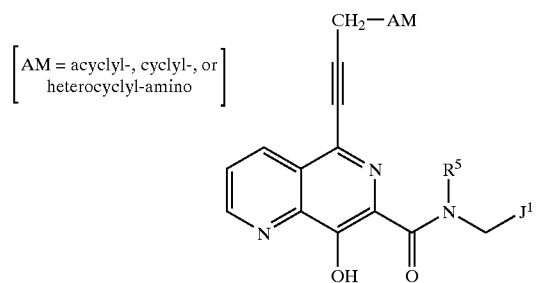
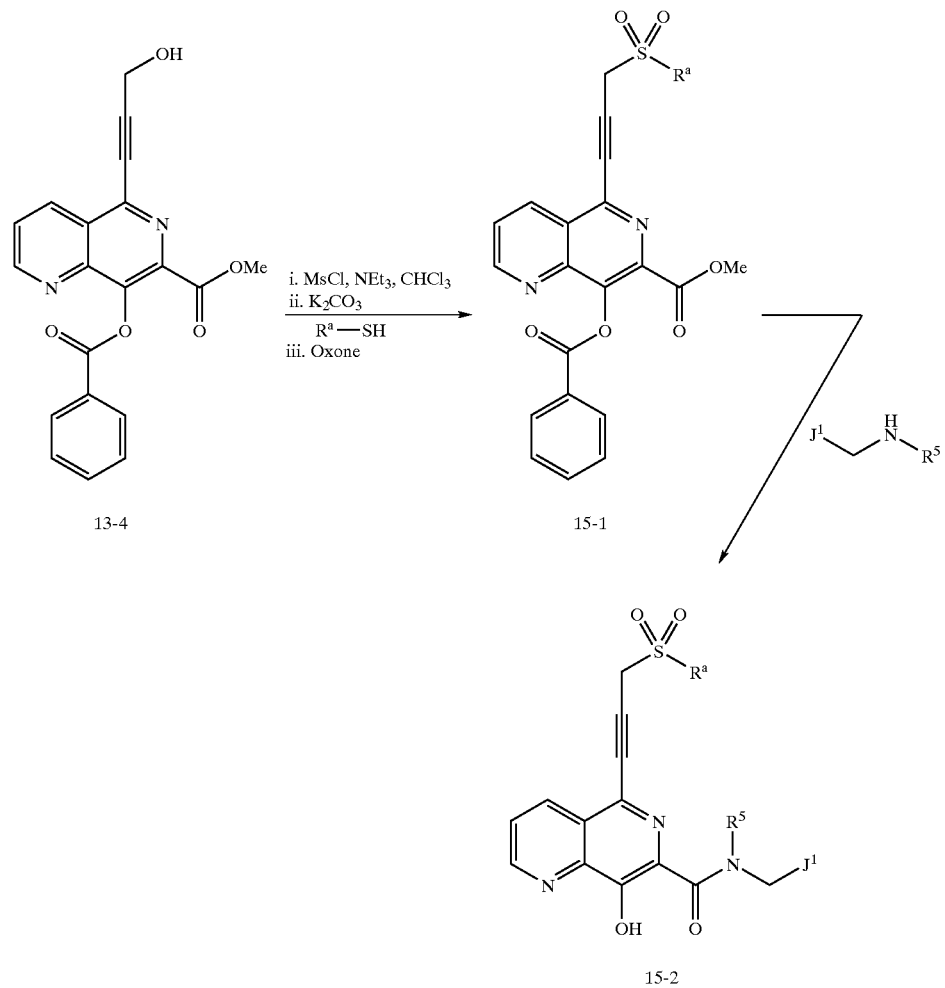
SCHEME 15

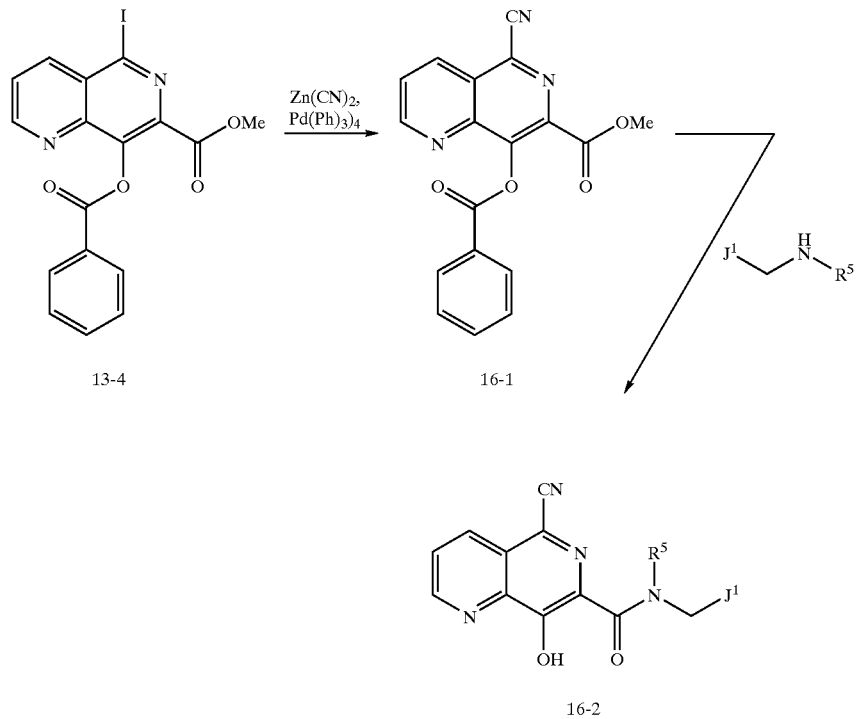

In the processes for preparing compounds of the present invention set forth in the foregoing schemes, functional groups in various moieties and substituents may be sensitive or reactive under the reaction conditions employed and/or in the presence of the reagents employed. Such sensitivity/reactivity can interfere with the progress of the desired reaction to reduce the yield of the desired product, or possibly even preclude its formation. Accordingly, it may be necessary or desirable to protect sensitive or reactive groups on any of the molecules concerned. Protection can be achieved by means of conventional protecting groups, such as those described in *Protective Groups in Organic Chemistry*, ed. J. F. W. McOmie, Plenum Press, 1973 and in T. W. Greene & P. G. M. Wuts, *Protective Groups in Organic Synthesis*, John Wiley & Sons, 1991. The protecting groups may be removed at a convenient subsequent stage using methods known in the art. Alternatively the interfering group can be introduced into the molecule subsequent to the reaction step of concern. For example, if one or more of the substituents $R^1$, $R^2$, $R^3$, and $R^4$ in compound 1-1 can interfere with the coupling reaction between compounds 1-1 and 1-2 of Scheme 1, the substituent can be incorporated into the molecule in a post-coupling step to afford Compound I.

The following examples serve only to illustrate the invention and its practice. The examples are not to be construed as limitations on the scope or spirit of the invention.

EXAMPLE 1

2-({[(8-hydroxy-1,6-naphthyridin-7-yl)carbonyl]amino}methyl)-1H-benzimidazole

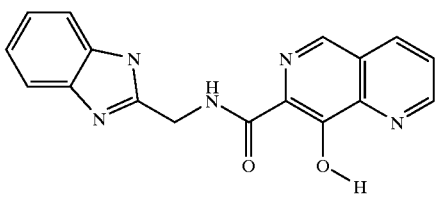

Step 1: Preparation of 3-{[Methoxycarbonylmethyl-(toluene-4-sulfonyl)-amino]-methyl}-pyridine-2-carboxylic acid isopropyl ester Isopropyl 3-(hydroxymethyl)pyridine-2-carboxylate (prepared in accordance with P. Ornstein et. al. *J. Med. Chem.* 1989, 32, 827) (200 g, 1.02 mol), methyl N-[(4-methylphenyl)sulfonyl]glycinate (249 g, 1.02 mol), and triphenylphosphine (403 g, 1.5 mol) were dissolved in dry THF (3000 mls) and cooled to zero degrees under N2. The diethylazodicarboxylate (DEAD) (267.6 g, 1.5 mol) was dissolved in dry THF (250 mls) and placed in a 500 ml addition funnel. The DEAD was added dropwise over 1 hour. The ice bath was removed and the reaction was allowed to warm slowly to RT. After 2 hours, the reaction was checked by HPLC (above conditions) and some glycinate remained. More starting reagents were added and the reaction was left to stir at RT. After 30 min, the reaction was checked again and saw a very small amount of the glycinate remaining. Concentrated reaction down to a reddish-orange oil that was carried onto the next step.

Step 2: Preparation of Methyl 8-hydroxy-1,6-naphthyridine-7-carboxylate

3-{[Methoxycarbonylmethyl-(toluene-4-sulfonyl)-amino]-methyl}-pyridine-2-carboxylic acid isopropyl ester (1.02 mol) was dissolved in dry methanol (4000 ml) and cooled to zero degrees under nitrogen. Then via addition funnel, sodium methoxide (137.8 g, 2.5 mol) was added slowly to avoid any exotherm. The reaction was stirred at zero degrees, and checked by HPLC after 1.5 hours and was found to be completed. The solvent was removed in vacuo to obtain a reddish-orange oil, which was partitioned between water (1L) and ethyl acetate (1L). The organic layer was back extracted with saturated sodium bicarbonate solution. The pH of the aqueous layer was adjusted to 7, and the layer was maintained at this pH while extracting with methylene chloride. The organic layer was dried with Na2SO4, filtered, and the solvent was removed in vacuo to obtain a tan solid. The solid was dissolved in hot ethyl acetate, and the solution was filtered while hot to filter out any insoluble material. The product precipitated upon cooling. The precipitate was then filtered and dried in a vacuum oven. The filtrate was recrystallized by concentrating the filtrate and redissolving the resulting solid in a minimal amount of methylene chloride. Sufficient ethyl acetate was added to turn the solution slightly cloudy, after which the solution was boiled to reduce the volume, cooled, and the resulting crystals were filtered out and dried in a vacuum oven.

1H NMR (CDCl3, 500 MHz) δ 11.794 (5H, s), 9.2 (1H, dd, J=1.7 and 6.1 Hz), 8.8 (1H, s), 8.3 (1H, dd, J=1.5 and 9.7 Hz), 7.7 (1H, dd, J=4.2 and 12.4 Hz), 4.1 (3H, s) ppm. ES MS exact mass calculated for $C_{10}H_8N_2O_3$ 204.1869 (MH+), found 205.1.

Step 3: Preparation of 8-hydroxy-1,6-naphthyridine-7-carboxylic acid

To a slurry of methyl 8-hydroxy-1,6-naphthyridine-7-carboxylate from Example 1, Step 2 (1.50 g, 7.35 mmol) in methanol (45 ml) was added lithium hydroxide (22.0 ml of a 1M aq. solution, 22.0 mmol) and the reaction was heated at 100° C. for 7 hrs. Upon cooling to room temperature, hydrochloric acid (22.0 ml of a 1M aq. solution, 22.0 mmol) was added and the reaction stirred for 16 hrs. The mixture was concentrated to a volume of 50 ml and neutralized with dilute NaHCO3 (pH=7) The resulting precipitate was collected by filtration and washed with water and dried in vacuo to afford the title compound.

FAB MS calcd for $C_9H_6N_2O_3$ 191 (MH+), found 191. $^1$H NMR (D6DMSO, 400 MHz) δ 9.20 (1H, m), 8.72 (1H, s), 8.58 (1H, m), 7.80 (1H, dd, J=8.3 and 4.2 Hz) ppm.

Step 4: Preparation of 2-({[(8-hydroxy-1,6-naphthyridin-7-yl)carbonyl]amino}methyl)-1H-benzimidazol-1-ium Trifluoroacetate Triphosgene (0.556 g, 1.87 mmol) was added over 20 mins to a solution of the acid from Step 1. (0.89 g, 4.68 mmol) and diisopropylethylamine 3.26 ml, 18.7 mmol) in DMF (22 ml) at 0° C. The dark solution was allowed to warm to room temperature and stirred a further 1 hr. 2-(ammoniomethyl)-1H-benzimidazol-1-ium dichloride hydrate (25.0 mg, 1.05 mmol) was treated with a portion of the above solution (0.58 ml, 0.07 mmol) and the resulting mixture was stirred at room temperature for 16 hrs. The solution was treated with TFA (0.025 ml) and purified by preparative HPLC. (Gilson semi preparative HPLC system and a YMC Combiprep Pro Column (50×20 mm I.D., C18, S-5 um, 120A) (available from Waters) eluting with 5–95% acetonitrile/water (0.1% TFA) at 15 ml/min) to afford the trifluoroacetate salt of the title compound after lyophilization.

$^1$H NMR (d6DMSO, 400 MHz) δ 10.03 (1H, m), 9.21 (1H, d, J=4.2 Hz), 9.00 (1H, s), 8.66 (1H, d, J=8.3 Hz), 7.85 (1H, dd, J=8.3 and 4.2 Hz), 7.80–7.65 (2H, m), 7.60–7.40 (2H, m), 5.05 (2H, d, J=4.9 Hz) ppm. FAB MS calcd for $C_{17}H_{13}N_5O_2$ 320 (MH+), found 320. FAB HRMS exact mass calcd for $C_{17}H_{13}N_5O_2$ 320.1142 (MH+), found 320.1145.

EXAMPLE 2

8-hydroxy-N-[2-(1H-indol-3-yl)ethyl]-1,6-naphthyridine-7-carboxamide

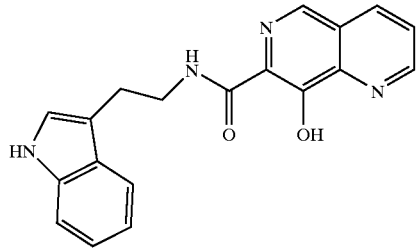

The title compound was prepared using the procedure described in Example 1, Step 4 replacing 2-(ammoniomethyl)-1H-benzimidazol-1-ium dichloride hydrate with 2-(1H-indol-3-yl)ethanamine.

$^1$H NMR (d6DMSO, 400 MHz) δ 10.85 (1H, s), 9.40 (1H, m), 9.16 (1H, dd, J=4.3 and 1.6 Hz), 8.90 (1H, s), 8.61 (1H, dd, J=8.2 and 1.6 Hz), 7.83 (1H, dd, J=8.2 and 4.2 Hz), 7.62 (1H, d, J=8.1 Hz), 7.34 (1H, d, J=7.8 Hz), 7.23 (1H, s), 7.07 (1H, t, J=7.5 Hz), 7.00 (1H, t, J=6.5 Hz), 3.66 (2H, m), 3.03 (2H, t, J=7.7 Hz) ppm. FAB MS calcd for $C_{19}H_{16}N_4O_2$ 333 (MH+), found 333.

EXAMPLE 3

N-{2-[2-(3,4-dimethoxyphenyl)-1H-indol-3-yl]ethyl}-8-hydroxy-1,6-naphthyridine-7-carboxamide

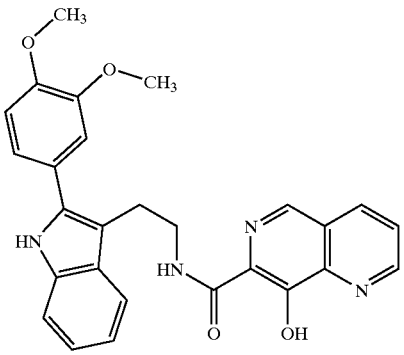

The title compound was prepared using the procedure described in Example 1, Step 4 replacing 2-(ammoniomethyl)-1H-benzimidazol-1-ium dichloride hydrate with 3-(2-aminoethyl)-2-(3,4-dimethoxyphenylindole).

¹H NMR (d₆DMSO, 400 MHz) δ 11.1 (1H, s), 9.55 (1H, m), 9.17 (1H, d, J=4.2 Hz), 8.89 (1H, s), 8.61 (1H, d, J=8.2 Hz), 7.84 (1H, dd, J=8.2 and 4.2 Hz), 7.74 (1H, d, J=8.1 Hz), 7.36 (1H, d, J=7.9 Hz), 7.26 (1H, d, J=8.2 Hz), 7.22 (1H, s), 7.10 (1H, t, J=7.6 Hz), 7.10–7.00 (2H, m), 3.73 (3H, s), 3.70–3.40 (2H, m), 3.18 (2H, t, J=7.9 Hz) ppm. FAB MS calcd for $C_{27}H_{24}N_4O_4$ 469 (MH⁺), found 469. FAB HRMS exact mass calcd for $C_{27}H_{24}N_4O_4$ 469.1870317 (MH⁺), found 469.1871720.

EXAMPLE 4

8-hydroxy-N-[(2-oxo-2,3-dihydro-1H-indol-3-yl)methyl]-1,6-naphthyridine-7-carboxamide

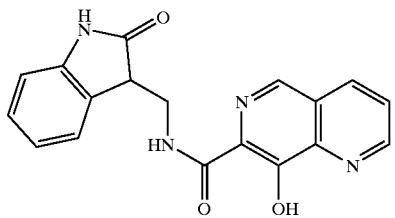

The title compound was prepared using the procedure described in Example 1, Step 4 replacing 2-(ammoniomethyl)-1H-benzimidazol-1-ium dichloride hydrate with 3-(aminomethyl)-1,3-dihydro-2H-indol-2-one.

¹H NMR (d₆DMSO, 400 MHz) δ 10.4 (1H, s), 9.54 (1H, m), 9.18 (1H, d, J=4.3 Hz), 8.92 (1H, s), 8.63 (1H, d, J=8.3 Hz), 7.84 (1H, dd, J=8.3 and 4.3 Hz), 7.22 (2H, t, J=7.4 Hz), 6.96 (2H, t, J=7.4 Hz), 5.48 (1H, m), 3.03 (1H, dd, J=16.0 and 10.3 Hz), 2.75 (1H, dd, J=16.0 and 6.0 Hz) ppm. FAB MS calcd for $C_{18}H_{14}N_4O_3$ 335 (MH⁺), found 335. FAB HRMS exact mass calcd for $C18H_{14}N_4O_3$ 335.1139 (MH⁺), found 335.1143

EXAMPLE 5

8-hydroxy-N-[2-(10H-phenothiazin-10-yl)ethyl]-1,6-naphthyridine-7-carboxamide

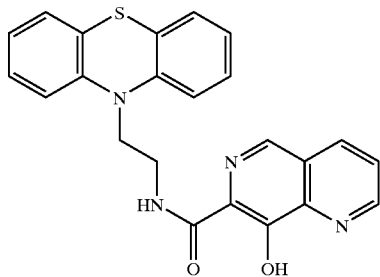

The title compound was prepared using the procedure described in Example 1, Step 4 replacing 2-(ammoniomethyl)-1H-benzimidazol-1-ium dichloride hydrate with 2-(10H-phenothiazin-10-yl)ethanamine.

¹H NMR (d₆DMSO, 400 MHz) δ 9.55 (1H, t, J=6.2 Hz), 9.18 (1H, dd, J=4.2 and 1.6 Hz), 8.93 (1H, s), 8.62 (1H, dd, J=8.4 and 1.6 Hz), 7.84 (1H, dd, J=8.4 and 4.2 Hz), 7.65–7.40 (4H, m), 7.15 (2H, m), 6.96 (2H, m), 4.09 (2H, m), 3.74 (2H, m) ppm. FAB MS calcd for $C_{23}H_{18}N_4O_2S$ 415 (MH⁺), found 415. FAB HRMS exact mass calcd for $C_{23}H_{18}N_4O_2S$ 415.1223 (MH⁺), found 415.1224.

EXAMPLE 6

8-hydroxy-N-[2-(2-methyl-1-phenyl-1H-indol-3-yl)ethyl]-1,6-naphthyridine-7-carboxamide

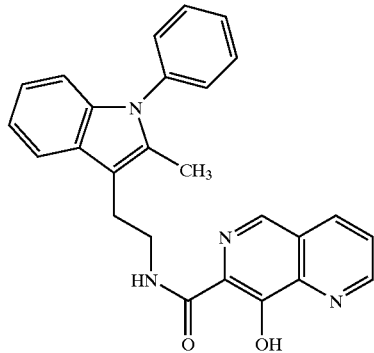

The title compound was prepared using the procedure described in Example 1, Step 4 replacing 2-(ammoniomethyl)-1H-benzimidazol-1-ium dichloride hydrate with 2-(2-methyl-1-phenyl-1H-indol-3-yl)ethanamine.

¹H NMR (d₆DMSO, 400 MHz) δ 9.47 (1H, t, J=6.0 Hz), 9.17 (1H, dd, J=4.2 and 1.6 Hz), 8.92 (1H, s), 8.62 (1H, dd, J=8.4 and 1.6 Hz), 7.84 (1H, dd, J=8.4 and 4.2 Hz), 7.67 (1H, d, J=6.9 Hz), 7.59 (2H, t, J=7.8 Hz), 7.48 (1H, t, J=7.2 Hz), 7.41 (2H, d, J=7.2 Hz), 7.20–6.95 (3H, m), 3.80–3.20 (2H, m), 3.08 (2H, t, J=7.3 Hz) 2.24 (3H, s) ppm. FAB MS calcd for $C_{26}H_{22}N_4O_2$ 423 (MH⁺), found 423. FAB HRMS exact mass calcd for $C_{26}H_{22}N_4O_2$ 423.1804 (MH⁺), found 423.1804.

EXAMPLE 7

8-hydroxy-N-(1H-indol-6-ylmethyl)-1,6-naphthyridine-7-carboxamide

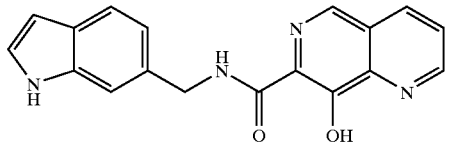

The title compound was prepared using the procedure described in Example 1, Step 4 replacing 2-(ammoniomethyl)-1H-benzimidazol-1-ium dichloride hydrate with 1-(1H-indol-6-yl)methanamine.

¹HNMR (d₆DMSO, 400 MHz) δ 11.00 (1H, s), 9.79 (1H, m), 9.17 (1H, d, J=4.2 Hz), 8.91 (1H, s), 8.61 (1H, d, J=8.3 Hz), 7.83 (1H, dd, J=8.3 and 4.2 Hz), 7.49 (1H, d, J=8.3 Hz), 7.42 (1H, s), 7.30 (1H, s), 7.06 (1H, d, J=8.1 Hz), 6.38 (1H, s), 4.64 (2H, d, J=6.3 Hz) ppm. FAB MS calcd for $C_{18}H_{14}N_4O_2$ 319 (MH⁺), found 319.

EXAMPLE 8

8-hydroxy-N-(1H-indol-2-ylmethyl)-1,6-naphthyridine-7-carboxamide

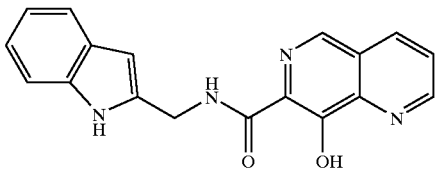

The title compound was prepared using the procedure described in Example 1, Step 4 replacing 2-(ammoniomethyl)-1H-benzimidazol-1-ium dichloride hydrate with 1-(1H-indol-2-yl)methanamine.

$^1$H NMR (d$_6$DMSO, 400 MHz) δ 11.00 (1H, s), 9.73 (1H, m), 9.17 (1H, m), 8.94 (1H, s), 8.61 (1H, d, J=8.2 Hz), 7.84 (1H, dd, J=8.2 and 4.2 Hz), 7.46 (1H, d, 7.9 Hz), 7.36 (1H, d, J=8.1 Hz), 7.04 (1H, t, J=8.0 Hz), 6.95 (1H, t, J=7.4 Hz), 6.33 (1H, s), 4.73 (2H, d, J=6.2 Hz) ppm. FAB MS calcd for C$_{18}$H$_{14}$N$_4$O$_2$ 319 (MH$^+$), found 319.

EXAMPLE 9

8-hydroxy-N-[(4-oxo-3,4-dihydrophthalazin-1-yl)methyl]-1,6-naphthyridine-7-carboxamide

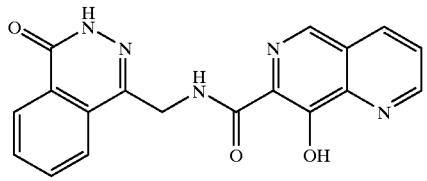

The title compound was prepared using the procedure described in Example 1, Step 4 replacing 2-(ammoniomethyl)-1H-benzimidazol-1-ium dichloride hydrate with 4-(aminomethyl)phthalazin-1(2H)-one.

$^1$H NMR (d$_6$DMSO, 400 MHz) δ 9.68 (1H, m), 9.18 (1H, dd, J=1.5 and 4.2 Hz), 8.94 (1H, s), 8.62 (1H, dd, J=8.2 and 1.5 Hz), 8.30 (1H, d, J=7.5 Hz), 8.17 (1H, d, J=9.0 Hz), 7.99 (1H, t, J=7.7 Hz), 7.84 (1H, dd, J=7.2 and 4.0 Hz), 4.95 (2H, m) ppm. FAB MS calcd for C$_{18}$H$_{13}$N$_5$O$_3$ 319 (MH$^+$), found 348.

EXAMPLE 10 tert-butyl 3-({[(8-hydroxy-1,6-naphthyridin-7-yl)carbonyl]amino}methyl)-1H-indole-1-carboxylate

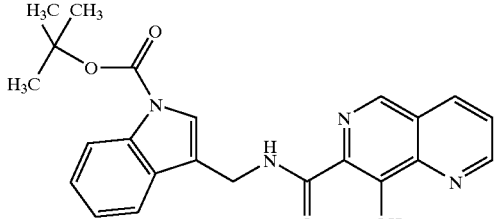

The title compound was prepared using the procedure described in Example 1, Step 4 replacing 2-(ammoniomethyl)-1H-benzimidazol-1-ium dichloride hydrate with tert-butyl 3-(aminomethyl)-1H-indole-1-carboxylate.

$^1$H NMR (d$_6$DMSO, 400 MHz) δ 9.70 (1H, m), 9.16 (1H, dd, J=1.7 and 4.3 Hz), 8.90 (1H, s), 8.60 (1H, dd, J=8.2 and 1.7 Hz), 8.05 (1H, d, J=8.3 Hz), 7.85 (1H, d, J=9.5 Hz), 7.82 (1H, dd, =4.2 and 8.3 Hz), 7.66 (1H, s), 7.33 (1H, t, J=8.4 Hz), 7.20 (1H, t, J=7.3 Hz), 4.69 (2H, m) ppm. FAB MS calcd for C$_{23}$H$_{22}$N$_4$O$_4$ 319 (MH$^+$), found 419.

EXAMPLE 11

8-hydroxy-N-(1H-indol-3-ylmethyl)-1,6-naphthyridine-7-carboxamide

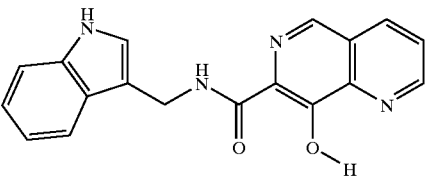

A solution of tert-butyl 3-({[(8-hydroxy-1,6-naphthyridin-7-yl)carbonyl]amino}methyl)-1H-indole-1-carboxylate from Example 10 (12.0 mg, 0.0029 mmol) in CH$_2$Cl$_2$ (1 ml) was treated with trifluroacetic acid (TFA) (1 ml) and resulting mixture was stirred at room temperature for 1 hr and then the solvent was evaporated in vacuo. The resulting material was dissolved in DMSO (1 ml) and aged for 24 hrs at room temperature. This solution was purified by preparative HPLC. (Gilson semi preparative HPLC system and a YMC Combiprep Pro Column (50×20 mm I.D., C18, S-5 um, 120A) eluting with 5–95% acetonitrile/water (0.1% TFA) at 15 min/min) to afford the title compound after lyophilization.

$^1$H NMR (d$_6$DMSO, 400 MHz) δ 10.98 (1H, s), 9.49 (1H, m) 9.15 (1H, d, J=4.2 Hz), 8.85 (1H, s), 8.58 (1H, d, J=8.3 Hz), 7.81 (1H, dd, J=8.3 and 4.2 Hz), 7.75 (1H, dd, J=7.7 Hz), 7.40–7.30 (2H, m), 7.08 (1H, t, J=7.0 Hz), 7.00 (1H, t, J=7.0 Hz), 4.71 (2H, d, J=6.0 Hz) ppm. FAB MS calcd for C$_{18}$H$_{14}$N$_4$O$_2$ 319 (MH$^+$), found 319.

EXAMPLE 12

6-({[(8-hydroxy-1,6-naphthyridin-7-yl)carbonyl]amino}methyl)-2,3-dihydroimidazo[2,1-b][1,3]thiazole

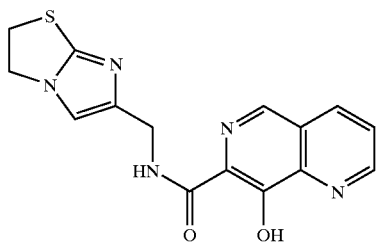

The title compound was prepared as the imidazothiazol-4-ium trifluoroacetate salt using the procedure described in Example 1, Step 4 replacing 2-(ammoniomethyl)-1H-benzimidazol-1-ium dichloride hydrate with 1-(2,3-dihydroimidazo[2,1-b][1,3]thiazol-6-yl)methanamine.

$^1$H NMR (d$_6$DMSO, 400 MHz) δ 9.67 (1H, t, J=6.9 Hz), 9.17 (1H, dd, J=4.2 and 1.6 Hz), 8.92 (1H, s), 8.62 (1H, dd, J=8.2 and 1.6 Hz), 7.85 (1H, dd, J=8.2 and 4.2 Hz), 7.47 (1H, s), 4.50 (2H, d, J=6.0 Hz) 4.32 (2H, t, J=7.5 Hz), 4.02 (2H, t, J=7.5 Hz) ppm. FAB MS calcd for $C_{15}H_{13}N_5O_2S$ 328 (MH$^+$), found 328. FAB HRMS exact mass calcd for $C_{15}H_{13}N_5O_2S$ 328.0863 (MH$^+$), found 328.085.

EXAMPLE 13

8-hydroxy-N-(4-pyridinylmethyl)[1,6]naphthyridine-7-carboxamide

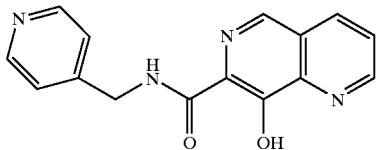

To a solution of methyl 8-hydroxy-1,6-naphthyridine-7-carboxylate from Example 1, Step 2 (0.05 g, 0.245 mmol) in dry toluene (3 mL) was added 1-pyridin-4-ylmethanamine (0.029 g, 0.270 mmol) and the mixture was heated to reflux for 16 hours. The solution was reduced to a smaller volume and refluxed for 4 additional hours. The solvent was removed under reduced pressure and the residue redissolved in DMF and filtered and the solution solution was purified by preparative HPLC (Gilson semipreparative HPLC system and a YMC Combiprep Column (50×20 mm I.D., C18, S-5 uM, 120 A) eluting with 5–95% acetonitrile/water (0.1% TFA) at 15 ml/min) to afford the title compound after lyophilization.

$^1$H NMR (d$_6$DMSO, 400 MHz) δ 10.07 (1H, m), 9.18 (1H, m), 8.97 (1H, d, J=1.47 Hz), 8.75 (2H, dd, J=5.0 Hz), 8.64 (1H, dd, J=8.3 Hz), 7.86 (1H, m), 7.77 (2H, d, J=5.1 Hz), 4.76 (2H, d, J=4.6 Hz) ppm. FAB MS calcd for $C_{15}H_{12}N_4O_2$ 281 (H$^+$), found 281. FAB HRMS exact mass calcd for $C_{15}H_{12}N_4O_2$ 281.1033 (MH$^+$), found 281.1032. Anal. Calcd for $C_{15}H_{12}N_4O_2$·1.25 TFA·1.00H$_2$O: C, 47.68; H, 3.49; N, 12.71. Found: C, 47.68; H, 3.70; N, 12.03.

EXAMPLE 14

8-hydroxy-N-(2-pyridinylmethyl)[1,6]naphthyridine-7-carboxamide

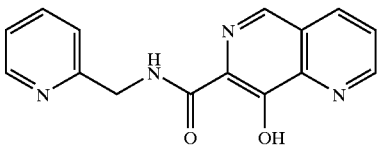

To a solution of methyl 8-hydroxy-1,6-naphthyridine-7-carboxylate from Example 1, Step 2 (0.05 g, 0.245 mmol) in dry toluene (3 mL) was added 1-pyridin-2-ylmethanamine (0.029 g, 0.270 mmol) and the mixture was heated to reflux for 16 hours. The solution was reduced to a smaller volume and refluxed for 4 additional hours. The solvent was removed under reduced pressure and the residue redissolved in DMF and filtered and the solution was purified by preparative HPLC (Gilson semipreparative HPLC system and a YMC Combiprep Column (50×20 mm I.D., C18, S-5 uM, 120 A) eluting with 5–95% acetonitrile/water (0.1% TFA) at 15 ml/min) to afford the title compound after lyophilization.

$^1$H NMR (d$_6$DMSO, 400 MHz) δ 9.88 (1H, m), 9.18 (1H, m), 8.96 (1H, d, J=1.1 Hz), 8.63 (2H, m), 7.96 (1H, dd, J=7.6 Hz), 7.86 (1H, m), 7.55 (1H, d, J=7.6 Hz), 7.46 (1H, dd, J=5.3 Hz), 4.76 (2H, d, J=4.6 Hz) ppm. FAB MS calcd for $C_{15}H_{12}N_4O_2$ 281 (H$^+$), found 281. FAB HRMS exact mass calcd for $C_{15}H_{12}N_4O_2$ 281.1033 (MH$^+$), found 281.1040. Anal. Calcd for $C_{15}H_{12}N_4O_2$·1.45 TFA·0.1H$_2$O: C, 48.05; H, 3.08; N, 12.52. Found: C, 48.04; H, 3.29; N, 12.17.

EXAMPLE 15

N-[2-(1H-Indol-3-yl)ethyl]8-hydroxyquinoline-7-carboxamide

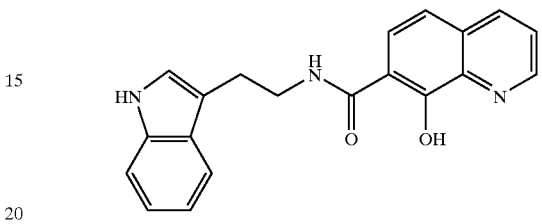

A mixture of 8-hydroxyquinoline-7-carboxylic acid (0.23 g, 1.25 mmol), 2-(1H-Indol-3-yl)ethylamine (0.20 g, 1.25 mmol), 1-hydroxybenzotriazole (0.18 g, 1.37 mmol), 1-(3-dimethylaminopropyl)-3-ethylcarbodiimide hydrochloride (0.26 g, 1.37 mmol), and triethylamine (0.7 mL, 4.99 mmol) in DMF (12 mL) was stirred at room temp overnight. The reaction mixture was concentrated under vacuum. The residue was dissolved in DMSO and subjected to HPLC purification on C-18 stationary phase eluted with water/acetonitrile/TFA mobile phase. Collection and lyophilization of appropriate fractions provide the title compound as yellow solid.

$^1$H NMR (400 MHz, DMSO-d$_6$) δ 10.82 (s, 1H), 9.08 (br s, 1H), 8.92 (br s, 1H), 8.42 (br d, 1H), 8.02 (d, 1H), 7.70 (br m, 1H), 7.61 (d, 1H), 7.46 (d, 1H), 7.34 (d, 1H), 7.22 (d, 1H), 7.07 (t, 11), 7.00 (t, 1H), 3.67 (q, 2H), 3.02 (t, 2H).

EXAMPLE 16

Oral Composition

As a specific embodiment of an oral composition of a compound of this invention, 50 mg of compound of Example 1 is formulated with sufficient finely divided lactose to provide a total amount of 580 to 590 mg to fill a size 0 hard gelatin capsule.

EXAMPLE 17

HIV Integrase Assay: Strand Transfer Catalyzed by Recombinant Integrase

Assays for the strand transfer activity of integrase were conducted in accordance with Wolfe, A. L. et al., *J. Virol.* 1996, 70: 1424–1432, for recombinant integrase, except that: (i) the assays used preassembled integrase strand transfer complexes; (ii) the strand transfer reaction was performed in the presence of inhibitor in 2.5 mM MgCl$_2$ using 0.5 to 5 nM of a 3'FITC labeled target DNA substrate (SEQ. ID. NO: 1 and SEQ. ID. NO: 2)

```
5'      TGA CCA AGG GCT AAT TCA CT fitc    3'
3' fitc    ACT GGT TCC CGA TTA AGT GA      5';
``` and (iii) strand transfer products were detected using an alkaline phosphatase conjugated anti-FITC antibody and a chemiluminescent alkaline phosphatase substrate. Representative compounds tested in the integrase assay demonstrated $IC_{50}$'s of less than about 100 micromolar.

Further description on conducting the assay using preassembled complexes is found in Hazuda et al., *J. Virol.* 1997, 71: 7005–7011; Hazuda et al., *Drug Design and Discovery* 1997, 15: 17–24; and Hazuda et al., *Science* 2000, 287: 646–650.

EXAMPLE 18

Assay for Inhibition of HIV Replication

Assays for the inhibition of acute HIV infection of T-lymphoid cells were conducted in accordance with Vacca, J. P. et al., (1994), Proc. Natl. Acad. Sci. USA 91, 4096. Representative compounds tested in the present assay demonstrated $IC_{95}$'s of less than about 20 micromolar.

While the foregoing specification teaches the principles of the present invention, with examples provided for the purpose of illustration, the practice of the invention encompasses all of the usual variations, adaptations and/or modifications that come within the scope of the following claims.

pyrazidinyl, oxazolyl, isooxazolyl, thiazolyl, isothiazolyl, pyrrolidinyl, pyrazolidinyl imidazolinyl, piperidinyl, piperazinyl, thiazolidinyl, isothiazolidinyl, and morpholinyl;

(ii) a fused bicyclic heterocycle selected from the group consisting of indolyl, isoindolyl, phthalazinyl, purinyl, quinoxalinyl, quinazolinyl, cinnolinyl, 1,6-naphthyridinyl, 1,8-napthyridinyl, benzimidazolyl, quinolinyl, isoquinolinyl, indazolyl, dihydroindolyl, dihydroisoindolyl, tetrahydroquinolyl, tetrahydroisoquinolyl, imidazo[1,2-a]pyrimidinyl, 2,3-dihydroimidazo[2,1-b][1,3]thiazolyl, benzazepinyl, dihydrobenazepinyl, benzodiazepinyl, dihydrobenzodiazepinyl, tetrahydrobenzodiazepinyl, and benzothiazolyl; or (iii) a fused tricyclic heterocycle selected from the group consisting of phenothiazinyl, carbazolyl, beta-carbolinyl, tetrahydro-beta-carbolinyl, acridinyl, phenazinyl, and phenoxazinyl;

$Q^2$ is
(1) —H,
(2) methyl,
(3) ethyl,

---

---

What is claimed is:

1. A compound of Formula (IV):

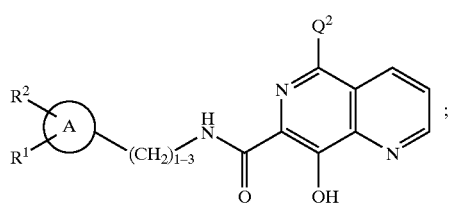

(IV)

wherein

A is
(i) a monocyclic heterocycle selected from the group consisting of pyrrolyl, pyrazolyl, imidazolyl, triazolyl, tetrazolyl, pyridyl, pyrazinyl, pyrimidinyl, (4) $CF_3$,
(5) methoxy,
(6) ethoxy
(7) —$OCF_3$
(8) halo selected from —F, —Cl and —Br,
(9) —CN,
(10) —$CH_2OH$,
(11) —$CH_2OCH_3$
(12) —$(CH_2)_{0-2}CO_2CH_3$,
(13) —$SR^a$,
(14) —$N(R^a)_2$,
(15) —$SO_2R^a$,
(16) —C≡C—$CH_2OR^a$,
(17) —$N(R^a)$—$(CH_2)_{1-3}SR^a$,
(18) —$N(R^a)$—$(CH_2)_{1-3}OR^a$,
(19) —$N(R^a)$—$(CH_2)_{1-3}N(R^a)_2$,
(20) —$N(R^a)$—$(CH_2)_{1-3}N(R^a)$—$C(R^a)$=O,
(21) —$R^k$,

(22) —(CH$_2$)$_{1-4}$R$^k$,
(23) —C≡C—CH$_2$R$^k$,
(24) —O—R$^k$,
(25) —S—R$^k$,
(26) —SO$_2$—R$^k$,
(27) —N(R$^c$)—R$^k$,
(28) —N(R$^c$)—(CH$_2$)$_{1-4}$H substituted with one or two R$^k$ groups,
(29) —N(R$^c$)—(CH$_2$)$_{1-4}$OR$^k$,
(30) —C(=O)N—(CH$_2$)$_{1-4}$R$^k$,
(31) —C≡C—CH$_2$SR$^a$, or
(32) —C≡C—CH$_2$SO$_2$R$^a$;

each of R$^1$ and R$^2$ is independently:
(1) —H,
(2) methyl,
(3) ethyl,
(4) CF$_3$,
(5) methoxy,
(6) ethoxy
(7) —OCF$_3$
(8) halo selected from —F, —Cl and —Br,
(9) —CN,
(10) —CH$_2$OR$^a$,
(11) —CO$_2$R$^a$,
(12) —SR$^a$,
(13) —N(R$^a$)$_2$,
(14) —(CH$_2$)$_{1-3}$N(R$^a$)$_2$,
(15) —SO$_2$R$^a$,
(16) —(CH$_2$)$_{1-2}$N(R$^a$)—C(R$^a$)=O,
(17) —R$^k$,
(18) —(CH$_2$)$_{1-3}$H substituted with 1 or 2 R$^k$ groups,
(19) —O—R$^k$, or
(20) —O—(CH$_2$)$_{1-3}$R$^k$;

each R$^a$ is independently —H or —C$_{1-4}$ alkyl;
each R$^c$ is independently —H, —C$_{1-4}$ alkyl, or —(CH$_2$)$_{1-3}$ N(R$^a$)$_2$;
each R$^k$ is independently:
(1) phenyl which is unsubstituted or substituted with from 1 to 4 substituents independently selected from:
 (a) halogen selected from —F, —Cl, and —Br,
 (b) methyl,
 (c) —CF$_3$,
 (d) methoxy,
 (e) —OCF$_3$,
 (f) phenyl,
 (g) —S—CH$_3$,
 (h) —CN,
 (i) —OH,
 (j) phenyloxy, unsubstituted or substituted with from 1 to 3 substituents independently selected from:
  (i) halogen selected from —F, —Cl, and —Br,
  (ii) methyl,
  (iii) —CF$_3$, and
  (iv) —OH,
 (k) —N(R$^a$)$_2$,
 (l) —(CH$_2$)$_{1-3}$N(R$^a$)$_2$,
 (m) —R$^t$,
 (n) —(CH$_2$)$_{0-3}$C(=O)N(R$^a$)$_2$, and
 (o) —(CH$_2$)$_{0-3}$C(=O)R$_a$;
(2) —C$_{3-6}$ cycloalkyl, unsubstituted or substituted with from 1 to 3 substituents independently selected from:
 (a) halogen selected from —F, —Cl, and —Br,
 (b) methyl,
 (c) —CF$_3$,
 (d) methoxy,
 (e) —OCF$_3$,
 (f) —CN,
 (g) phenyl, and
 (h) —OH;
(3) a 5- or 6-membered heteroaromatic ring selected from thienyl, pyridyl, imidazolyl, pyrrolyl, pyrazolyl, thiazolyl, isothiazolyl, oxazolyl, isooxazolyl, pyrazinyl, pyirimidinyl, triazolyl, tetrazolyl, furanyl, and pyridazinyl, wherein the heteroaromatic ring is unsubstituted or substituted on nitrogen or carbon with 1 or 2 substituents independently selected from:
 (a) halogen selected from —F, —Cl, and —Br,
 (b) methyl,
 (c) —CF$_3$,
 (d) methoxy,
 (e) —OCF$_3$,
 (f) phenyl,
 (g) —S—C$_{1-6}$ alkyl,
 (h) —CN,
 (i) —OH,
 (j) phenyloxy, unsubstituted or substituted with from 1 to 3 substituents independently selected from:
  (i) halogen selected from —F, —Cl, and —Br,
  (ii) methyl,
  (iii) —CF$_3$, and
  (iv) —OH,
 (k) —N(R$^a$)$_2$,
 (l) —C$_{1-6}$ alkyl-N(R$^a$)$_2$,
 (m) —R$^t$,
 (n) oxo,
 (o) —(CH$_2$)$_{0-3}$C(=O)N(R$^a$)$_2$, and
 (p) —(CH$_2$)$_{0-3}$C(=O)R$^a$;
(4) a 5- or 6-membered saturated heterocyclic ring selected from piperidinyl, morpholinyl, thiomorpholinyl, thiazolidinyl, isothiazolidinyl, oxazolidinyl, isooxazolidinyl, pyrrolidinyl, imidazolidinyl, piperazinyl, tetrahydrofuranyl, and pyrazolidinyl, wherein the heterocyclic ring is unsubstituted or substituted with 1 or 2 substituents independently selected from:
 (a) halogen selected from —F, —Cl, and—Br,
 (b) methyl,
 (c) —CF$_3$,
 (d) methoxy,
 (e) —OCF$_3$,
 (f) —CN,
 (g) =O,
 (h) phenyl,
 (i) benzyl,
 (j) phenylethyl,
 (k) —OH,
 (l) —(CH$_2$)$_{0-3}$C(=O)N(R$^a$)$_2$,
 (m) —(CH$_2$)$_{0-3}$C(=O)R$^a$,
 (o) N(R$^a$)—C(=O)OR$^a$,
 (p) (CH$_2$)$_{1-3}$N(R$^a$)—C(=O)R$^a$,
 (q) N(R$^a$)$_2$,
 (r) (CH$_2$)$_{1-3}$N(R$^a$)$_2$,
 (s) —(CH$_2$)$_{0-3}$C(=O)R$^t$,
 (t) —R$^t$,
 (u) —N(R$^a$)R$^t$, and
 (v) —(CH$_2$)$_{1-3}$R$^t$; and
(5) an 8- to 10-membered heterobicyclic ring selected from indolyl, benzotriazolyl, benzoimidazolyl, imidazo[4,5-b]pyridinyl, dihydroimidazo[4,5-b]pyridinyl, pyrazolo[4,3-c]pyridinyl, dihydropyrazolo[4,3-c]pyridinyl, tetrahydropyrazolo[4,3-c]pyridinyl, pyrrolo[1,2-a]pyrazinyl, dihydropyrrolo[1,2-a]pyrazinyl, tetrahydropyrrolo

[1,2-a]pyrazinyl, octahydropyrrolo[1,2-a]pyrazinyl, isoindolyl, indazolyl, indolinyl, isoindolinyl, quinolinyl, isoquinolinyl, quinoxalinyl, quinazolinyl, cinnolinyl, chromanyl, and isochromanyl, wherein the bicyclic ring is unsubstituted or substituted with 1 or 2 substituents independently selected from:
  (a) halogen selected from —F, —Cl, and —Br,
  (b) methyl,
  (c) —CF$_3$,
  (d) methoxy,
  (e) —OCF$_3$,
  (f) —CN,
  (g) =O, and
  (h) —OH;
$R^r$ is selected from pyrrolidinyl, pyrazolidinyl, imidazolinyl, piperidinyl, piperazinyl, pyrrolyl, pyridyl, imidazolyl, pyrazolyl, triazolyl, tetrazolyl, pyrazinyl, pyrimidinyl, and pyradizinyl; any one of which is unsubstituted or substituted with 1 or 2 substituents independently selected from —F, —Cl, —Br, oxo, methyl, and methoxy;
or a pharmaceutically acceptable salt thereof.

2. The compound according to claim 1, wherein each $R^k$ is independently:
  (1) phenyl which is unsubstituted or substituted with from 1 to 2 substituents independently selected from:
    (a) halogen selected from —F, —Cl, and —Br,
    (b) methyl,
    (c) —CF$_3$,
    (d) methoxy,
    (e) —OCF$_3$,
    (f) phenyl,
    (g) —S—CH$_3$,
    (h) —CN,
    (i) —OH,
    (j) phenyloxy
    (k) —N(R$^a$)$_2$,
    (l) —(CH$_2$)$_{1-3}$N(R$^a$)$_2$,
    (m) —R$^t$,
    (n) —(CH$_2$)$_{0-3}$C(=O)N(R$^a$)$_2$, and
    (o) —(CH$_2$)$_{0-3}$C(=O)R$_a$;
  (2) —C$_{3-6}$ cycloalkyl;
  (3) a 5- or 6-membered heteroaromatic ring selected from thienyl, pyridyl, imidazolyl, pyrrolyl, pyrazolyl, thiazolyl, isothiazolyl, pyrazinyl, pyirimidinyl, triazolyl, and tetrazolyl, wherein the heteroaromatic ring is unsubstituted or substituted on nitrogen or carbon with 1 or 2 substituents independently selected from:
    (a) halogen selected from —F, —Cl, and —Br,
    (b) methyl,
    (c) —CF$_3$,
    (d) methoxy,
    (e) —OCF$_3$,
    (f) —S—C$_{1-6}$ alkyl,
    (g) —CN,
    (h) —OH,
    (i) —N(R$^a$)$_2$,
    (j) —C$_{1-6}$alkyl—N—(R$^a$)$_2$,
    (k) —R$^t$,
    (l) oxo,
    (m) —(CH$_2$)$_{0-3}$C(=O)N(R$^a$)$_2$, and
    (n) —(CH$_2$)$_{0-3}$C(=O)R$_a$;
  (4) a 5- or 6-membered saturated heterocyclic ring selected from piperidinyl, morpholinyl, thiomorpholinyl, thiazolidinyl, isothiazolidinyl, oxazolidinyl, isooxazolidinyl, pyrrolidinyl, imidazolidinyl and, piperazinyl, wherein the heterocyclic ring is unsubstituted or substituted with 1 or 2 substituents independently selected from:
    (a) halogen selected from —F, —Cl, and —Br,
    (b) methyl,
    (c) —CF$_3$,
    (d) methoxy,
    (e) —OCF$_3$,
    (f) —CN,
    (g) =O,
    (h) phenyl,
    (i) benzyl,
    (j) phenylethyl,
    (k) —OH,
    (l) —(CH$_2$)$_{0-3}$C(=O)N(R$^a$)$_2$,
    (m) —(CH$_2$)$_{0-3}$C(=O)R$^a$,
    (n) N(R$^a$)—C(=O)R$^a$,
    (o) N(R$^a$)—C(=O)OR$^a$,
    (p) (CH$_2$)$_{1-3}$N(R$^a$)—C(=O)R$^a$,
    (q) N(R$^a$)$_2$,
    (r) (CH$_2$)$_{1-3}$N(R$^a$)$_2$,
    (s) —(CH$_2$)$_{0-3}$C(=O)R$^t$,
    (t) —R$^t$,
    (u) —N(R$^a$)R$^t$, and
    (v) —(CH$_2$)$_{1-3}$R$^t$; and
  (5) an 8- to 10-membered heterobicyclic ring selected from indolyl, imidazo[4,5-b]pyridinyl, dihydroimidazo[4,5-b]pyridinyl, pyrazolo[4,3-c]pyridinyl, dihydropyrazolo[4,3-c]pyridinyl, tetrahydropyrazolo[4,3-c]pyridinyl, pyrrolo[1,2-a]pyrazinyl, dihydropyrrolo[1,2-a]pyrazinyl, tetrahydropyrrolo[1,2-a]pyrazinyl, octahydropyrrolo[1,2-a]pyrazinyl, isoindolyl, indazolyl, indolinyl, isoindolinyl, quinolinyl, isoquinolinyl, quinoxalinyl, and quinazolinyl, wherein the bicyclic ring is unsubstituted or substituted with 1 or 2 substituents independently selected from:
    (a) halogen selected from —F, —Cl, and —Br,
    (b) methyl,
    (c) —CF$_3$,
    (d) methoxy,
    (e) —OCF$_3$,
    (f) —CN,
    (g) =O, and
    (h) —OH; and
$R^r$ is selected from pyrrolidinyl, pyrazolidinyl, imidazolinyl, piperidinyl, piperazinyl, pyrrolyl, pyridyl, imidazolyl, pyrazolyl, triazolyl, tetrazolyl, pyrazinyl, pyrimidinyl, and pyradizinyl; any one of which is unsubstituted or substituted with 1 or 2 substituents independently selected from —F, —Cl, —Br, oxo, methyl, and methoxy;
or a pharmaceutically acceptable salt thereof.

3. The compound according to claim 2, wherein A is
  (i) a monocyclic heterocycle selected from the group consisting of pyrrolyl, pyrazolyl, imidazolyl, triazolyl, tetrazolyl, pyridyl, oxazolyl, isooxazolyl, thiazolyl, pyrrolidinyl, piperidinyl, piperazinyl, thiazolidinyl, and morpholinyl;
  (ii) a fused bicyclic heterocycle selected from the group consisting of indolyl, isoindolyl, phthalazinyl, benzimidazolyl, quinolinyl, isoquinolinyl, dihydroindolyl, dihydroisoindolyl, tetrahydroquinolyl, tetrahydroisoquinolyl, imidazo[1,2-a]pyrimidinyl, 2,3-dihydroimidazo[2,1-b][1,3]

thiazolyl, benzazepinyl, dihydrobenazepinyl, benzodiazepinyl, dihydrobenzodiazepinyl, benzothiazolyl and tetrahydrobenzodiazepinyl; or
(iii) a fused tricyclic heterocycle selected from the group consisting of phenothiazinyl, beta-carbolinyl, and tetrahydro-beta-carbolinyl;

or a pharmaceutically acceptable salt thereof.

4. The compound according to claim 3, wherein A is selected from the group consisting of indolyl, phenothiazinyl, benzimidazolyl, phthalazinyl, and dihydroimidazothiazolyl;

or a pharmaceutically acceptable salt thereof.

5. The compound according to claim 3, wherein A is indolyl; or a pharmaceutically acceptable salt thereof.

6. A compound according to claim 1, which is a compound selected from the group consisting of 2-({[(8-hydroxy-1,6-naphthyridin-7-yl)carbonyl]amino}methyl)-1H-benzimidazole;

8-hydroxy-N-[2-(1H-indol-3-yl)ethyl]-1,6-naphthyridine-7-carboxamide;

N-{2-[2-(3,4-dimethoxyphenyl)-1H-indol-3-yl]ethyl}-8-hydroxy-1,6-naphthyridine-7-carboxamide;

8-hydroxy-N-[(2-oxo-2,3-dihydro-1H-indol-3-yl)methyl]-1,6-naphthyridine-7-carboxamide;

8-hydroxy-N-[2-(10H-phenothiazin-10-yl)ethyl]-1,6-naphthyridine-7-carboxamide;

8-hydroxy-N-[2-(2-methyl-1-phenyl-1H-indol-3-yl)ethyl]-1,6-naphthyridine-7-carboxamide;

8-hydroxy-N-(1H-indol-6-ylmethyl)-1,6-naphthyridine-7-carboxamide;

8-hydroxy-N-(1H-indol-2-ylmethyl)-1,6-naphthyridine-7-carboxamide;

8-hydroxy-N-[(4-oxo-3,4-dihydrophthalazin-1-yl)methyl]-1,6-naphthyridine-7-carboxamide;

tert-butyl 3-({[(8-hydroxy-1,6-naphthyridin-7-yl)carbonyl]amino}methyl)-1H-indole-1-carboxylate;

8-hydroxy-N-(1H-indol-3-ylmethyl)-1,6-naphthyridine-7-carboxamide;

6-({[(8-hydroxy-1,6-naphthyridin-7-yl)carbonyl]amino}methyl)-2,3-dihydroimidazo[2,1-b][1,3]thiazole;

8-hydroxy-N-(4-pyridinylmethyl)[1,6]naphthyridine-7-carboxamide;

8-hydroxy-N-(2-pyridinylmethyl)[1,6]naphthyridine-7-carboxamide;

and pharmaceutically acceptable salts thereof.

7. A pharmaceutical composition comprising a therapeutically effective amount of a compound according to claim 1, or a pharmaceutically acceptable salt thereof, and a pharmaceutically acceptable carrier.

8. A method for treating infection by HIV or treating or delaying the onset of AIDS in a subject in need thereof which comprises administering to the subject a therapeutically effective amount of the compound according to claim 1, or a pharmaceutically acceptable salt thereof.

9. A method for treating infection by HIV or for treating or delaying the onset of AIDS in a subject in need thereof which comprises administering to the subject a therapeutically effective amount of the composition according to claim 7.

10. A pharmaceutical composition which comprises the product prepared by combining an effective amount of a compound of claim 1, or a pharmaceutically acceptable salt thereof, and a pharmaceutically acceptable carrier.

* * * * *